US006852716B2

(12) United States Patent
Walker et al.

(10) Patent No.: US 6,852,716 B2
(45) Date of Patent: Feb. 8, 2005

(54) SUBSTITUTED-ARYL COMPOUNDS FOR TREATMENT OF DISEASE

(75) Inventors: Daniel Patrick Walker, Kalamazoo, MI (US); David W. Piotrowski, Portage, MI (US); Eric Jon Jacobsen, Richland, MI (US); Brad A. Acker, Kalamazoo, MI (US); Jason K. Myers, Kalamazoo, MI (US); Vincent E. Groppi, Jr., Kalamazoo, MI (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/361,705

(22) Filed: Feb. 10, 2003

(65) Prior Publication Data

US 2003/0236279 A1 Dec. 25, 2003

Related U.S. Application Data

(60) Provisional application No. 60/358,083, filed on Feb. 20, 2002, provisional application No. 60/357,472, filed on Feb. 15, 2002, and provisional application No. 60/357,465, filed on Feb. 15, 2002.

(51) Int. Cl.$^7$ .................. A61K 31/55; A61K 31/4439; A61K 31/439; C07D 471/08; C07D 487/08
(52) U.S. Cl. .................. 514/214.03; 514/299; 514/339; 514/413; 514/363; 514/364; 514/372; 514/380; 514/369; 514/376; 514/393; 540/582; 540/585; 546/112; 546/276.7; 548/452; 548/228; 548/229; 548/142; 548/144; 548/213; 548/243; 548/181; 548/312.1
(58) Field of Search .......................... 546/112, 276.7; 540/582, 585; 548/452, 228, 229, 142, 144, 213, 243, 312.1, 181; 514/299, 339, 214.03, 413, 363, 364, 372, 380, 369, 376, 393

(56) References Cited

U.S. PATENT DOCUMENTS

| | | | | |
|---|---|---|---|---|
| 3,702,324 A | 11/1972 | Skinner et al. | ........ | 260/293.53 |
| 4,093,734 A | 6/1978 | Kruger et al. | .............. | 424/274 |
| 4,593,034 A | 6/1986 | Munson, Jr. et al. | ....... | 514/305 |
| 4,605,652 A | 8/1986 | Welstead, Jr. | ................ | 514/214 |
| 4,657,911 A | 4/1987 | Imbert et al. | ................ | 514/272 |
| 4,717,563 A | 1/1988 | Alphin et al. | .................. | 424/10 |
| 4,721,720 A | 1/1988 | Wootton et al. | ............. | 514/304 |
| 4,798,829 A | 1/1989 | King et al. | .................. | 514/214 |
| 4,803,199 A | 2/1989 | Donatsch et al. | ........... | 514/214 |
| 4,820,715 A | 4/1989 | Monkovic et al. | .......... | 514/305 |
| 4,835,162 A | 5/1989 | Abood | ........................ | 514/305 |
| 4,870,181 A | 9/1989 | Lo | ............................. | 546/133 |
| 4,877,780 A | 10/1989 | Vega-Noverola et al. | ... | 514/161 |
| 4,877,794 A | 10/1989 | Naylor et al. | ................ | 514/305 |
| 4,908,370 A | 3/1990 | Naylor et al. | ................ | 514/305 |
| 5,017,580 A | 5/1991 | Naylor et al. | ................ | 514/299 |
| 5,025,022 A | 6/1991 | Naylor et al. | ................ | 514/305 |
| 5,039,680 A | 8/1991 | Impoerato et al. | .......... | 514/304 |
| 5,057,519 A | 10/1991 | Suberg | ....................... | 514/282 |
| 5,070,095 A | 12/1991 | Jagdmann, Jr. et al. | ..... | 514/305 |
| 5,084,460 A | 1/1992 | Munson, Jr. et al. | ........ | 514/282 |
| 5,106,843 A | 4/1992 | Ward et al. | .................. | 514/213 |
| 5,175,173 A | 12/1992 | Sun | ............................. | 514/305 |
| 5,206,246 A | 4/1993 | Langlois et al. | ............. | 514/272 |
| 5,236,931 A | 8/1993 | Jagdmann et al. | .......... | 514/305 |
| 5,237,066 A | 8/1993 | Dorme et al. | ................ | 546/133 |
| 5,273,972 A | 12/1993 | Jagdmann et al. | .......... | 514/210 |
| 5,561,149 A | 10/1996 | Azria et al. | .................. | 514/397 |
| 5,723,103 A | 3/1998 | de Paulis et al. | ........... | 424/1.85 |
| 5,919,793 A | 7/1999 | Brown et al. | ................ | 514/305 |
| 5,977,144 A | 11/1999 | Meyer et al. | ................ | 514/334 |
| 2003/0055043 A1 * | 3/2003 | Jacobsen et al. | ....... | 514/214.03 |

FOREIGN PATENT DOCUMENTS

| | | | | |
|---|---|---|---|---|
| FR | 2625678 | 1/1988 | ......... | A61K/31/435 |
| WO | WO 91/09593 | 7/1991 | .......... | A61K/31/00 |
| WO | WO 92/11259 | 7/1992 | ......... | C07D/451/04 |
| WO | WO 92/15579 | 9/1992 | ......... | C07D/451/00 |
| WO | WO 97/30998 | 8/1997 | ......... | C07D/453/02 |
| WO | WO 00/73431 A2 | 12/2000 | .......... | C12N/15/00 |
| WO | WO01/29034 | 4/2001 | ......... | C07D/453/02 |
| WO | WO 01/36417 A1 | 5/2001 | ......... | C07D/451/04 |
| WO | WO01/60821 | 8/2001 | ......... | C07D/453/02 |
| WO | WO 01/76576 | 10/2001 | .......... | A61K/31/00 |

OTHER PUBLICATIONS

Bannon, A.W., *American Association for the Advancement of Science.* Broad–Spectrum, Non–Opiodid Analgesic Activity by Selective Modulation of Neuronal Nicotinic Acetylcholine Receptors. vol. 279, No 5347, pp. 77–81, 1998.

Dineley, K.T., and James W. Patrick, *The Journal of Biological Chemistry.* Amino Acid Determinants of •7 Nicotinic Acetylcholine Receptor Surface Expression. vol. 275, No 18, pp. 13974–13985, May 5, 2000.

Eisele, Jean–Luc. *Letters to Nature.* Chimaeric nicotinic–serotonergic receptor combines distinct ligand binding and channel specificities. vol. 366, pp. 479–483, Dec. 2, 1993.

(List continued on next page.)

Primary Examiner—Evelyn Huang
(74) Attorney, Agent, or Firm—Peter C. Richardson; Andrea E. Dorigo; Lorraine B. Ling

(57) ABSTRACT

The invention provides compounds of Formula I:

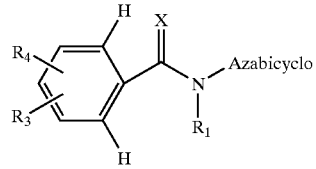

Formula I

These compounds may be in the form of pharmaceutical salts or compositions, racemic mixtures, or pure enantiomers thereof. The compounds of Formula I are useful in pharmaceuticals to treat diseases or conditions in which α7 is known to be involved.

12 Claims, No Drawings

OTHER PUBLICATIONS

Holladay, Mark W., et. al., *Journal of Medicinal Chemistry*. Neuronal Nicotinic Acetylcholine Receptors as Targets for Drug Discovery. Dec. 19, 1997.

Kem, William R. *Behavioral Brian Research*. "The brain α7 nicotinic receptor may be an important therapeutic target for the treatment of Alzheimer's disease: studies with DMXBA (GTS–21)." 113 (2000) 169–181.

Kuntzweiler, Theresa A., et. al. *Drug Development Research*. "Rapid Assessment of Ligand Actions with Nicotinic Acetylcholine Receptors Using Calcium Dynamics and FLIPR." vol. 44, No. 1, pp. 14–20, May 1998.

Macor, JE. *Bioorganic & Medicinal Chemistry Letters*. "The 5–HT$_s$ Antagonist Tropisetron ( ICS 205–930) is a Potent and Selective α7 Nicotinic Receptor Partial Agonist." 11 (2001) 319–321.

* cited by examiner

SUBSTITUTED-ARYL COMPOUNDS FOR TREATMENT OF DISEASE

CROSS-REFERENCE TO RELATED APPLICATIONS

This application claims the benefit of U.S. provisional application Ser. No. 60/357,465 and U.S. provisional application Ser. No. 60/357,472 both of which were filed on Feb. 15, 2002, under 35 USC 119(e)(i), and U.S. provisional application Ser. No. 60/358,083 filed on Feb. 20, 2002, under 35 USC 119(e)(i), which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides compounds that are active drug molecules with fewer side effects.

The invention also concerns the synthesis of and isolation of intermediates and final compounds. Specifically, the present invention concerns the stereospecific synthesis of (3R,5R)-1-azabicyclo[3.2.1]octan-3-amine or salts thereof.

BACKGROUND OF THE INVENTION

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The α7 nAChR is one receptor system that has proved to be a difficult target for testing. Native α7 nAChR is not routinely able to be stably expressed in most mammalian cell lines (Cooper and Millar, *J. Neurochem.*, 1997, 68(5): 2140–51). Another feature that makes functional assays of α7 nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the α7 nAChR (Eisele et al., *Nature*, 366(6454), p 479–83, 1993), and the pore forming C-terminal domain of the 5-HT$_3$ receptor expressed well in *Xenopus* oocytes while retaining nicotinic agonist sensitivity. Eisele et al. used the N-terminus of the avian (chick) form of the α7 nAChR receptor and the C-terminus of the mouse form of the 5-HT$_3$ gene. However, under physiological conditions the α7 nAChR is a calcium channel while the 5-HT$_3$R is a sodium and potassium channel. Indeed, Eisele et al. teaches that the chicken α7 nAChR/mouse 5-HT$_3$R behaves quite differently than the native α7 nAChR with the pore element not conducting calcium but actually being blocked by calcium ions. WO 00/73431 A2 reports on assay conditions under which the 5-HT$_3$R can be made to conduct calcium. This assay may be used to screen for agonist activity at this receptor.

U.S. Pat. No. 5,977,144 discloses compositions for benzylidene- and cinnamylidene-anabaseines and methods for using these compositions for treating conditions associated with defects or malfunctioning of nicotinic subtypes brain receptors. These compositions target the α7 receptor subtype with little or no activation of the α4β2 or other receptor subtypes.

U.S. Pat. No. 5,919,793 discloses heterocyclic derivatives useful in lowering cholesterol levels in blood plasma.

U.S. Pat. No. 5,741,819 discloses arylsulfonylbenzene derivatives and their use as factor Xa inhibitors as being useful for the treatment of arterial and venous thrombotic occlusive disorders, inflammation, cancer, and neurodegenerative diseases.

U.S. Pat. No. 5,723,103 discloses substituted benzamides and radioligand analogs and methods of using the compounds for the identification of 5-HT$_3$ receptors and the detection and treatment of abnormal conditions associated therewith.

U.S. Pat. No. 5,561,149 discloses the use of a mono or bicyclic carbocyclic, or heterocyclic carboxylic, acid ester or amide or an imidazolyl carbazol in the manufacture of a medicament suitable for the treatment of stress-related psychiatric disorders, for increasing vigilance, for the treatment of rhinitis or serotonin-induced disorders and/or coadministration with another active agent to increase the bioavailability thereof, or for nasal administration.

U.S. Pat. No. 5,273,972 discloses novel 2-substituted-3-quinuclidinyl arylcarboxamides and arylthiocarboxamides and corresponding arylcarboxylates which have utility as therapeutic agents which exhibit gastric prokinetic, antiemetic, anxiolytic and 5-HT (serotonin) antagonist effects in warm blooded animals.

U.S. Pat. No. 5,237,066 discloses enantiomers of absolute configuration S of amide derivatives of 3-aminoquinuclidine, the process for preparing them and their use as medicinal products having activity in respect of gastric movements and antiemetic activity.

U.S. Pat. No. 5,236,931 discloses novel 3-quinuclidinyl benzamides and benzoates which have utility as therapeutical agents which exhibit anxiolytic, antipsychotic, cognition improvement, antiemetic and gastric prokinetic effects in warm blooded animals.

U.S. Pat. No. 5,206,246 discloses anxiolytic-R—N-(1-azabicyclo[2.2.2]oct-3-yl)benzamides and thiobenzamides, their N-oxides and pharmaceutically acceptable salts thereof. A preferred compound is R-(+)-4-amino-N-(1-azabicyclo[2.2.2]oct-3-yl)-5-chloro-2-methoxybenzamide.

U.S. Pat. No. 5,106,843 discloses heterocyclic compounds useful as 5-HT$_3$ antagonists.

U.S. Pat. No. 5,084,460 discloses methods of therapeutic treatment with N-(3-quinuclidinyl)-2-hydroxybenzamides and thiobenzamides. The therapeutic agents are disclosed as exhibiting anxiolytic antipsychotic and cognitive improving effects in warm blooded animals.

U.S. Pat. No. 5,070,095 discloses novel 1-(azabicyclo [2.2.2]oct-3- or -4-yl)benzamides substituted on the benzene ring with the basic substituted aminomethyleneamino group which has been found to be useful in treating emesis, including emesis due to chemical and radiation anticancer therapy, anxiety, and impaired gastric emptying.

U.S. Pat. No. 5,057,519 discloses 5-HT$_3$ antagonists as being useful in reducing opiate tolerance.

U.S. Pat. No. 5,039,680 disclose 5-HT$_3$ antagonists in preventing or reducing dependency on dependency-inducing agents.

U.S. Pat. No. 5,025,022 discloses a method of treating or preventing schizophrenia and/or psychosis using S—N-(1-azabicyclo[2.2.2]oct-3-yl)benzamides and thiobenzamides, their N-oxides and pharmaceutically acceptable salts thereof. A preferred compound is S(−)-4-amino-N-(1-azabicyclo[2.2.2]oct-3-yl)-5-chloro-2-methoxybenzamide.

U.S. Pat. No. 5,017,580 discloses memory enhancing-R—N-(1-azabicyclo[2.2.2]oct-3-yl)benzamides and thiobenzamides, their N-oxides and pharmaceutically acceptable salts thereof. A preferred compound is R-(+)-4-amino-N-(1-azabicyclo[2.2.2]oct-3-yl)-5-chloro-2-methoxybenzamide.

U.S. Pat. No. 4,908,370 discloses anxiolytic-N-(1-azabicyclo[2.2.2]oct-3-yl)benzamides and thiobenzamides as having anxiolytic activity, in particular, activity against anxiety induced by the withdrawal from ingested substances such as narcotics.

U.S. Pat. No. 4,877,794 discloses 2-alkoxy-N-(1-azabicyclo[2.2.2]oct-3-yl)benzamide and thiobenzamide compositions and the use thereof to treat schizophrenia.

U.S. Pat. No. 4,877,780 discloses antiemetic N-substituted benzamides having pharmaceutical properties rendering them useful as antiemetic agents with reduced undesirable side effects.

U.S. Pat. No. 4,870,181 discloses a process for the preparation of 2-alkoxy-N-(1-azabicyclo[2.2.2])octan-3-yl) aminobenzamide.

U.S. Pat. No. 4,835,162 discloses agonists and antagonists to nicotine as smoking deterrents.

U.S. Pat. No. 4,820,715 discloses anti-emetic quinuclidinyl benzamides. The compounds are particularly useful in the treatment of chemotherapy-induced emesis in cancer patients. Some of the compounds are also useful in disorders relating to impaired gastric motility.

U.S. Pat. No. 4,803,199 discloses pharmaceutically useful heterocyclic acid esters and amides or alkylene bridged peperidines as serotonin M antagonists.

U.S. Pat. No. 4,798,829 discloses 1-azabicyclo[3.2.2] nonane derivatives having gastric motility enhancing activity and/or anti-emetic activity and/or 5-HT receptor antagonist activity.

U.S. Pat. No. 4,721,720 discloses a method of treating emesis, anxiety and/or irritable bowel syndrome.

U.S. Pat. No. 4,717,563 discloses 2-alkoxy-N-(1-azabicyclo[2.2.2]oct-3-yl)benzamides and thiobenzamides in a method for alleviating emesis caused by non-platinum anticancer drugs.

U.S. Pat. No. 4,657,911 discloses 3-amino quinuclidine derivatives and the application thereof as accelerators of gastro-intestinal motor function and as medicament potentiators.

U.S. Pat. No. 4,605,652 discloses a method of enhancing memory or correcting memory deficiency with arylamido (and arylthioamido)-azabicycloalkanes, and the pharmaceutically acceptable acid addition salts, hydrates and alcoholates thereof.

U.S. Pat. No. 4,593,034 discloses 2-alkoxy-N-(1-azabicyclo[2.2.2]oct-3-yl)benzamides and thiobenzamides having gastrokinetic and anti-emetic activity.

U.S. Pat. No. 4,093,734 discloses amino-benzoic acid amides useful as anxiolytics, anticonvulsives, antiemetics and antiulcerogenics.

U.S. Pat. No. 3,702,324 discloses 3,4,5-trimethoxybenzamides of substituted anilines and of alkylpiperidines which exert a specific effect on the central nervous system and a somewhat lesser effect on muscle function, and thus have utility as tranquilizers.

WO 01/76576 A2 discloses a pharmaceutical composition for treatment of acute, chronic pain and/or neuropathic pain and migraines.

WO 01/60821 A1 discloses novel biarylcarboxamides and their use in therapy, especially in the treatement of prophylaxis of psychotic and intellectual impairment conditions.

WO 01/36417 A1 discloses novel N-azabicyclo-amide derivatives and use in therapy, especially in the treatment of prophylaxis of psychotic disorders and intellectual impairment disorders.

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

WO 92/15579 discloses multicyclic tertiary amine polyaromatic squalene synthase inhibitors and method of treatment for lowering serum cholesterol levels using the compounds.

WO 92/11259 discloses azabicyclic amides or esters of halogenated benzoic acids having 5-HT$_3$ receptor antagonist activity.

FR 2 625 678 discloses N-(quinuclidin-3-yl)-benzamides and thiobenzamides useful as diet-control agents.

In *Bioorg. & Med. Chem. Lett.* 11 (2001) 319–321, the 5-HT$_3$ antagonist tropisetron (ICS 205–930) is discussed as a potent and selective α7 nicotinic receptor partial agonist.

In *Behavioral Brain Res.*, 113 (2000) 169–181, it is discussed that the brain α7 nicotinic receptor may be an important therapeutic target for the treatment of Alzheimer's disease using DMXBA which is known as GTS-21.

SUMMARY OF THE INVENTION

The present invention discloses compounds of the Formula I:

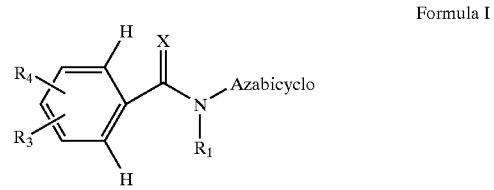

Formula I wherein X is O or S;
Azabicyclo is

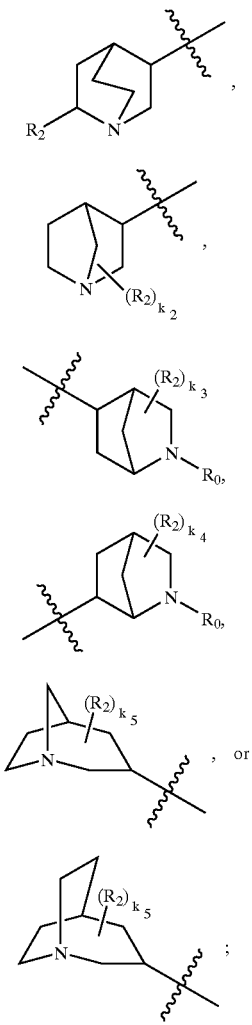

R₀ is H, lower alkyl, lower substituted alkyl, or lower halogenated alkyl;

R₁ is independently H, alkyl, cycloalkyl, halogenated alkyl, and aryl;

R₂ is F, Cl, Br, I, alkyl, halogenated alkyl, substituted alkyl, cycloalkyl, or aryl, provided that when Azabicyclo is I, R₂ is alkyl, halogenated alkyl, substituted alkyl, cycloalkyl, or aryl, provided that R₂ is absent when any of k₂, k₃, k₄, k₅, or k₆ is 0;

k₂ is 0 or 1;
k₃ is 0 or 1;
k₄ is 0 or 1;
k₅ is 0, 1, or 2;
k₆ is 0, 1, or 2;

R₃ is H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, aryl, R₇, R₉, —OR₈, —OR₁₇, —SR₈, —S(O)₂R₈, —S(O)R₈, —OS(O)₂R₈, —NR₈R₈, —NR₁₅R₁₅, —C(O)R₈, —C(O)R₁₆, —C(S)R₈, —C(O)OR₈, —CN, —C(O)NR₈R₈, —C(O)NR₁₅R₁₅, —NR₈C(O)R₈, —S(O)₂NR₈R₈, —NR₈S(O)₂R₈, —NO₂, —N(R₈)C(O)NR₈R₈, —N(H)C(O)N(H)R₈, substituted alkyl, substituted alkenyl, substituted alkynyl, substituted cycloalkyl, substituted heterocycloalkyl, phenyl, phenyl having 1–4 substituents independently selected from F, Cl, Br, I and R₂₁, naphthyl, or naphthyl having 1–4 substituents independently selected from F, Cl, Br, I, R₂₁;

R₄ is —O—R₅, —S—R₅, —S(O)—R₅, —C(O)—R₅, or alkyl substituted on the ω carbon with R₅ where said ω carbon is determined by counting the longest carbon chain of the alkyl moiety with the C-1 carbon being the carbon attached to the phenyl ring of the core molecule and the ω carbon being the carbon furthest from said C-1 carbon;

R₅ is aryl, R₇, or R₉;

R₇ is 5-membered heteroaromatic mono-cyclic moieties containing within the ring 1–3 heteroatoms independently selected from —O—, =N—, —N(R₁₄)—, and —S—, and having 0–1 substituent selected from R₁₂ and 0–3 substituents independently selected from F, Cl, Br, or I, or R₇ is a 9-membered fused-ring moiety having a 6-membered ring fused to a 5-membered ring and having the formula

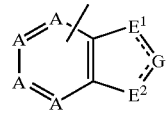

wherein each A is independently CR₁₈ or N, provided that only up to one A is N, E¹ and E² are independently selected from CR₁₈, O, S, or NR₁₄, and G is CR₁₈, provided that R₁₈ or R₁₄ of E¹, E², and G can be a bond when - - - forms a double bond and further provided that R₁₈ or R₁₄ can be a bond for bonding R₇ to a moiety to which it is attached;

Each R₈ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R₇, R₉, phenyl, or substituted phenyl;

R₉ is 6-membered heteroaromatic mono-cyclic moieties containing within the ring 1–3 heteroatoms selected from =N— and having 0–1 substituent selected from R₁₂ and 0–3 substituent(s) independently selected from F, Cl, Br, or I, or R₉ is 10-membered heteroaromatic bi-cyclic moieties containing within one or both rings 1–3 heteroatoms selected from =N—, including quinolinyl or isoquinolinyl, each 10-membered fused-ring moiety having 0–1 substituent selected from R₁₂ and 0–3 substituent(s) independently selected from F, Cl, Br, or I and having a bond for bonding R₉ to a moiety to which it is attached where valency allows;

Each R₁₀ is independently H, alkyl, cycloalkyl, heterocycloalkyl, alkyl substituted with 1 substituent selected from R₁₃, cycloalkyl substituted with 1 substituent selected from R₁₃, heterocycloalkyl substituted with 1 substituent selected from R₁₃, halogenated alkyl, halogenated cycloalkyl, halogenated heterocycloalkyl, phenyl, or phenyl having 1 substituent selected from R₂₀ and further having 0–3 substituents independently selected from F, Cl, Br, or I;

Each R₁₁ is independently H, alkyl, cycloalkyl, heterocycloalkyl, halogenated alkyl, halogenated cycloalkyl, or halogenated heterocycloalkyl;

R₁₂ is —OR₁₁, —SR₁₁, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —NR₁₁R₁₁, —C(O)R₁₁, —NO₂, —C(O)NR₁₁R₁₁, —CN, —NR₁₁C(O)R₁₁, —S(O)₂NR₁₁R₁₁, or —NR₁₁S(O)₂R₁₁;

R₁₃ is —OR₁₁, —SR₁₁, —NR₁₁R₁₁, —C(O)R₁₁, —C(O)NR₁₁R₁₁, —CN, —CF₃, —NR₁₁C(O)R₁₁, —S(O)₂NR₁₁R₁₁, —NR₁₁S(O)₂R₁₁, or —NO₂;

$R_{14}$ is a bond, H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, phenyl having 1 substituent selected from $R_{20}$ and further having 0–3 substituents independently selected from F, Cl, Br, or I;

Each $R_{15}$ is independently alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Each $R_{16}$ is independently cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Each $R_{17}$ is independently cycloalkyl, halogenated cycloalkyl, substituted cycloalkyl, heterocycloalkyl, halogenated heterocycloalkyl, or substituted heterocycloalkyl;

Each $R_{18}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$N(R_{11})_2$, —$C(O)R_{11}$, —$NO_2$, —C(O)N$(R_{11})_2$, —CN, —$NR_{11}C(O)R_{11}$, —$S(O)_2N(R_{11})_2$, or —$NR_{11}S(O)_2R_{11}$, F, Cl, Br, or I, or a bond;

$R_{19}$ is H, alkyl, halogenated alkyl, substituted alkyl, cycloalkyl, halogenated cycloalkyl, substituted cycloalkyl, phenyl, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —$OR_{11}$, —$SR_{11}$, —$N(R_{11})_2$, —$C(O)R_{11}$, —$C(O)N(R_{11})_2$, —CN, —$NR_{11}C(O)R_{11}$, —$S(O)_2N(R_{11})_2$, —$NR_{11}S(O)_2R_{11}$, —$NO_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or $R_{13}$;

Each $R_{21}$ is independently alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or phenyl having 1 substituent selected from $R_{20}$ and further having 0–3 substituents independently selected from F, Cl, Br, or I;

or pharmaceutical composition, pharmaceutically acceptable salt, racemic mixture, or pure enantiomer thereof.

The compounds of Formula I are used to treat a disease or condition, wherein the diseases, disorders, and/or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

Embodiments of the invention may include one or more or combination of the following.

The compound of Formula I, wherein X is O. The compound of Formula I, where X is S.

The compound of Formula I, where Azabicyclo is any one or more of I, II, III, IV, V, or VI.

Another group of compounds of Formula I include compounds where $R_1$ is any one of the following: H, alkyl, cycloalkyl, halogenated alkyl, and aryl. Another group of compounds of Formula I include compounds where $R_1$ is H, lower alkyl, or lower cycloalkyl.

Another group of compounds of Formula I include compounds where Azabicyclo is II, V, or VI and where each $k_2$, $k_5$, and $k_6$ is independently 0 or 1. Another group of compounds of Formula I include compounds where $R_2$ is lower alkyl, lower halogenated alkyl, lower substituted alkyl, or is absent provided that $k_2$, $k_3$, $k_4$, $k_5$, or $k_6$ is 0. When $k_2$, $k_3$, $k_4$, $k_5$, or $k_6$ is 0, $R_2$ is "absent." Another group of compounds of Formula I include compounds where $R_1$ is H or lower alkyl, and wherein $R_2$ is lower alkyl or is absent.

Another group of compounds of Formula I include compounds where Azabicyclo is I and where $R_2$ is lower alkyl, lower halogenated alkyl, or lower substituted alkyl, or where Azabicyclo is III or IV and where $R_2$ is absent, lower alkyl, or lower substituted alkyl.

Another group of compounds within the present invention includes compounds where X is O. The present invention also includes compounds where $R_0$ is H. Other compounds within the scope of the present invention are where $R_0$ is methyl. The present invention also includes compounds where $R_1$ is H. Other compounds within the scope of the present invention are where $R_1$ is alkyl, cycloalkyl, halogenated alkyl, or aryl. The present invention also includes compounds where $R_2$ is absent, provided that $R_2$ is present when Azabicyclo is I. Other compounds within the scope of the present invention are where $R_2$ is alkyl, halogenated alkyl, substituted alkyl, cycloalkyl, or aryl.

Another group of compounds within the present invention includes compounds where $R_3$ is any one or more of the following: H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, aryl, $R_7$, $R_9$, —$OR_8$, —$OR_{17}$, —$SR_8$, —$S(O)_2R_8$, —$S(O)R_8$, —$OS(O)_2R_8$, —$NR_8R_8$, —$NR_{15}R_{15}$, —$C(O)R_8$, —$C(O)R_{16}$, —$C(S)R_8$, —$C(O)OR_8$, —CN, —$C(O)NR_8R_8$, —$C(O)NR_{15}R_{15}$, —$NR_8C(O)R_8$, —$S(O)_2NR_8R_8$, —$NR_8S(O)_2R_8$, —$NO_2$, —$N(R_8)C(O)NR_8R_8$, —N(H)C(O)N(H)$R_8$, substituted alkyl, substituted alkenyl, substituted alkynyl, substituted cycloalkyl, substituted heterocycloalkyl, phenyl, phenyl having 1–4 substituents independently selected from F, Cl, Br, I and $R_{21}$, naphthyl, or naphthyl having 1–4 substituents independently selected from F, Cl, Br, I, $R_{21}$. Another group of compounds within the present invention includes compounds where $R_3$ is H. Another group of compounds within the present invention includes compounds where $R_3$ is any one or more of the following: H, F, Cl, Br, I, lower alkyl, lower halogenated alkyl, —$OR_8$, —$OR_{17}$, —$N(R_8)_2$, —$NR_{15}R_{15}$, —C(O)N$(R_8)_2$, —$NR_8C(O)R_8$.

Another group of compounds within the present invention includes compounds where each $R_8$ is independently any one or more of the following: H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl.

Another group of compounds within the present invention includes compounds where each $R_{10}$ is independently any one or more of the following: H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or phenyl having 1 substituent selected from $R_{20}$ and further having 0–3 substituents independently selected from F, Cl, Br, or I.

Another group of compounds within the present invention includes compounds where $R_{14}$ is any one or more of the following: a bond, H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, phenyl having 1 substituent selected from $R_{20}$ and further having 0–3 substituents independently selected from F, Cl, Br, or I.

Another group of compounds within the present invention includes compounds where each $R_{15}$ is independently any one or more of the following: alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Another group of compounds within the present invention includes compounds where each $R_{16}$ is independently any one or more of the following: cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl.

Another group of compounds within the present invention includes compounds where $R_{17}$ is any one or more of the following: cycloalkyl, halogenated cycloalkyl, substituted cycloalkyl, heterocycloalkyl, halogenated heterocycloalkyl, or substituted heterocycloalkyl.

Another group of compounds within the present invention includes compounds where each $R_{18}$ is independently any one or more of the following: H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$N(R_{11})_2$, —$C(O)R_{11}$, —$NO_2$, —$C(O)N(R_{11})_2$, —CN, —$NR_{11}C(O)R_{11}$, —$S(O)_2N(R_{11})_2$, or —$NR_{11}S(O)_2R_{11}$, F, Cl, Br, or I, or a bond.

Another group of compounds within the present invention includes compounds where $R_4$ is any one or more of the following: —O—$R_5$, —S—$R_5$, —S(O)—$R_5$, —C(O)—$R_5$. Another group of compounds within the present invention includes compounds where $R_5$ is aryl, $R_7$, or $R_9$.

The ω carbon is determined by counting the longest carbon chain of the alkyl-type moiety with the C-1 carbon being the carbon attached to the phenyl ring of the core molecule and the ω carbon being the carbon furthest, e.g., separated by the greatest number of carbon atoms in the chain, from said C-1 carbon.

The core molecule is the Azabicyclo-(carboxamide-type moiety)-phenyl:

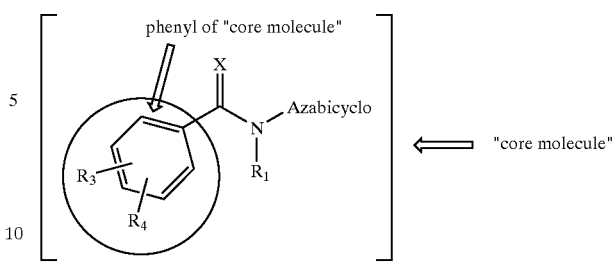

Therefore, when determining the ω carbon, the C-1 carbon will be the carbon attached to the phenyl ring of the core molecule and the ω carbon will be the carbon furthest from said C-1 carbon.

Another group of compounds within the present invention includes compounds where $R_4$ is alkyl substituted on the ω carbon with $R_5$ where said ω carbon is determined by counting the longest carbon chain of the alkyl moiety with the C-1 carbon being the carbon attached to the phenyl ring of the core molecule and the ω carbon being the carbon furthest from said C-1 carbon.

Another group of compounds within the present invention includes compounds where $R_4$ is attached to the phenyl ring of the core molecule at C4 and where $R_3$ is attached to the phenyl ring of the core molecule at a carbon adjacent to the C-4 carbon, including:

One of ordinary skill in the art will recognize that where alkyl, halogenated alkyl, substituted alkyl, alkenyl, halogenated alkenyl, substituted alkenyl, alkynyl, halogenated alkynyl, or substituted alkynyl is allowed, the following, respectively, are also allowed: lower alkyl, lower halogenated alkyl, lower substituted alkyl, lower alkenyl, lower halogenated alkenyl, lower substituted alkenyl, lower alkynyl, lower halogenated alkynyl, or lower substituted alkynyl.

A further embodiment of the present invention includes the compounds of the present invention, pharmaceutical compositions containing the active compounds as the free base or as a pharmaceutically acceptable salt and a pharmaceutically acceptable carrier, and methods to treat the identified diseases.

In another aspect, the invention includes treating a mammal suffering from schizophrenia or psychosis by administering compounds of Formula I in conjunction with antipsychotic drugs (also called anti-psychotic agents). The compounds of the present invention and the antipsychotic drugs can be administered simultaneously or at separate intervals. When administered simultaneously, the compounds of the present invention and the antipsychotic drugs can be incorporated into a single pharmaceutical composition. Alternatively, two separate compositions, i.e., one containing compounds of the present invention and at least one other containing antipsychotic drugs, can be administered simultaneously.

A further embodiment of the present invention provides a method comprising administering a therapeutically effective amount of a compound of the present invention or a pharmaceutical composition contains said compound to the mammal.

The present invention also includes pharmaceutical composition(s) comprising a compound of Formula I or a pharmaceutically acceptable salt thereof and a pharmaceutically acceptable excipient, and optionally anti-psychotic agent(s). The pharmaceutical composition(s) is (are) administered rectally, topically, orally, sublingually, or parenterally for a therapeutically effective interval. The pharmaceutical composition containing the compound of Formula I is administered to deliver the compound in an amount of from about 0.001 to about 100 mg/kg of body weight of said mammal per day. The pharmaceutical composition is also administered to deliver the compound in an amount of from about 0.1 to about 50 mg/kg of body weight of said mammal per day.

The present invention also includes a method to treat using a compound according to Formula I or pharmaceutically acceptable salt thereof, or use of a compound according to Formula I or pharmaceutically acceptable salt thereof to prepare a medicament for treating, a disease or condition, wherein the mammal would receive symptomatic relief from the administration of a therapeutically effective amount of α7 nicotinic acetylcholine receptor agonist.

The present invention also includes a method to treat using a compound according to Formula I or pharmaceutically acceptable salt thereof, or use of a compound according to Formula I or pharmaceutically acceptable salt thereof to prepare a medicament for treating, a disease or condition, wherein the mammal would receive symptomatic relief from the administration of a therapeutically effective amount of α7 nicotinic acetylcholine receptor agonist, wherein the disease, or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

The compounds of Formula I (Azabicyclo is I) have asymmetric center(s) on the quinuclidine ring. The compounds of the present invention include quinuclidines with the 3R configuration or 3S configuration and also includes racemic mixtures, the separate stereoisomers, and compositions of varying degrees of stereochemical purity. For example, and not by limitation, compounds of Formula I include compounds with stereospecificity including:

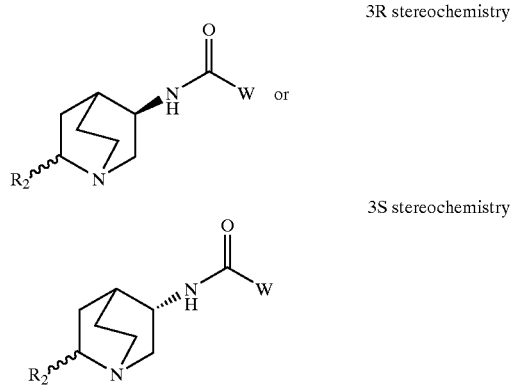

The compounds of Formula I (Azabicyclo is II) have asymmetric center(s) on the [2.2.1] azabicyclic ring at C3 and C4. The scope of this invention includes racemic mixtures of varying degrees of stereochemical purities, the separate stereoisomers, and compositions of varying degrees of stereochemical purities of Formula I being endo-4S, endo-4R, exo-4S, exo-4R:

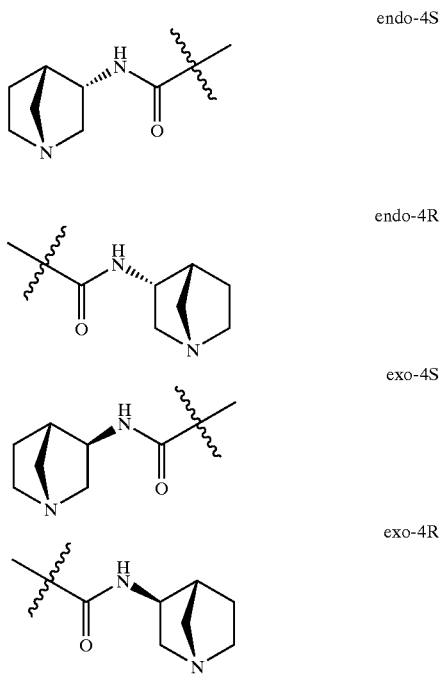

The endo isomer is the isomer where the non-hydrogen substituent at C3 of the [2.2.1] azabicyclic compound is projected toward the larger of the two remaining bridges. The exo isomer is the isomer where the non-hydrogen substituent at C3 of the [2.2.1] azabicyclic compound is projected toward the smaller of the two remaining bridges. Thus, there can be four separate isomers: exo-4(R), exo-4(S), endo-4(R), and endo-4(S).

The compounds of Formula I (Azabicyclo III) have asymmetric center(s) on the [2.2.1] azabicyclic ring at C1, C4 and C5. The scope of this invention includes racemic mixtures of varying degrees of stereochemical purities, the separate stereoisomers, and compositions of varying degrees of stereochemical purities of Formula I being (1R,4R,5S), (1R,4R,5R), (1S,4S,5R), (1S,4S,5S):

endo-1R, 4R, 5R

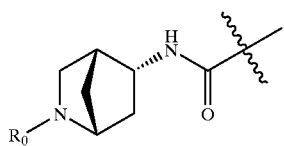

endo-1S, 4S, 5S

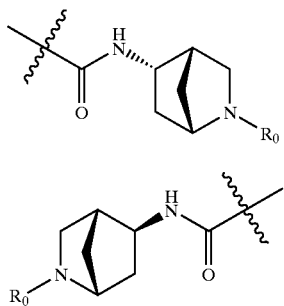

exo-1R, 4R, 5S exo-1S, 4S, 5R

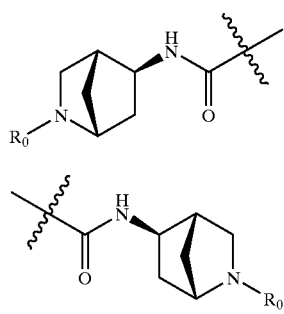

The endo isomer is the isomer where the non-hydrogen substituent at C5 of the [2.2.1] azabicyclic compound is projected toward the larger of the two remaining bridges. The exo isomer is the isomer where the non-hydrogen substituent at C5 of the [2.2.1] azabicyclic compound is projected toward the smaller of the two remaining bridges. Thus, there can be four separate isomers: exo-(1R,4R,5S), exo-(1S,4S,5R), endo-(1S,4S,5S), endo-(1R,4R,5R).

The compounds of Formula I (Azabicyclo IV) have asymmetric center(s) on the [2.2.1] azabicyclic ring at C1, C4 and C6. The scope of this invention includes racemic mixtures of varying degrees of stereochemical purities, the separate stereoisomers, and compositions of varying degrees of stereochemical purities of Formula I being exo-(1S,4R, 6S), exo-(1R,4S,6R), endo-(1S,4R,6R), and endo-(1R,4S, 6S):

endo-1R, 4S, 6S

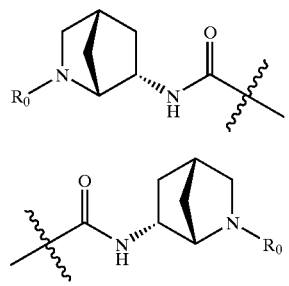

endo-1S, 4R, 6R exo-1R, 4S, 6R

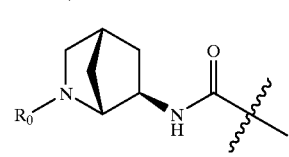

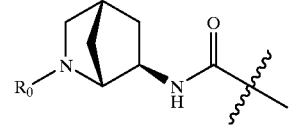

exo-1S, 4R, 6S

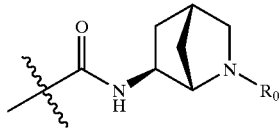

The endo isomer is the isomer where the non-hydrogen substituent at C6 of the [2.2.1] azabicyclic compound is projected toward the larger of the two remaining bridges. The exo isomer is the isomer where the non-hydrogen substituent at C6 of the [2.2.1] azabicyclic compound is projected toward the smaller of the two remaining bridges. Thus, there can be four separate isomers: exo-(1S,4R,6S), exo-(1R,4S,6R), endo-(1S,4R,6R), and endo-(1R,4S,6S).

The compounds of Formula I (Azabicyclo is V) have asymmetric center(s) on the [3.2.1] azabicyclic ring at C3 and C5. The scope of this invention includes racemic mixtures of varying degrees of stereochemical purities, the separate stereoisomers, and compositions of varying degrees of stereochemical purities of Formula I being endo-3S, 5R, endo-3R, 5S, exo-3R, 5R, exo-3S, 5S:

endo-3S, 5R

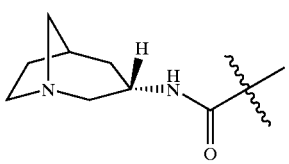

endo-3R, 5S

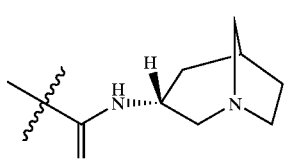

exo-3R, 5R

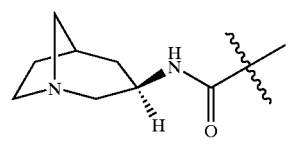

exo-3S, 5S

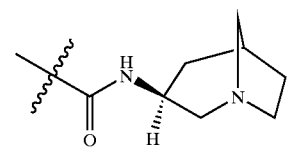

The compounds of Formula I (Azabicyclo is VI) have asymmetric centers on the [3.2.2] azabicyclic ring with one center being at C3 when $R_2$ is absent. The scope of this invention includes racemic mixtures of varying degrees of stereochemical purities, the separate stereoisomers, and compositions of varying degrees of stereochemical purities of Formula I being 3(S) and 3(R):

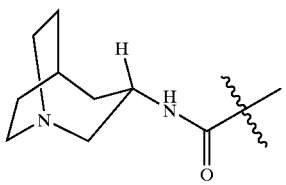

3(S)

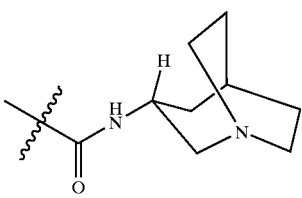

3(R)

The compounds of the present invention having the specified stereochemistry have different levels of activity and that for a given set of values for the variable substituents one isomer may be preferred over the other isomers. Although it is desirable that the stereochemical purity be as high as possible, absolute purity is not required. This invention involves racemic mixtures and compositions of varying degrees of stereochemical purities when the Azabicyclo is substituted with only the amide/thioamide or is substituted with substituents in addition to the amide/thioamide, e.g., $R_2$ is alkyl. When racemic mixtures and compositions are referenced, it is meant racemic mixtures and compositions of varying degrees of stereochemical purities. It is preferred to carry out stereoselective syntheses and/or to subject the reaction product to appropriate purification steps so as to produce substantially enantiomerically pure materials. Suitable stereoselective synthetic procedures for producing enantiomerically pure materials are well known in the art, as are procedures for purifying racemic mixtures into enantiomerically pure fractions.

Stereoselective syntheses and/or subjecting the reaction product to appropriate purification steps produces substantially enantiomerically pure materials. Suitable stereoselective synthetic procedures for producing enantiomerically pure materials are well known in the art, as are procedures for purifying racemic mixtures into enantiomerically pure fractions.

Another embodiment of the compounds of Formula I includes any one or more or combination of the following configurations for compounds:

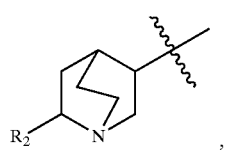

(i)

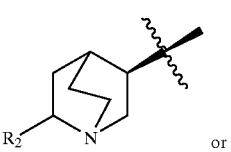

(ii)

or

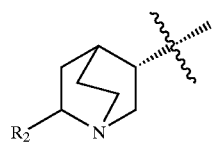

(iii)

where (i) the compound is a mixture of diastereomers, (ii) the compound has the R absolute stereochemistry at C-3 as discussed herein and stereochemistry is unspecified at C-6, or (iii) the compound has the S absolute stereochemistry at C-3 as discussed herein and stereochemistry is unspecified at C-6.

Another embodiment of compounds of Formula I includes any one or more or combination of the following configurations for compounds:

(i)

(ii)

(iii)

, or (iv)

where (i) $R_2$ is absent;

(ii) $R_2$ is alkyl, halogenated alkyl, substituted alkyl, cycloalkyl, or aryl;

(iii) $R_2$ is alkyl, halogenated alkyl, substituted alkyl, cycloalkyl, or aryl; or (iv) the 2.2.1 moiety has the exo-4(S) absolute stereochemistry and $R_2$ has any definition as discussed herein.

Another embodiment of compounds of Formula I includes any one or more or combination of the following configurations for compounds:

(i)

-continued

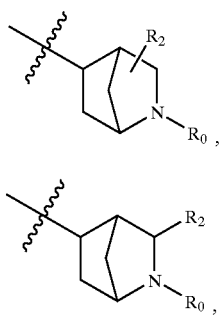

where (i) $R_2$ is absent;

(ii) $R_2$ is F, Cl, Br, I, alkyl, halogenated alkyl, substituted alkyl, cycloalkyl, or aryl; or (iii) $R_2$ is alkyl, halogenated alkyl, substituted alkyl, cycloalkyl, or aryl.

Another embodiment of compounds of Formula I includes any one or more or combination of the following configurations for compounds:

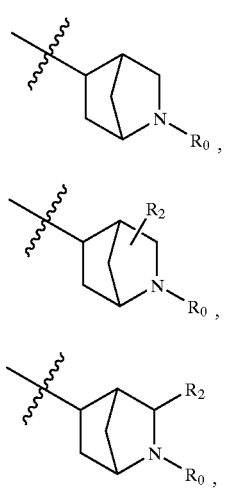

where (i) $R_2$ is absent;

(ii) $R_2$ is F, Cl, Br, I, alkyl, halogenated alkyl, substituted alkyl, cycloalkyl, or aryl; or (iii) $R_2$ is alkyl, halogenated alkyl, substituted alkyl, cycloalkyl, or aryl.

Another embodiment of compounds of Formula I includes any one or more or combination of the following configurations for compounds:

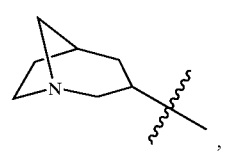

-continued

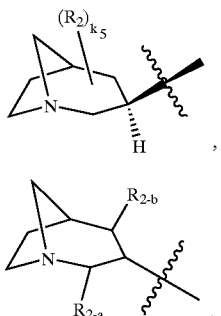

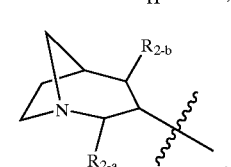

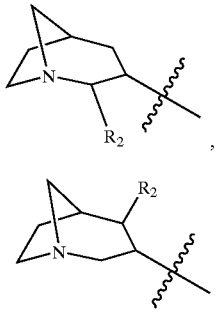

where (i) $R_2$ is absent;

(ii) $R_2$ has any definition as discussed herein and where the Azabicyclo has the absolute stereochemistry of 3R, 5R;

(iii) $k_5$ is 2, where $R_{2\text{-}a}$ is alkyl, halogenated alkyl, substituted alkyl, cycloalkyl, or aryl, and where $R_{2\text{-}b}$ is F, Cl, Br, I, alkyl, halogenated alkyl, substituted alkyl, cycloalkyl, or aryl;

(iv) $k_5$ is 1, where $R_2$ is alkyl, halogenated alkyl, substituted alkyl, cycloalkyl, or aryl; or (v) $k_5$ is 1, where $R_2$ is F, Cl, Br, I, alkyl, halogenated alkyl, substituted alkyl, cycloalkyl, or aryl.

Another embodiment of compounds of Formula I includes any one or more or combination of the following configurations for compounds:

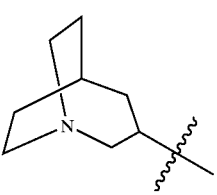

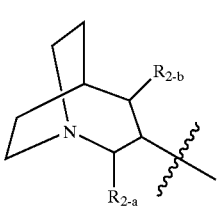

-continued

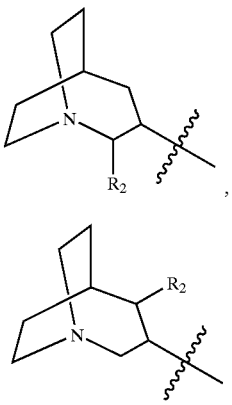

where (i) R₂ is absent;
(ii) k₆ is 2, where each R₂₋ₐ is alkyl, halogenated alkyl, substituted alkyl, cycloalkyl, or aryl and where each R₂₋ᵦ is F, Cl, Br, I, alkyl, halogenated alkyl, substituted alkyl, cycloalkyl, or aryl;
(iii) k₆ is 1, where R₂ is alkyl, halogenated alkyl, substituted alkyl, cycloalkyl, or aryl; or
(iv) k₆ is 1, where R₂ is F, Cl, Br, I, alkyl, halogenated alkyl, substituted alkyl, cycloalkyl, or aryl.

Another aspect of the present invention includes, by representation but not limitation, any compound named or exemplified as a single compound or any combination thereof and pharmaceutically acceptable salt thereof, discussed herein.

The invention also concerns the synthesis of and isolation of stereospecific intermediates and final compounds. Specifically, the present invention concerns the stereoselective synthesis of (3R,5R)-1-azabicyclo[3.2.1]octan-3-amine, or salts thereof. Although there are known procedures for making 1-azabicyclo[3.2.1]octan-3-amine, separation of the different stereoismers as described herein occurs without using a chiral HPLC separation procedure. The procedure within this invention results in an efficient selective synthesis of (3R,5R)-1-azabicyclo[3.2.1]octan-3-amine.

Another aspect of the present invention includes a method for making (3R,5R)-1-azabicyclo[3.2.1]octan-3-amine or salt thereof. One process for producing (3R,5R)-1-azabicyclo[3.2.1]octan-3-amine or a salt thereof, from (3R)-methyl 1-[(S)-1-phenylethyl]pyrrolidine-3-acetate, comprises: the process of producing (5R)-3-oxo-1-[(1S)-1-phenylethyl]-1-azoniabicyclo[3.2.1]octane chloride from (3R)-methyl 1-[(S)-1-phenylethyl]pyrrolidine-3-acetate;

the process of producing (5R)-1-azabicyclo[3.2.1]octan-3-one or a salt thereof from (5R)-3-oxo-1-[(1S)-1-phenylethyl]-1-azoniabicyclo[3.2.1]octane chloride;

and the process of producing (3R,5R)-1-azabicyclo[3.2.1] octan-3-amine or a salt thereof from (5R)-1-azabicyclo[3.2.1]octan-3-one or a salt thereof.

Another process comprises: the process of producing (3R)-methyl 1-[(S)-1-phenylethyl]pyrrolidine-3-acetate from (3R)-1-[(S)-1-phenethyl]-3-(cyanomethyl)pyrrolidine;

the process of producing (5R)-3-oxo-1-[(1S)-1-phenylethyl]-1-azoniabicyclo[3.2.1]octane chloride from (3R)-methyl 1-[(S)-1-phenylethyl]pyrrolidine-3-acetate;

the process of producing (5R)-1-azabicyclo[3.2.1]octan-3-one or a salt thereof from (5R)-3-oxo-1-[(1S)-1-phenylethyl]-1-azoniabicyclo[3.2.1]octane chloride;

and the process of producing (3R,5R)-1-azabicyclo[3.2.1] octan-3-amine or a salt thereof from (5R)-1-azabicyclo [3.2.1]octan-3-one or a salt thereof.

Another process comprises: the process of producing (3S)-1-[(S)-1-phenethyl]-5-oxo-3-pyrrolidine-carboxylic acid from (S)-(–)-α-methyl benzylamine;

the process of isolating (3S)-1-[(S)-1-phenethyl]-5-oxo-3-pyrrolidine-carboxylic acid from a racemic mixture using a precipitating solvent without causing the precipitation of other isomers, where the solvent can include a primary alcohol, including but not limited to methanol;

the process of producing (3S)-1-[(S)-1-phenethyl]-3-(hydroxymethyl)pyrrolidine from (3S)-1-[(S)-1-phenethyl]-5-oxo-3-pyrrolidine-carboxylic acid;

the process of producing (3S)-1-[(S)-1-phenethyl]-3-(chloromethyl)pyrrolidine from (3S)-1-[(S)-1-phenethyl]-3-(hydroxymethyl)pyrrolidine;

the process of producing (3R)-1-[(S)-1-phenethyl]-3-(cyanomethyl)pyrrolidine from (3S)-1-[(S)-1-phenethyl]-3-(chloromethyl)pyrrolidine;

the process of producing (3R)-methyl 1-[(S)-1-phenylethyl]pyrrolidine-3-acetate from (3R)-1-[(S)-1-phenethyl]-3-(cyanomethyl)pyrrolidine;

the process of producing (5R)-3-oxo-1-[(1S)-1-phenylethyl]-1-azoniabicyclo[3.2.1]octane chloride from (3R)-methyl 1-[(S)-1-phenylethyl]pyrrolidine-3-acetate;

the process of producing (5R)-1-azabicyclo[3.2.1]octan-3-one or salt thereof from (5R)-3-oxo-1-[(1S)-1-phenylethyl]-1-azoniabicyclo[3.2.1]octane chloride;

and the process of producing (3R,5R)-1-azabicyclo[3.2.1] octan-3-amine or salt thereof from (5R)-1-azabicyclo[3.2.1] octan-3-one or salt thereof.

Another process comprises: the process of producing (3S)-1-[(S)-1-phenethyl]-5-oxo-3-pyrrolidine-carboxylic acid from (S)-(–)-α-methyl benzylamine;

the process of producing (3S)-1-[(S)-1-phenethyl]-3-(hydroxymethyl)pyrrolidine from (3S)-1-[(S)-1-phenethyl]-5-oxo-3-pyrrolidine-carboxylic acid;

the process of producing (3S)-1-[(S)-1-phenethyl]-3-(chloromethyl)pyrrolidine from (3S)-1-[(S)-1-phenethyl]-3-(hydroxymethyl)pyrrolidine;

the process of producing (3R)-1-[(S)-1-phenethyl]-3-(cyanomethyl)pyrrolidine from (3S)-1-[(S)-1-phenethyl]-3-(chloromethyl)pyrrolidine;

the process of producing (3R)-methyl 1-[(S)-1-phenylethyl]pyrrolidine-3-acetate from (3R)-1-[(S)-1-phenethyl]-3-(cyanomethyl)pyrrolidine;

the process of producing (5R)-3-oxo-1-[(1S)-1-phenylethyl]-1-azoniabicyclo[3.2.1]octane chloride from (3R)-methyl 1-[(S)-1-phenylethyl]pyrrolidine-3-acetate;

the process of producing (5R)-1-azabicyclo[3.2.1]octan-3-one or salt thereof from (5R)-3-oxo-1-[(1S)-1-phenylethyl]-1-azoniabicyclo[3.2.1]octane chloride;

and the process of producing (3R,5R)-1-azabicyclo[3.2.1] octan-3-amine or salt thereof from (5R)-1-azabicyclo[3.2.1] octan-3-one or salt thereof.

Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

DETAILED DESCRIPTION OF THE INVENTION

Surprisingly, we have found that compounds of Formula I:

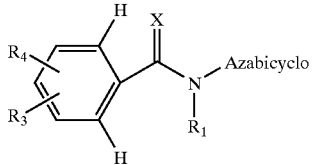

Formula I wherein X is O or S;
Azabicyclo is

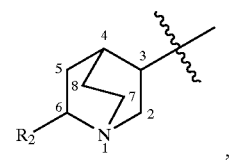

I

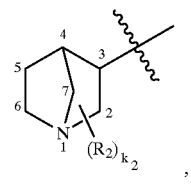

II

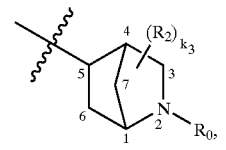

III

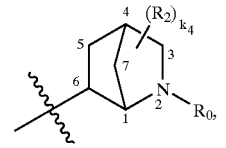

IV

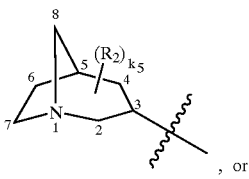

V

, or

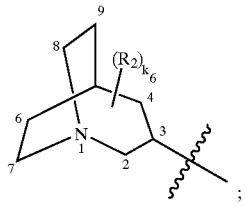

VI

;

$R_0$ is H, lower alkyl, lower substituted alkyl, or lower halogenated alkyl;

$R_1$ is independently H, alkyl, cycloalkyl, halogenated alkyl, and aryl;

$R_2$ is F, Cl, Br, I, alkyl, halogenated alkyl, substituted alkyl, cycloalkyl, or aryl, provided that when Azabicyclo is I, $R_2$ is alkyl, halogenated alkyl, substituted alkyl, cycloalkyl, or aryl, provided that $R_2$ is absent when any of $k_2$, $k_3$, $k_4$, $k_5$, or $k_6$ is 0;

$k_2$ is 0 or 1;
$k_3$ is 0 or 1;
$k_4$ is 0 or 1;
$k_5$ is 0, 1, or 2;
$k_6$ is 0, 1, or 2;

$R_3$ is H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, aryl, $R_7$, $R_9$, —$OR_8$, —$OR_{17}$, —$SR_8$, —$S(O)_2R_8$, —$S(O)R_8$, —$OS(O)_2R_8$, —$NR_8R_8$, —$NR_{15}R_{15}$, —$C(O)R_8$, —$C(O)R_{16}$, —$C(S)R_8$, —$C(O)OR_8$, —CN, —$C(O)NR_8R_8$, —$C(O)NR_{15}R_{15}$, —$NR_8C(O)R_8$, —$S(O)_2NR_8R_8$, —$NR_8S(O)_2R_8$, —$NO_2$, —$N(R_8)C(O)NR_8R_8$, —$N(H)C(O)N(H)R_8$, substituted alkyl, substituted alkenyl, substituted alkynyl, substituted cycloalkyl, substituted heterocycloalkyl, phenyl, phenyl having 1–4 substituents independently selected from F, Cl, Br, I and $R_{21}$, naphthyl, or naphthyl having 1–4 substituents independently selected from F, Cl, Br, I, $R_{21}$;

$R_4$ is —O—$R_5$, —S—$R_5$, —S(O)—$R_5$, —C(O)—$R_5$, or alkyl substituted on the ω carbon with $R_5$ where said ω carbon is determined by counting the longest carbon chain of the alkyl moiety with the C-1 carbon being the carbon attached to the phenyl ring of the core molecule and the ω carbon being the carbon furthest from said C-1 carbon;

$R_5$ is aryl, $R_7$, or $R_9$;

$R_7$ is 5-membered heteroaromatic mono-cyclic moieties containing within the ring 1–3 heteroatoms independently selected from —O—, =N—, —N($R_{14}$)—, and —S—, and having 0–1 substituent selected from $R_{12}$ and 0–3 substituents independently selected from F, Cl, Br, or I, or $R_7$ is a 9-membered fused-ring moiety having a 6-membered ring fused to a 5-membered ring and having the formula:

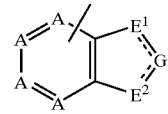

wherein each A is independently $CR_{18}$ or N, provided that only up to one A is N, $E^1$ and $E^2$ are independently selected from $CR_{18}$, O, S, or $NR_{14}$, and G is $CR_{18}$, provided that $R_{18}$ or $R_{14}$ of $E^1$, $E^2$, and G can be a bond when - - - forms a double bond and further provided that $R_{18}$ or $R_{14}$ can be a bond for bonding $R_7$ to a moiety to which it is attached;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from $R_{12}$ and 0–3 substituent(s) independently selected from F, Cl, Br, or I, or $R_9$ is 10-membered heteroaromatic bi-cyclic moieties containing within one or both rings 1–3 heteroatoms selected from =N—, including quinolinyl or isoquinolinyl, each 10-membered fused-ring moiety having 0–1 substituent selected from $R_{12}$ and 0–3 substituent(s) independently selected from F, Cl, Br, or I and having a bond for bonding $R_9$ to a moiety to which it is attached where valency allows;

Each $R_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or phenyl having 1 substituent selected from $R_{20}$ and further having 0–3 substituents independently selected from F, Cl, Br, or I;

Each $R_{11}$ is independently H, alkyl, cycloalkyl, heterocycloalkyl, halogenated alkyl, halogenated cycloalkyl, or halogenated heterocycloalkyl;

$R_{12}$ is —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_1$;

$R_{13}$ is —$OR_{11}$, —$SR_{11}$, —$NR_{11}R_{11}$, —$C(O)R_{11}$, —$C(O)NR_{11}R_{11}$, —CN, —$CF_3$, —$NR_{11}C(O)R_{11}$, —$S(O)_2NR_{11}R_{11}$, —$NR_{11}S(O)_2R_{11}$, or —$NO_2$;

$R_{14}$ is a bond, H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, phenyl having 1 substituent selected from $R_{20}$ and further having 0–3 substituents independently selected from F, Cl, Br, or I;

Each $R_{15}$ is independently alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Each $R_{16}$ is independently cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Each $R_{17}$ is independently cycloalkyl, halogenated cycloalkyl, substituted cycloalkyl, heterocycloalkyl, halogenated heterocycloalkyl, or substituted heterocycloalkyl;

Each $R_{18}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$N(R_{11})_2$, —$C(O)R_{11}$, —$NO_2$, —$C(O)N(R_{11})_2$, —CN, —$NR_{11}C(O)R_{11}$, —$S(O)_2N(R_{11})_2$, or —$NR_{11}S(O)_2R_{11}$, F, Cl, Br, or I, or a bond;

$R_{19}$ is H, alkyl, halogenated alkyl, substituted alkyl, cycloalkyl, halogenated cycloalkyl, substituted cycloalkyl, phenyl, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —$OR_{11}$, —$SR_{11}$, —$N(R_{11})_2$, —$C(O)R_{11}$, —$C(O)N(R_{11})_2$, —CN, —$NR_{11}C(O)R_{11}$, —$S(O)_2N(R_{11})_2$, —$NR_{11}S(O)_2R_{11}$, —$NO_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or $R_{13}$;

Each $R_{21}$ is independently alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or phenyl having 1 substituent selected from $R_{20}$ and further having 0–3 substituents independently selected from F, Cl, Br, or I;

Aryl is phenyl, substituted phenyl, naphthyl, or substituted naphthyl;

Substituted phenyl is a phenyl either having 1–4 substituents independently selected from F, Cl, Br, or I, or having 1 substituent selected from $R_{12}$ and 0–3 substituents independently selected from F, Cl, Br, or I;

Substituted naphthyl is a naphthalene moiety either having 1–4 substituents independently selected from F, Cl, Br, or I, or having 1 substituent selected from $R_{12}$ and 0–3 substituents independently selected from F, Cl, Br, or I, where the substitution can be independently on either only one ring or both rings of said naphthalene moiety;

Alkyl is both straight- and branched-chain moieties having from 1–6 carbon atoms;

Lower alkyl is both straight- and branched-chain moieties having from 1–4 carbon atoms;

Halogenated alkyl is an alkyl moiety having from 1–6 carbon atoms and having 1 to (2n+1) substituent(s) independently selected from F, Cl, Br, or I where n is the maximum number of carbon atoms in the moiety;

Lower halogenated alkyl is an alkyl moiety having from 1–4 carbon atoms and having 1 to (2n+1) substituent(s) independently selected from F, Cl, Br, or I where n is the maximum number of carbon atoms in the moiety;

Substituted alkyl is an alkyl moiety from 1–6 carbon atoms and having 0–3 substituents independently selected from F, Cl, Br, or I and further having 1 substituent selected from —$OR_{10}$, —$SR_{10}$, —$N(R_{10})_2$, —$C(O)R_{10}$, —$C(O)N(R_{10})_2$, —CN, —$NR_{10}C(O)R_{10}$, —$S(O)_2N(R_{10})_2$, —$NR_{10}S(O)_2R_{10}$, —$NO_2$, $R_7$, $R_9$, phenyl, or phenyl having 1 substituent selected from $R_{20}$ and further having 0–3 substituents independently selected from F, Cl, Br, or I;

Lower substituted alkyl is lower alkyl having 0–3 substituents independently selected from F, Cl, Br, or I, and further having 1 substituent selected from —$OR_{10}$, —$SR_{10}$, —$N(R_{10})_2$, —$C(O)R_{10}$, —$C(O)N(R_{10})_2$, —CN, —$NR_{10}C(O)R_{10}$, —$S(O)_2N(R_{10})_2$, —$NR_{10}S(O)_2R_{10}$, —$NO_2$, or phenyl, wherein each $R_{10}$ is independently H, lower alkyl, cycloalkyl, heterocycloalkyl, or phenyl, wherein any lower alkyl, cycloalkyl, heterocycloalkyl, or phenyl is optionally substituted with up to two halogens and up to one other substituent independently selected from —$OR_{11}$, —$SR_{11}$, —$N(R_{11})_2$, —$C(O)R_{11}$, —$C(O)N(R_{11})_2$, —CN, —$CF_3$, —$NR_{11}C(O)R_{11}$, —$S(O)_2N(R_{11})_2$, —$NR_{11}S(O)_2R_{11}$, or —$NO_2$, and wherein each $R_{11}$ is independently H, lower alkyl, lower cycloalkyl, heterocycloalkyl, lower halogenated alkyl, lower halogenated cycloalkyl, or halogenated heterocycloalkyl;

Alkenyl is straight- and branched-chain moieties having from 2–6 carbon atoms and having at least one carbon-carbon double bond;

Lower alkenyl is straight- and branched-chain moieties having from 2–4 carbon atoms and having at least one carbon-carbon double bond;

Halogenated alkenyl is an unsaturated alkenyl moiety having from 2–6 carbon atoms and having 1 to (2n−1) substituent(s) independently selected from F, Cl, Br, or I where n is the maximum number of carbon atoms in the moiety;

Lower halogenated alkenyl is an unsaturated alkenyl moiety having from 2–4 carbon atoms and having 1 to (2n−1) substituent(s) independently selected from F, Cl, Br, or I where n is the maximum number of carbon atoms in the moiety;

Substituted alkenyl is an unsaturated alkenyl moiety having from 2–4 carbon atoms and having 0–3 substituents independently selected from F, or Cl, and further having 1 substituent selected from $R_7$, $R_9$, —$OR_{10}$, —$SR_{10}$, —N($R_{10}$)$_2$, —C(O)$R_{10}$, —C(O)N($R_{10}$)$_2$, —$NR_{10}$C(O)$R_{10}$, —S(O)$_2$N($R_{10}$)$_2$, —$NR_{10}$S(O)$_2R_{10}$, —CN, phenyl, or phenyl having 1 substituent selected from $R_{20}$ and further having 0–3 substituents independently selected from F, Cl, Br, or I;

Lower substituted alkenyl is lower alkenyl having 0–3 substituents independently selected from F, or Cl, and further having 1 substituent selected from —$OR_{10}$, —$SR_{10}$, —N($R_{10}$)$_2$, —C(O)$R_{10}$, —C(O)N($R_{10}$)$_2$, —CN, —$NR_{10}$C(O)$R_{10}$, —S(O)$_2$N($R_{10}$)$_2$, —$NR_{10}$S(O)$_2R_{10}$, —$NO_2$, or phenyl, wherein each $R_{10}$ is independently H, lower alkyl, cycloalkyl, heterocycloalkyl, or phenyl, wherein any lower alkyl, cycloalkyl, heterocycloalkyl, or phenyl is optionally substituted with up to two halogens and up to one other substituent independently selected from —$OR_{11}$, —$SR_{11}$, —N($R_{11}$)$_2$, —C(O)$R_{11}$, —C(O)N($R_{11}$)$_2$, —CN, —$CF_3$, —$NR_{11}$C(O)$R_{11}$, —S(O)$_2$N($R_{11}$)$_2$, —$NR_{11}$S(O)$_2R_{11}$, or —$NO_2$, and wherein each $R_{11}$ is independently H, lower alkyl, lower cycloalkyl, heterocycloalkyl, lower halogenated alkyl, lower halogenated cycloalkyl, or halogenated heterocycloalkyl;

Alkynyl is straight- and branched-chained moieties having from 2–6 carbon atoms and having at least one carbon-carbon triple bond;

Lower alkynyl is straight- and branched-chained moieties having from 2–4 carbon atoms and having at least one carbon-carbon triple bond;

Halogenated alkynyl is an unsaturated alkynyl moiety having from 3–6 carbon atoms and having 1 to (2n–3) substituent(s) independently selected from F, Cl, Br, or I where n is the maximum number of carbon atoms in the moiety;

Lower halogenated alkynyl is an unsaturated alkynyl moiety having from 3–4 carbon atoms and having 1 to (2n–3) substituent(s) independently selected from F, Cl, Br, or I where n is the maximum number of carbon atoms in the moiety;

Substituted alkynyl is an unsaturated alkynyl moiety having from 3–6 carbon atoms and having 0–3 substituents independently selected from F, or Cl, and further having 1 substituent selected from —$R_7$, —$R_9$, —$OR_{10}$, —$SR_{10}$, —N($R_{10}$)$_2$, —C(O)$R_{10}$, —C(O)N($R_{10}$)$_2$, —$NR_{10}$C(O)$R_{10}$, —S(O)$_2$N($R_{10}$)$_2$, —$NR_{10}$S(O)$_2R_{10}$, —CN, phenyl, or phenyl having 1 substituent selected from $R_{20}$ and further having 0–3 substituents independently selected from F, Cl, Br, or I;

Lower substituted alkynyl is lower alkynyl having 0–3 substituents independently selected from F, or Cl, and further having 1 substituent selected from —$OR_{10}$, —$SR_{10}$, —N($R_{10}$)$_2$, —C(O)$R_{10}$, —C(O)N($R_{10}$)$_2$, —CN, —$NR_{10}$C(O)$R_{10}$, —S(O)$_2$N($R_{10}$)$_2$, —$NR_{10}$S(O)$_2R_{10}$, —$NO_2$, or phenyl, wherein each $R_{10}$ is independently H, lower alkyl, cycloalkyl, heterocycloalkyl, or phenyl, wherein any lower alkyl, cycloalkyl, heterocycloalkyl, or phenyl is optionally substituted with up to two halogens and up to one other substituent independently selected from —$OR_{11}$, —$SR_{11}$, —N($R_{11}$)$_2$, —C(O)$R_{11}$, —C(O)N($R_{11}$)$_2$, —CN, —$CF_3$, —$NR_{11}$C(O)$R_{11}$, —S(O)$_2$N($R_{11}$)$_2$, —$NR_{11}$S(O)$_2R_{11}$, or —$NO_2$, and wherein each $R_{11}$ is independently H, lower alkyl, lower cycloalkyl, heterocycloalkyl, lower halogenated alkyl, lower halogenated cycloalkyl, or halogenated heterocycloalkyl;

Cycloalkyl is a cyclic alkyl moiety having from 3–6 carbon atoms;

Halogenated cycloalkyl is a cyclic moiety having from 3–6 carbon atoms and having 1–4 substituents independently selected from F, or Cl;

Substituted cycloalkyl is a cyclic moiety having from 3–6 carbon atoms and having 0–3 substituents independently selected from F, or Cl, and further having 1 substituent selected from —$OR_{10}$, —$SR_{10}$, —N($R_{10}$)$_2$, —C(O)$R_{10}$, —CN, —C(O)N($R_{10}$)$_2$, —$NR_{10}$C(O)$R_{10}$, —S(O)$_2$N($R_{10}$)$_2$, —$NR_{10}$S(O)$_2R_{10}$, —$NO_2$, phenyl, or phenyl having 1 substituent selected from $R_{20}$ and further having 0–3 substituents independently selected from F, Cl, Br, or I;

Heterocycloalkyl is a cyclic moiety having 4–7 atoms with 1–2 atoms within the ring being —S—, —N($R_{19}$)—, or —O—;

Halogenated heterocycloalkyl is a cyclic moiety having from 4–7 atoms with 1–2 atoms within the ring being —S—, —N($R_{19}$)—, or —O—, and having 1–4 substituents independently selected from F, or Cl;

Substituted heterocycloalkyl is a cyclic moiety having from 4–7 atoms with 1–2 atoms within the ring being —S—, —N($R_{19}$)—, or —O— and having 0–3 substituents independently selected from F, or Cl, and further having 1 substituent selected from —$OR_{10}$, —$SR_{10}$, —N($R_{10}$)$_2$, —C(O)$R_{10}$, —C(O)N($R_{10}$)$_2$, —CN, —$NR_{10}$C(O)$R_{10}$, —$NO_2$, —S(O)$_2$N($R_{10}$)$_2$, —$NR_{10}$S(O)$_2R_{10}$, phenyl, or phenyl having 1 substituent selected from $R_{20}$ and further having 0–3 substituents independently selected from F, Cl, Br, or I;

or pharmaceutical composition, pharmaceutically acceptable salt, racemic mixture, or pure enantiomer thereof useful to treat any one of or combination of cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulimia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

In another aspect, the invention includes methods of treating a mammal suffering from schizophrenia or psychosis by administering compounds of Formula I in conjunction with antipsychotic drugs. The compounds of Formula I and the antipsychotic drugs can be administered simultaneously or at separate intervals. When administered simultaneously the compounds of Formula I and the antipsychotic drugs can be incorporated into a single pharmaceutical composition. Alternatively, two separate compositions, i.e., one containing compounds of Formula I and the other containing antipsychotic drugs, can be administered simultaneously.

The present invention also includes the intermediates, the processes to make them and the compounds of the present invention, pharmaceutical compositions containing the active compounds, and methods to treat the identified diseases.

Abbreviations which are well known to one of ordinary skill in the art may be used (e.g., "Ph" for phenyl, "Me" for methyl, "Et" for ethyl, "h" or "hr" for hour or hours, min for minute or minutes, and "rt" or "RT" for room temperature).

All temperatures are in degrees Centigrade.

Room temperature is within the range of 15–25 degrees Celsius.

AChR refers to acetylcholine receptor.

nAChR refers to nicotinic acetylcholine receptor.

Pre-senile dementia is also known as mild cognitive impairment.

$5HT_3R$ refers to the serotonin-type 3 receptor.

α-btx refers to α-bungarotoxin.

FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).

TLC refers to thin-layer chromatography.

HPLC refers to high pressure liquid chromatography.

MeOH refers to methanol.

EtOH refers to ethanol.

IPA refers to isopropyl alcohol.

THF refers to tetrahydrofuran.

DMSO refers to dimethylsulfoxide.

DMF refers to N,N-dimethylformamide.

EtOAc refers to ethyl acetate.

TMS refers to tetramethylsilane.

TEA refers to triethylamine.

DIEA refers to N,N-diisopropylethylamine.

MLA refers to methyllycaconitine.

Ether refers to diethyl ether.

HATU refers to O-(7-azabenzotriazol-1-yl)-N,N,N',N'-tetramethyluronium hexafluorophosphate.

CDI refers to carbonyl diimidazole.

NMO refers to N-methylmorpholine-N-oxide.

TPAP refers to tetrapropylammonium perruthenate.

Halogen is F, Cl, Br, or I.

$Na_2SO_4$ refers to sodium sulfate.

$K_2CO_3$ refers to potassium carbonate.

$MgSO_4$ refers to magnesium sulfate.

When $Na_2SO_4$, $K_2CO_3$, or $MgSO_4$ is used as a drying agent, it is anhydrous.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to six carbon atoms.

Non-inclusive examples of heteroaryl compounds that fall within the definition of $R_7$ and $R_9$ include, but are not limited to, thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl.

Non-inclusive examples of heterocycloalkyl include, but are not limited to, tetrahydrofurano, tetrahydropyrano, morpholino, pyrrolidino, piperidino, piperazine, azetidino, azetidinono, oxindolo, dihydroimidazolo, and pyrrolidinono Mammal denotes human and other mammals.

Brine refers to an aqueous saturated sodium chloride solution.

Equ means molar equivalents.

IR refers to infrared spectroscopy.

Lv refers to leaving groups within a molecule, including Cl, OH, or mixed anhydride.

NMR refers to nuclear (proton) magnetic resonance spectroscopy, chemical shifts are reported in ppm (δ) downfield from TMS.

MS refers to mass spectrometry expressed as m/e or mass/charge unit. HRMS refers to high resolution mass spectrometry expressed as m/e or mass/charge unit. $[M+H]^+$ refers to an ion composed of the parent plus a proton. $[M-H]^-$ refers to an ion composed of the parent minus a proton. $[M+Na]^+$ refers to an ion composed of the parent plus a sodium ion. $[M+K]^+$ refers to an ion composed of the parent plus a potassium ion. EI refers to electron impact. ESI refers to electrospray ionization. CI refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001 to 100 mg/kg/day for an adult, preferably in the range of about 0.1 to 50 mg/kg/day for an adult. A total daily dose of about 1 to 1000 mg of active ingredient may be appropriate for an adult. The daily dose can be administered in one to four doses per day.

In addition to the compound(s) of Formula I, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, EtOH, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence homology with α7 nAChR but functionally the two ligand-gated ion channels are very different. For example, α7 nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the α7 nAChR and $5HT_3R$ proteins have some degree of homology, but function very differently. Indeed the pharmacology of the channels is very different. For example, Ondansetron, a highly selective $5HT_3R$ antagonist, has little activity at the α7 nAChR. The converse is also true. For example, GTS-21, a highly selective α7 nAChR agonist, has little activity at the $5HT_3R$.

α7 nAChR is a ligand-gated $Ca^{++}$ channel formed by a homopentamer of α7 subunits. Previous studies have established that α-bungarotoxin ((α-btx) binds selectively to this homopetameric, α7 nAChR subtype, and that α7 nAChR has a high affinity binding site for both α-btx and methyllycaconitine (MLA). α7 nAChR is expressed at high levels in the hippocampus, ventral tegmental area and ascending cholinergic projections from nucleus basilis to thalamocortical areas. α7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharmacology*, 108:417–31, 1992; Levin, E. D. and Simon B. B., *Psychopharmacology*, 138:217–30, 1998). For example, it is well known that nicotine increases cognition and attention in humans. ABT-418, a compound that activates α4β2 and α7 nAChR, improves cognition and attention in clinical trials of Alzheimer's disease and attention-deficit disorders (Potter, A. et. al., *Psychopharmacology* (Berl)., 142(4):334–42, March 1999; Wilens, T. E. et. al., *Am. J. Psychiatry*, 156(12):1931–7, December 1999). It is also clear that nicotine and selective but weak α7 nAChR agonists increase cognition and attention in rodents and non-human primates.

Schizophrenia is a complex multifactorial illness caused by genetic and non-genetic risk factors that produce a constellation of positive and negative symptoms. The positive symptoms include delusions and hallucinations and the negative symptoms include deficits in affect, attention, cognition and information processing. No single biological element has emerged as a dominant pathogenic factor in this disease. Indeed, it is likely that schizophrenia is a syndrome that is produced by the combination of many low penetrance risk factors. Pharmacological studies established that dopamine receptor antagonists are efficacious in treating the overt psychotic features (positive symptoms) of schizophrenia such as hallucinations and delusions. Clozapine, an "a typical" antipsychotic drug, is novel because it is effective in treating both the positive and some of the negative symptoms of this disease. Clozapine's utility as a drug is greatly limited because continued use leads to an increased risk of agranulocytosis and seizure. No other antipsychotic drug is effective in treating the negative symptoms of schizophrenia. This is significant because the restoration of cognitive functioning is the best predictor of a successful clinical and functional outcome of schizophrenic patients (Green, M. F., *Am J Psychiatry*, 153:321–30, 1996). By extension, it is clear that better drugs are needed to treat the cognitive disorders of schizophrenia in order to restore a better state of mental health to patients with this disorder.

One aspect of the cognitive deficit of schizophrenia can be measured by using the auditory event-related potential (P50) test of sensory gating. In this test, electroencephographic (EEG) recordings of neuronal activity of the hippocampus are used to measure the subject's response to a series of auditory "clicks" (Adler, L. E. et. al., *Biol. Psychiatry*, 46:8–18, 1999). Normal individuals respond to the first click with greater degree than to the second click. In general, schizophrenics and schizotypal patients respond to both clicks nearly the same (Cullum, C. M. et. al., *Schizophr. Res.,* 10:131–41, 1993). These data reflect a schizophrenic's inability to "filter" or ignore unimportant information. The sensory gating deficit appears to be one of the key pathological features of this disease (Cadenhead, K. S. et. al., *Am. J. Psychiatry,* 157:55–9, 2000). Multiple studies show that nicotine normalizes the sensory deficit of schizophrenia (Adler, L. E. et. al., *Am. J. Psychiatry,* 150:1856–61, 1993). Pharmacological studies indicate that nicotine's effect on sensory gating is via the α7 nAChR (Adler, L. E. et. al., *Schizophr. Bull.,* 24:189–202, 1998). Indeed, the biochemical data indicate that schizophrenics have 50% fewer of α7 nAChR receptors in the hippocampus, thus giving a rationale to partial loss of α7 nAChR functionality (Freedman, R. et. al., *Biol. Psychiatry,* 38:22–33, 1995). Interestingly, genetic data indicate that a polymorphism in the promoter region of the α7 nAChR gene is strongly associated with the sensory gating deficit in schizophrenia (Freedman, R. et. al., *Proc. Nat'l Acad. Sci. USA,* 94(2):587–92, 1997; Myles-Worsley, M. et. al., *Am. J. Med. Genet,* 88(5):544–50, 1999). To date, no mutation in the coding region of the α7 nAChR has been identified. Thus, schizophrenics express the same α7 nAChR as non-schizophrenics.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of α7 nAChR and $5HT_3R$. To conduct such an assay, one uses cell lines that expressed functional forms of the α7 nAChR using the α7/5-$HT_3$ channel as the drug target and cell lines that expressed functional $5HT_3R$. In both cases, the ligand-gated ion channel was expressed in SH-EP1 cells. Both ion channels can produce robust signal in the FLIPR assay.

The compounds of the present invention are α7 nAChR agonists and may be used to treat a wide variety of diseases. For example, they may be used in treating schizophrenia, or psychosis.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Psychosis is a mental disorder characterized by gross impairment in the patient's perception of reality. The patient may suffer from delusions, and hallucinations, and may be incoherent in speech. His behavior may be agitated and is often incomprehensible to those around him. In the past, the term psychosis has been applied to many conditions that do not meet the stricter definition given above. For example, mood disorders were named as psychoses.

There are a variety of antipsychotic drugs. The conventional antipsychotic drugs include Chlorpromazine, Fluphenazine, Haloperidol, Loxapine, Mesoridazine, Molindone, Perphenazine, Pimozide, Thioridazine, Thiothixene, and Trifluoperazine. These drugs all have an affinity for the dopamine 2 receptor.

These conventional antipsychotic drugs have several side effects, including sedation, weight gain, tremors, elevated prolactin levels, akathisia (motor restlessness), dystonia and muscle stiffness. These drugs may also cause tardive dyskinesia. Unfortunately, only about 70% of patients with schizophrenia respond to conventional antipsychotic drugs. For these patients, a typical antipsychotic drugs are available.

A typical antipsychotic drugs generally are able to alleviate positive symptoms of psychosis while also improving negative symptoms of the psychosis to a greater degree than conventional antipsychotics. These drugs may improve neurocognitive deficits. Extrapyramidal (motor) side effects are not as likely to occur with the a typical antipsychotic drugs, and thus, these a typical antipsychotic drugs have a lower risk of producing tardive dyskinesia. Finally these a typical antipsychotic drugs cause little or no elevation of prolactin. Unfortunately, these drugs are not free of side effects. Although these drugs each produce different side effects, as a group the side effects include: agranulocytosis; increased risk of seizures, weight gain, somnolence, dizziness, tachycardia, decreased ejaculatory volume, and mild prolongation of QTc interval.

In a combination therapy to treat multiple symptoms of diseases such as schizophrenia, the compounds of Formula I and the anti-psychotic drugs can be administered simultaneously or at separate intervals. When administered simultaneously the compounds of Formula I and the antipsychotic drugs can be incorporated into a single pharmaceutical composition, e.g., a pharmaceutical combination therapy composition. Alternatively, two separate compositions, i.e., one containing compounds of Formula I and the other containing anti-psychotic drugs, can be administered simultaneously. Examples of anti-psychotic drugs, in addition to those listed above, include, but are not limited to, Thorazine, Mellaril, Trilafon, Navane, Stelazine, Permitil, Prolixin, Risperdal, Zyprexa, Seroquel, ZELDOX, Acetophenazine, Carphenazine, Chlorprothixene, Droperidol, Loxapine, Mesoridazine, Molindone, Ondansetron, Pimozide, Prochlorperazine, and Promazine.

A pharmaceutical combination therapy composition can include therapeutically effective amounts of the compounds of Formula I and a therapeutically effective amount of anti-psychotic drugs. These compositions may be formulated with common excipients, diluents or carriers, and compressed into tablets, or formulated elixirs or solutions for convenient oral administration or administered by intramuscular intravenous routes. The compounds can be administered rectally, topically, orally, sublingually, or parenterally and maybe formulated as sustained relief dosage forms and the like.

When separately administered, therapeutically effective amounts of compositions containing compounds of Formula I and anti-psychotic drugs are administered on a different schedule. One may be administered before the other as long as the time between the two administrations falls within a therapeutically effective interval. A therapeutically effective interval is a period of time beginning when one of either (a) the compounds of Formula I, or (b) the anti-psychotic drugs is administered to a human and ending at the limit of the beneficial effect in the treatment of schizophrenia or psychosis of the combination of (a) and (b). The methods of administration of the compounds of Formula I and the anti-psychotic drugs may vary. Thus, either agent or both agents may be administered rectally, topically, orally, sublingually, or parenterally.

As discussed, the compounds of the present invention are α7 nAChR agonists. Therefore, as another aspect of the present invention, the compounds of the present invention may be used to treat a variety of diseases including cognitive and attention deficit symptoms of Alzheimer's, neurodegeneration associated with diseases such as Alzheimer's disease, pre-senile dementia (also known as mild cognitive impairment), and senile dementia.

Alzheimer's disease has many aspects, including cognitive and attention deficits. Currently, these deficits are treated with cholinesterase inhibitors. These inhibitors slow the break down of acetylcholine, and thereby provide a general nonspecific increase in the activity of the cholinergic nervous system. Since the drugs are nonspecific, they have a wide variety of side effects. Thus, there is a need for a drug that stimulates a portion of the cholinergic pathways and thereby provides improvement in the cognitive and attention deficits associated with Alzheimer's disease without the side effects created by nonspecific stimulation of the cholinergic pathways.

Neurodegeneration is a common problem associated with diseases such as Alzheimer's disease. While the current drugs treat some of the symptoms of this disease, they do not control the underlying pathology of the disease. Accordingly, it would be desirable to provide a drug that can slow the progress of Alzheimer's disease.

Pre-senile dementia (mild cognitive impairment) concerns memory impairment rather than attention deficit problems and otherwise unimpaired cognitive functioning. Mild cognitive impairment is distinguished from senile dementia in that mild cognitive impairment involves a more persistent and troublesome problem of memory loss for the age of the patient. There currently is no medication specifically identified for treatment of mild cognitive impairment, due somewhat to the newness of identifying the disease. Therefore, there is a need for a drug to treat the memory problems associated with mild cognitive impairment.

Senile dementia is not a single disease state. However, the conditions classified under this name frequently include cognitive and attention deficits. Generally, these deficits are not treated. Accordingly, there is a need for a drug that provides improvement in the cognitive and attention deficits associated with senile dementia.

As discussed, the compounds of the present invention are α7 nAChR agonists. Therefore, yet other diseases to be treated with compounds of the present invention include treating the cognitive and attention deficits as well as the neurodegeneration associated with any one or more or combination of the following: attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulimia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

Attention deficit disorder is generally treated with methylphenidate, an amphetamine-like molecule that has some potential for abuse. Accordingly, it would be desirable to provide a drug that treats attention deficit disorder while having fewer side effects than the currently used drug.

Attention deficit hyperactivity disorder, otherwise known as ADHD, is a neurobehavioral disorder affecting 3–5% of all American children. ADHD concerns cognitive alone or both cognitive and behavioral actions by interfering with a person's ability to stay on a task and to exercise age-appropriate inhibition. Several types of ADHD exist: a predominantly inattentive subtype, a predominantly hyperactive-impulsive subtype, and a combined subtype. Treatment may include medications such as methylphenidate, dextroamphetamine, or pemoline, which act to decrease impulsivity and hyperactivity and to increase attention. No "cure" for ADHD currently exists. Children with the disorder seldom outgrow it; therefore, there is a need for appropriate medicaments.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Anxiety disorders (disorders with prominent anxiety or phobic avoidance), represent an area of unmet medical needs in the treatment of psychiatric illness. See Diagnostic & Statistical Manual of Mental Disorders, IV (1994), pp 393–394, for various disease forms of anxiety.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Anxiety also includes post-traumatic stress disorder (PTSD), which is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat post traumatic stress disorder.

Mood and affective disorders fall within a large group of diseases, including monopolar depression and bi-polar mood disorder. These diseases are treated with three major classes of compounds. The first group is the heterocyclic antidepressant (HCA's). This group includes the well-known tricyclic antidepressants. The second group of compounds used to treat mood disorders is the monoamine oxidase inhibitors (MAOI's) that are used in particular types of diseases. The third drug is lithium. Common side effects from HCA's are sedation and weight gain. In elderly patients with organic brain disease, the side effects of HCA's can also include seizures and behavioral symptoms. The main side effects from using MAOI's occur from dietary and drug interactions. Benign side effects from the use of lithium include, but are not limited to, weight gain, nausea, diarrhea, polyuria, polydipsia, and tremor. Toxic side effects from lithium can include persistent headache, mental confusion, and may reach seizures and cardiac arrhythmias. Therefore, agents with less side effects or interactions with food or other medications would be useful.

Borderline personality disorder, although not as well known as bipolar disorder, is more common. People having borderline personality disorder suffer from a disorder of emotion regulation. Pharmaceutical agents are used to treat specific symptoms, such as depression or thinking distortions.

Acquired immune deficiency syndrome (AIDS) results from an infection with the human immunodeficiency virus (HIV). This virus attacks selected cells and impairs the proper function of the immune, nervous, and other systems. HIV infection can cause other problems such as, but not limited to, difficulties in thinking, otherwise known as AIDS dementia complex. Therefore, there is a need to drugs to relieve the confusion and mental decline of persons with AIDS.

Amyotrophic lateral sclerosis, also known as Lou Gehrig's disease, belongs to a class of disorders known as motor neuron diseases wherein specific nerve cells in the brain and spinal cord gradually degenerate to negatively affect the control of voluntary movement. Currently, there is no cure for amyotrophic lateral sclerosis although patients may receive treatment from some of their symptoms and although Riluzole has been shown to prolong the survival of patients. Therefore, there is a need for a pharmaceutical agent to treat this disease.

Traumatic brain injury occurs when the brain is damaged from a sudden physical assault on the head. Symptoms of the traumatic brain injury include confusion and other cognitive problems. Therefore, there is a need to address the symptoms of confusion and other cognitive problems.

Brain tumors are abnormal growths of tissue found inside of the skull. Symptoms of brain tumors include behavioral and cognitive problems. Surgery, radiation, and chemotherapy are used to treat the tumor, but other agents are necessary to address associated symptoms. Therefore, there is a need to address the symptoms of behavioral and cognitive problems.

Persons with Down's syndrome have in all or at least some of their cells an extra, critical portion of the number 21 chromosome. Adults who have Down's syndrome are known to be at risk for Alzheimer-type dementia. Currently, there is no proven treatment for Down's syndrome. Therefore, there is a need to address the dementia associated with Down's syndrome.

Genetically programmed degeneration of neurons in certain areas of the brain cause Huntington's disease. Early symptoms of Huntington's disease include mood swings, or trouble learning new things or remembering a fact. Most drugs used to treat the symptoms of Huntington's disease have side effects such as fatigue, restlessness, or hyperexcitability. Currently, there is no treatment to stop or reverse the progression of Huntington's disease. Therefore, there is a need of a pharmaceutical agent to address the symptoms with fewer side effects.

Dementia with Lewy Bodies is a neurodegenerative disorder involving abnormal structures known as Lewy bodies found in certain areas of the brain. Symptoms of dementia with Lewy bodies include, but are not limited to, fluctuating cognitive impairment with episodic delirium. Currently, treatment concerns addressing the parkinsonian and psychiatric symptoms. However, medicine to control tremors or loss of muscle movement may actually accentuate the underlying disease of dementia with Lewy bodies. Therefore, there is a need of a pharmaceutical agent to treat dementia with Lewy bodies.

Parkinson's disease is a neurological disorder characterized by tremor, hypokinesia, and muscular rigidity. Currently, there is no treatment to stop the progression of the disease. Therefore, there is a need of a pharmaceutical agent to address Parkinson's.

Tardive dyskinesia is associated with the use of conventional antipsychotic drugs. This disease is characterized by involuntary movements most often manifested by puckering of the lips and tongue and/or writhing of the arms or legs. The incidence of tardive dyskinesia is about 5% per year of drug exposure among patients taking conventional antipsychotic drugs. In about 2% of persons with the disease, tardive dyskinesia is severely disfiguring. Currently, there is no generalized treatment for tardive dyskinesia. Furthermore, the removal of the effect-causing drugs is not always an option due to underlying problems. Therefore, there is a need for a pharmaceutical agent to address the symptoms of tardive dyskinesia.

Pick's disease results from a slowly progressive deterioration of social skills and changes in personality with the resulting symptoms being impairment of intellect, memory, and language. Common symptoms include memory loss, lack of spontaneity, difficulty in thinking or concentrating, and speech disturbances. Currently, there is no specific treatment or cure for Pick's disease but some symptoms can be treated with cholinergic and serotonin-boosting antidepressants. In addition, antipsychotic medications may alleviate symptoms in FTD patients who are experiencing delusions or hallucinations. Therefore, there is a need for a pharmaceutical agent to treat the progressive deterioration of social skills and changes in personality and to address the symptoms with fewer side effects.

Dysregulation of food intake associated with eating disease, including bulemia nervosa and anorexia nervosa, involve neurophysiological pathways. Anorexia nervosa is hard to treat due to patients not entering or remaining in after entering programs. Currently, there is no effective treatment for persons suffering from severe anorexia nervosa. Cognitive behavioral therapy has helped patients suffering from bulemia nervosa; however, the response rate is only about 50% and current treatment does not adequately address emotional regulation. Therefore, there is a need for pharmaceutical agents to address neurophysiological problems underlying diseases of dysregulation of food intake.

Cigarette smoking has been recognized as a major public health problem for a long time. However, in spite of the public awareness of health hazard, the smoking habit remains extraordinarily persistent and difficult to break. There are many treatment methods available, and yet people continue to smoke. Administration of nicotine transdermally, or in a chewing gum base is common treatments. However, nicotine has a large number of actions in the body, and thus can have many side effects. It is clear that there is both a need and a demand of long standing for a convenient and relatively easy method for aiding smokers in reducing or eliminating cigarette consumption. A drug that could selectively stimulate only certain of the nicotinic receptors would be useful in smoke cessation programs.

Smoke cessation programs may involve oral dosing of the drug of choice. The drug may be in the form of tablets. However, it is preferred to administer the daily dose over the waking hours, by administration of a series of incremental doses during the day. The preferred method of such administration is a slowly dissolving lozenge, troche, or chewing gum, in which the drug is dispersed. Another drug in treating nicotine addiction is Zyban. This is not a nicotine replacement, as are the gum and patch. Rather, this works on other areas of the brain, and its effectiveness is to help control nicotine craving or thoughts about cigarette use in people trying to quit. Zyban is not very effective and effective drugs are needed to assist smokers in their desire to stop smoking. These drugs may be administered transdermally through the use of skin patches. In certain cases, the drugs may be administered by subcutaneous injection, especially if sustained release formulations are used.

Drug use and dependence is a complex phenomenon, which cannot be encapsulated within a single definition. Different drugs have different effects, and therefore different types of dependence. Drug dependence has two basic causes, that is, tolerance and physical dependence. Tolerance exists when the user must take progressively larger doses to produce the effect originally achieved with smaller doses. Physical dependence exists when the user has developed a state of physiologic adaptation to a drug, and there is a withdrawal (abstinence) syndrome when the drug is no longer taken. A withdrawal syndrome can occur either when the drug is discontinued or when an antagonist displaces the drug from its binding site on cell receptors, thereby counteracting its effect. Drug dependence does not always require physical dependence.

In addition drug dependence often involves psychological dependence, that is, a feeling of pleasure or satisfaction when taking the drug. These feelings lead the user to repeat the drug experience or to avoid the displeasure of being deprived of the drug. Drugs that produce strong physical dependence, such as nicotine, heroin and alcohol are often abused, and the pattern of dependence is difficult to break. Drugs that produce dependence act on the CNS and generally reduce anxiety and tension; produce elation, euphoria, or other pleasurable mood changes; provide the user feelings of increased mental and physical ability; or alter sensory perception in some pleasurable manner. Among the drugs that are commonly abused are ethyl alcohol, opioids, anxiolytics, hypnotics, cannabis (marijuana), cocaine, amphetamines, and hallucinogens. The current treatment for drug-addicted people often involves a combination of behavioral therapies and medications. Medications, such as methadone or LAAM (levo-alpha-acetyl-methadol), are effective in suppressing the withdrawal symptoms and drug craving associated with narcotic addiction, thus reducing illicit drug use and improving the chances of the individual remaining in treatment. The primary medically assisted withdrawal method for narcotic addiction is to switch the patient to a comparable drug that produces milder withdrawal symptoms, and then gradually taper off the substitute medication. The medication used most often is methadone, taken orally once a day. Patients are started on the lowest dose that prevents the more severe signs of withdrawal and then the dose is gradually reduced. Substitutes can be used also for withdrawal from sedatives. Patients can be switched to long-acting sedatives, such as diazepam or phenobarbital, which are then gradually reduced.

Gilles de la Tourette's Syndrome is an inherited neurological disorder. The disorder is characterized by uncontrollable vocal sounds called tics and involuntary movements. The symptoms generally manifest in an individual before the person is 18 years of age. The movement disorder may begin with simple tics that progress to multiple complex tics, including respiratory and vocal ones. Vocal tics may begin as grunting or barking noises and evolve into compulsive utterances. Coprolalia (involuntary scatologic utterances) occurs in 50% of patients. Severe tics and coprolalia may be physically and socially disabling. Tics tend to be more complex than myoclonus, but less flowing than choreic movements, from which they must be differentiated. The patient may voluntarily suppress them for seconds or minutes.

Currently simple tics are often treated with benzodiazepines. For simple and complex tics, Clonidine may be used. Long-term use of Clonidine does not cause tardive dyskinesia; its limiting adverse effect is hypotension. In more severe cases, antipsychotics, such as Haloperidol may be required, but side effects of dysphoria, parkinsonism, akathisia, and tardive dyskinesia may limit use of such antipsychotics. There is a need for safe and effective methods for treating this syndrome.

Age-related macular degeneration (AMD) is a common eye disease of the macula which is a tiny area in the retina that helps produce sharp, central vision required for "straight ahead" activities that include reading and driving. Persons with AMD lose their clear, central vision. AMD takes two forms: wet and dry. In dry AMD, there is a slow breakdown of light-sensing cells in the macula. There currently is no cure for dry AMD. In wet AMD, new, fragile blood vessels growing beneath the macula as dry AMD worsens and these vessels often leak blood and fluid to cause rapid damage to the macula quickly leading to the loss of central vision. Laser surgery can treat some cases of wet AMD. Therefore, there is a need of a pharmaceutical agent to address AMD.

Glaucoma is within a group of diseases occurs from an increase in intraocular pressure causing pathological changes in the optical disk and negatively affects the field of vision. Medicaments to treat glaucoma either decrease the amount of fluid entering the eye or increase drainage of fluids from the eye in order to decrease intraocular pressure. However, current drugs have drawbacks such as not working over time or causing side effects so the eye-care professional has to either prescribe other drugs or modify the prescription of the drug being used. There is a need for safe and effective methods for treating problems manifesting into glaucoma.

Ischemic periods in glaucoma cause release of excitotoxic amino acids and stimulate inducible form of nitric oxide synthase (iNOS) leading to neurodegeneration. Alpha 7 nicotinic agonists may stimulate the release of inhibitory amino acids such as GABA which will dampen hyperexcitablity. Alpha 7 nicotinic agonists are also directly neuroprotective on neuronal cell bodies. Thus alpha 7 nicotinic agonists have the potential to be neuroprotective in glaucoma.

Persons afflicted with pain often have what is referred to as the "terrible triad" of suffering from the pain, resulting in sleeplessness and sadness, all of which are hard on the afflicted individual and that individual's family. Pain can manifest itself in various forms, including, but not limited to, headaches of all severity, back pain, neurogenic, and pain from other ailments such as arthritis and cancer from its existence or from therapy to eradicate it. Pain can be either chronic (persistent pain for months or years) or acute (short-lived, immediate pain to inform the person of possible injury and need of treatment). Persons suffering from pain respond differently to individual therapies with varying degrees of success. There is a need for safe and effective methods for treating pain.

Finally, the compounds of the present invention may be used in combination therapy with typical and a typical anti-psychotic drugs (also called an anti-psychotic agent). All compounds within the present invention are useful for and may also be used in combination with each other to prepare pharmaceutical compositions. Such combination therapy lowers the effective dose of the anti-psychotic drug and thereby reduces the side effects of the anti-psychotic drugs. Some typical anti-psychotic drugs that may be used in the practice of the invention include Haldol. Some a typical anti-psychotic drugs include Ziprasidone, Olanzapine, Resperidone, and Quetiapine.

Compounds of Formula I can be prepared as shown in Scheme 1. The key step in the preparation of this class of compounds is the coupling of an amino-azabicyclic moiety with the requisite acid chloride (Lv=Cl), mixed anhydride (e.g., Lv=diphenyl phosphoryl, bis(2-oxo-3-oxazolidinyl) phosphinyl, or acyloxy of the general formula of O—C(O)—$R_{Lv}$, where $R_{Lv}$ includes phenyl or t-butyl), or carboxylic acid (Lv=OH) in the presence of an activating agent. Suitable activating reagents are well known in the art, for examples see Kiso, Y., Yajima, H. "Peptides" pp. 39–91, San Diego, Calif., Academic Press, (1995), and include, but are not limited to, agents such as carbodiimides, phosphonium and uronium salts (such as HATU).

Scheme 1

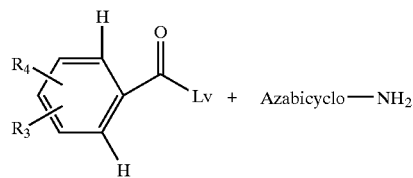

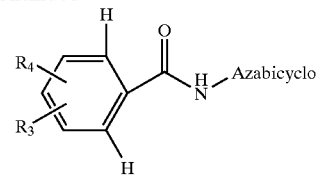

Generally, the acid is activated using HATU or is converted to the acyl azide by using DPPA. The appropriate amine is added to a solution of the appropriate anhydride or azide to give the desired final compounds, but if the amine is in the form of an acid salt, it is first reacted with TEA before adding to the anhydride or azide. In some cases, the ester (Lv being OMe or OEt) may be reacted directly with the amine in an alcoholic solvent heated to reflux temperature to give the compounds of Formula I.

It will be apparent to those skilled in the art that the requisite carboxylic acids can be obtained commercially or can be synthesized by known procedures. The acid required in Example 1 is synthesized by acetylation of the corresponding phenol with acetylchloride. The acids in Examples 2, 8–16 are synthesized from the corresponding esters by hydrolysis. Typical hydrolysis procedures are well known in the art. Preferably, the ester is treated with aqueous lithium hydroxide in a solvent such as dioxane. The requisite esters are synthesized from the reaction of a phenol and arylboronic acid as described in *Tet. Lett.*, 2937–2940 (1998). The phenol and boronic acid are reacted in the presence of a copper salt like copper (II) acetate and a base like TEA (Scheme 2). The acids for Examples 3–7 are commercially available. The acids required for Examples 17–22 are synthesized from the corresponding esters by hydrolysis as described above. The esters are synthesized by the reaction of a thiophenol with an aryl halide as described in *Synlett*, 1579–1581 (1999). Namely, the thiophenol and aryl iodide are heated in the presence of a palladium (0) source such as tetrakis(triphenylphosphine)palladium (0) and a base, preferably sodium tert-butoxide.

Scheme 2

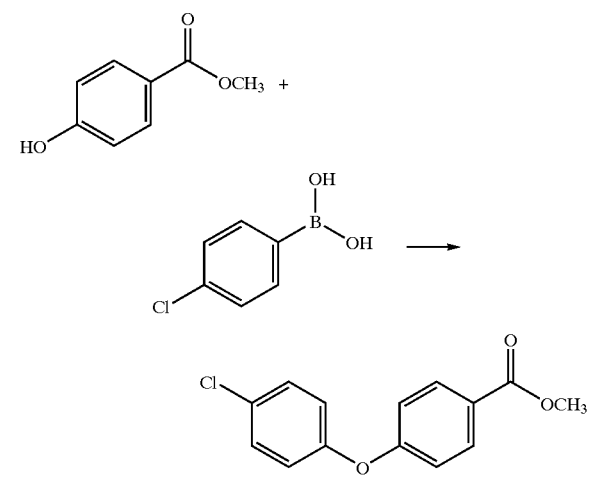

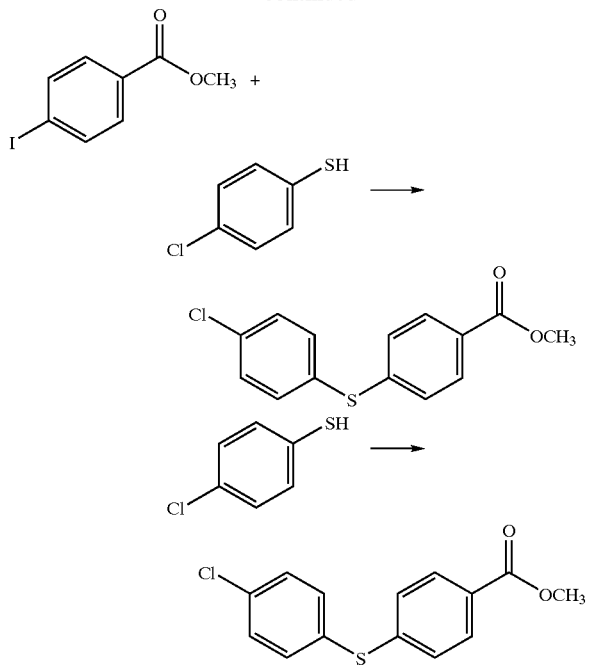

There are a variety of methods for constructing thioamides. One can treat the corresponding amide with a reagent such as Lawesson's reagent (2,4-bis(4-methoxyphenyl)-1,3-dithia-2,4-diphosphetane-2,4-disulfide) (see Lawesson et. al. in *Bull. Soc. Chim. Belg.*, 229 (1978)), or $P_4S_{10}$ (see *Chem. Rev.*, 45 (1961)). Alternatively one can use a dithiocarboxylic ester to form a thioamide from the corresponding amide.

N-(2-azabicyclo[2.2.1]hept)-5-amine and 6-amine

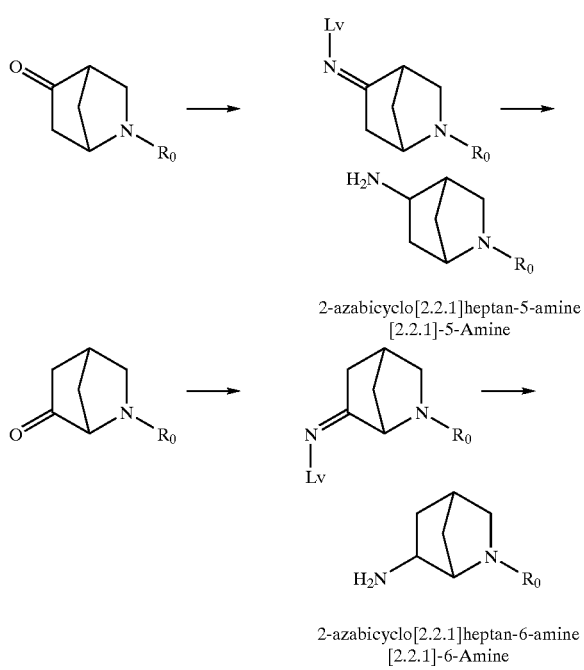

2-azabicyclo[2.2.1]heptan-5-amine
[2.2.1]-5-Amine 2-azabicyclo[2.2.1]heptan-6-amine
[2.2.1]-6-Amine where Lv can be —$CH_2Ph$, —$CH(Me)Ph$, —OH, —OMe, or —$OCH_2Ph$.

The respective amine precursors for Azabicyclo III and Azabicyclo IV can be prepared by reduction of an oxime or an imine of the corresponding N-2-azabicyclo[2.2.1]-heptanone by methods known to one skilled in the art (see *J. Labelled Compds. Radiopharm.*, 53–60 (1995), *J. Med. Chem.* 988–995, (1998), *Synth. Commun.* 1895–1911 (1992), *Synth. Commun.* 2009–2015 (1996)). The oximes can be prepared by treatment of the N-2-azabicyclo[2.2.1] heptanones with hydroxylamine hydrochloride in the presence of a base. The imines can be prepared by treatment of the N-2-azabicyclo[2.2.1]-heptanones with a primary amine under dehydrating conditions. The N-2-azabicyclo[2.2.1] heptanones can be prepared by known procedures (see *Tet. Lett.* 1419–1422 (1999), *J. Med. Chem.* 2184–2191 (1992), *J. Med. Chem.* 706–720 (2000), *J. Org. Chem.*, 4602–4616 (1995)).

One of ordinary skill in the art will recognize that the methods described for the reaction of the unsubstituted 3-amino-1-azabicyclo[2.2.1]heptane ($R_2$=H) are equally applicable to substituted compounds ($R_2 \neq H$). For where Azabicyclo I has substitution at C-2, compounds can be prepared from appropriately substituted nitro alcohols using procedures described in *Tetrahedron* (1997), 53, p. 11121 as shown below. Methods to synthesize nitro alcohols are well known in the art (see *J. Am. Chem. Soc.* (1947), 69, p 2608). The scheme below is a modification of the synthesis of exo-3-amino-1-azabicyclo[2.2.1]heptane as the bis(hydro para-toluenesulfonate) salt, described in detail herein, to show how to obtain these amine precursors. The desired salt can be made using standard procedures.

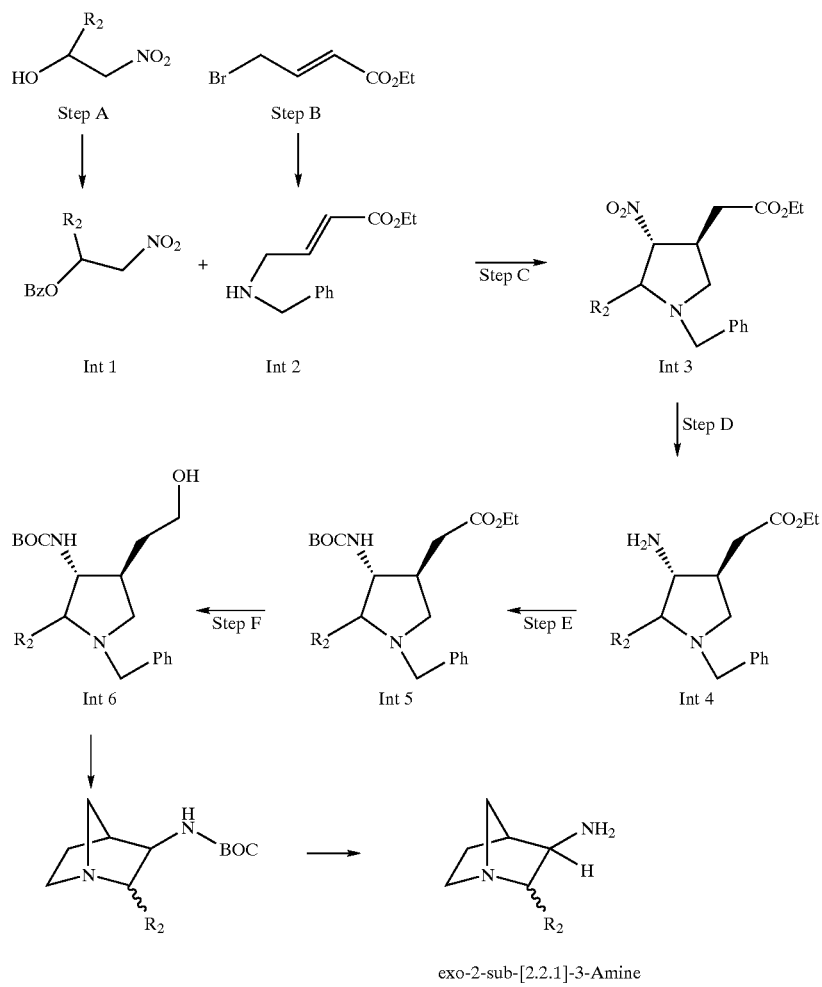

For Azabicyclo II where $R_2$ is present at the C-6 position, compounds can also be prepared by modification of intermediates described in the synthesis of exo-3-amino-1-azabicyclo[2.2.1]heptane as the bis(hydro para-toluenesulfonate) salt, described in detail herein. For example, Int 6 can be oxidized to the aldehyde and treated with an organometallic reagent to provide Int 20 using procedures described in *Tetrahedron* (1999), 55, p 13899. Int 20 can be converted into the amine using methods described for the synthesis of exo-3-amino-1-azabicyclo[2.2.1]heptane as the bis(hydro para-toluenesulfonate) salt. Once the amine is obtained, the desired salt can be made using standard procedures.

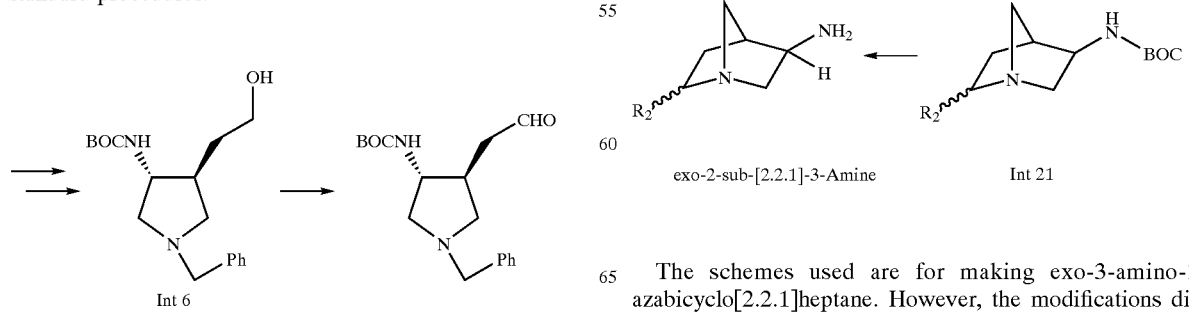

The schemes used are for making exo-3-amino-1-azabicyclo[2.2.1]heptane. However, the modifications discussed are applicable to make the endo isomer also.

There are several methods by which the amine precursor for Azabicyclo I can be obtained.

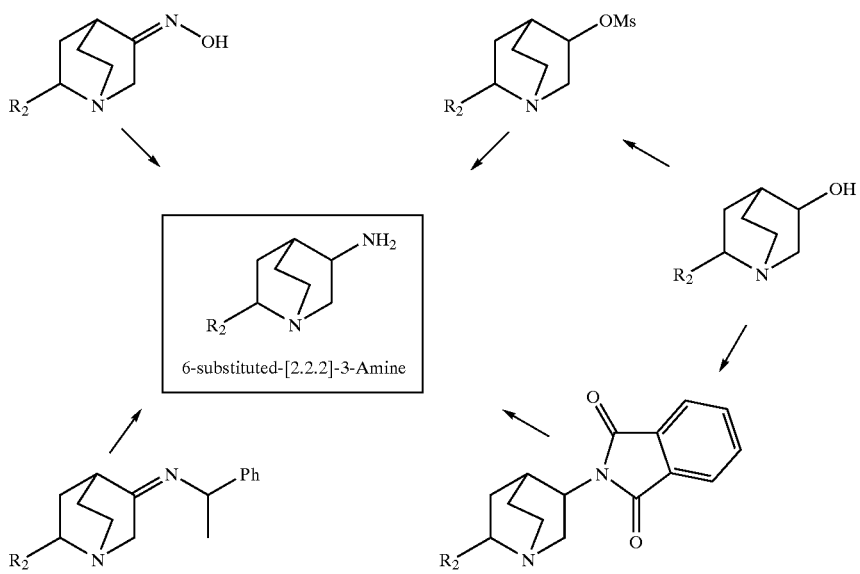

The oximes can be prepared by treatment of the 3-quinuclidinones with hydroxylamine hydrochloride in the presence of base. The imines can be prepared by treatment of the 3-quinuclidinones with a primary amine under dehydrating conditions. The 3-hydroxyquinuclidines can be prepared by reduction of the 3-quinuclidinones. The 6-substituted-3-quinuclidinones can be prepared by known procedures (see *J. Gen. Chem. Russia* 3791–3795, (1963), *J. Chem. Soc. Perkin Trans. I* 409–420 (1991), *J. Org. Chem.* 3982–3996 (2000)).

Amines

Preparation of the 1-azabicyclo-2.2.1 Amines

Synthesis of (3R,4S)-3-amino-1-azabicyclo[2.2.1] heptane as the bis(hydro para-toluenesulfonate) salt (exo-[2.2.1]-Amine):

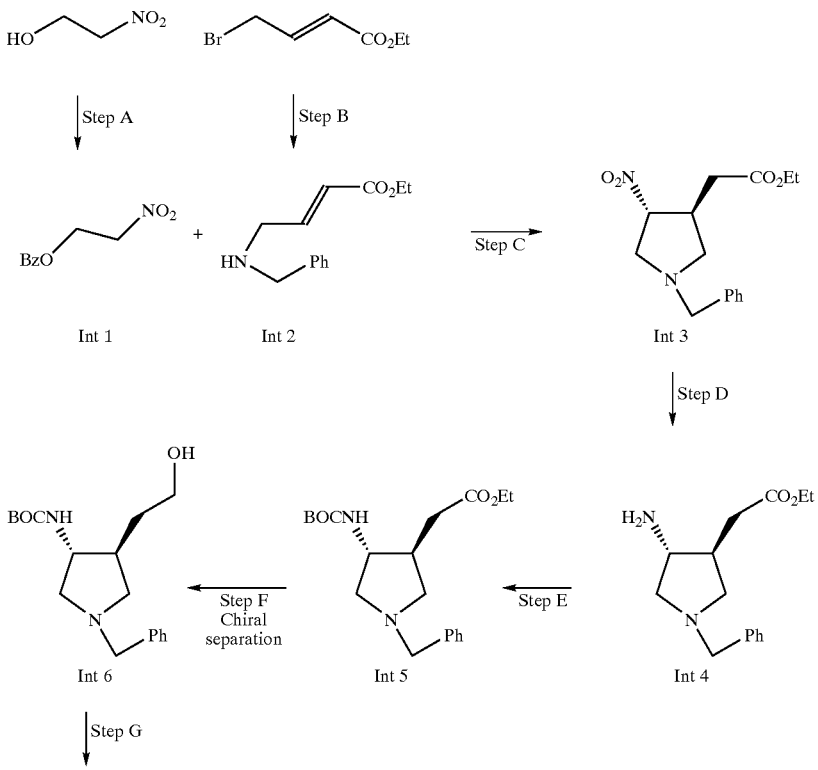

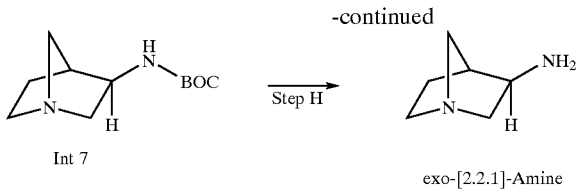

Int 7            exo-[2.2.1]-Amine

Step A. Preparation of 2-(benzoyloxy)-1-nitroethane (Int 1).

Benzoyl chloride (14.9 mL, 128 mmol) is added to a stirred solution of nitroethanol (9.2 mL, 128 mmol) in dry benzene (120 mL). The solution is refluxed for 24 hr and then concentrated in vacuo. The crude product is purified by flash chromatography on silica gel. Elution with hexanes-EtOAc (80:20) affords Int 1 as a white solid (68% yield): $^1$H NMR (300 MHz, CDCl$_3$) δ 8.0, 7.6, 7.4, 4.9, 4.8.

Step B. Preparation of Ethyl E-4-(benzylamino)-2-butenoate (Int 2).

Ethyl E-4-bromo-2-butenoate (10 mL, 56 mmol, tech grade) is added to a stirred solution of benzylamine (16 mL, 146 mmol) in CH$_2$Cl$_2$ (200 mL) at rt. The reaction mixture stirs for 15 min, and is diluted with ether (1 L). The mixture is washed with saturated aqueous NaHCO$_3$ solution (3×) and water, dried over Na$_2$SO$_4$, filtered and concentrated in vacuo. The residue is purified by flash chromatography on silica gel. Elution with hexanes-EtOAc (70:30) affords Int 2 as a clear oil (62% yield): $^1$H NMR (300 MHz, CDCl$_3$) δ 7.4–7.2, 7.0, 6.0, 4.2, 3.8, 3.4, 2.1–1.8, 1.3.

Step C. Preparation of trans-4-nitro-1-(phenylmethyl)-3-pyrrolidineacetic acid ethyl ester (Int 3).

A solution of Int 1 (6.81 g, 34.9 mmol) and Int 2 (7.65 g, 34.9 mmol) in EtOH (70 mL) stirs at rt for 15 h and is then concentrated in vacuo. The residue is diluted with ether (100 mL) and saturated aqueous NaHCO$_3$ solution (100 mL). The organic layer is separated and dried over Na$_2$SO$_4$, filtered and concentrated in vacuo. The crude product is purified by flash chromatography on silica gel. Elution with hexanes-EtOAc (85:15) affords Int 3 as a clear oil (76% yield): $^1$H NMR (300 MHz, CDCl$_3$) δ 7.4–7.3, 4.8–4.7, 4.1, 3.8–3.6, 3.3–3.0, 2.7–2.6, 2.4–2.3, 1.2.

Step D. Preparation of trans-4-amino-1-(phenylmethyl)-3-pyrrolidineacetic acid ethyl ester (Int 4).

A mixture of Int 3 (3.28 g, 11.2 mmol) and RaNi (1.5 g) in EtOH (100 mL) is placed in a Parr bottle and hydrogenated for 4 h under an atmosphere of hydrogen (46 psi) at rt. The mixture is filtered through a pad of Celite, and the solvent is removed in vacuo to afford Int 4 as a clear oil (100% yield): $^1$H NMR (300 MHz, CDCl$_3$) δ 7.3–7.2, 4.1, 3.6, 3.2, 3.0–2.9, 2.8, 2.8–2.6, 2.6–2.4, 2.30–2.2, 1.2.

Step E. Preparation of trans-4-(1,1-dimethylethoxycarbonylamido)-1-(phenylmethyl)-3-pyrrolidineacetic acid ethyl ester (Int 5).

Di-tert-butyldicarbonate (3.67 g, 16.8 mmol) is added to a stirred solution of Int 4 (2.94 g, 11.2 mmol) in CH$_2$Cl$_2$ (30 mL) cooled in an ice bath. The reaction is allowed to warm to rt and stirred overnight. The mixture is concentrated in vacuo. The crude product is purified by flash chromatography on silica gel. Elution with hexanes-EtOAc (80:20) affords Int 5 as a white solid (77% yield): $^1$H NMR (300 MHz, CDCl$_3$) δ 7.4–7.2, 5.1–4.9, 4.1, 4.0–3.8, 3.6, 3.2–3.0, 2.8–2.6, 2.5–2.4, 2.3–2.1, 1.4, 1.3.

Step F. Preparation of trans(tert-butoxycarbonylamino)-4-(2-hydroxyethyl)-1-(N-phenylmethyl)pyrrolidine (Int 6).

LiAlH$_4$ powder (627 mg, 16.5 mmol) is added in small portions to a stirred solution of Int 5 (3.0 g, 8.3 mmol) in anhydrous THF (125 mL) in a −5° C. bath. The mixture is stirred for 20 min in a −5° C. bath, then quenched by the sequential addition of water (0.6 mL), 15% (w/v) aqueous NaOH (0.6 mL) and water (1.8 mL). Excess anhydrous K$_2$CO$_3$ is added, and the mixture is stirred for 1 h, then filtered. The filtrate is concentrated in vacuo. The residue is purified by flash chromatography on silica gel. Elution with EtOAc affords Int 6 as a white solid (94% yield): $^1$H NMR (300 MHz, CDCl$_3$) δ 7.4–7.3, 5.3–5.2, 4.1–4.0, 3.9–3.7, 3.3–3.2, 2.8–2.7, 2.3–2.1, 1.7, 1.5.

Int 6 is a racemic mixture that can be resolved via chromatography using a Diacel chiral pack AD column. From the two enantiomers thus obtained, the (+)-enantiomer, $[\alpha]^{25}_D$+35 (c 1.0, MeOH), gives rise to the corresponding enantiomerically pure exo-4-S final compounds, whereas the (−)-enantiomer, $[\alpha]^{25}_D$−34 (c 0.98, MeOH), gives rise to enantiomerically pure exo-4-R final compounds. The methods described herein use the (+)-enantiomer of Int 6 to obtain the enantiomerically pure exo-4-S final compounds. However, the methods used are equally applicable to the (−)-enantiomer of Int 6, making non-critical changes to the methods provided herein to obtain the enantiomerically pure exo-4-R final compounds.

Step G. Preparation of exo 3-(tert-butoxycarbonylamino)-1-azabicyclo[2.2.1]heptane (Int 7).

TEA (8.0 g, 78.9 mml) is added to a stirred solution of Int 6 (2.5 g, 7.8 mmol) in CH$_2$Cl$_2$ (50 mL), and the reaction is cooled in an ice-water bath. CH$_3$SO$_2$Cl (5.5 g, 47.8 mmol) is then added dropwise, and the mixture is stirred for 10 min in an ice-water bath. The resulting yellow mixture is diluted with saturated aqueous NaHCO$_3$ solution, extracted with CH$_2$Cl$_2$ several times until no product remains in the aqueous layer by TLC. The organic layers are combined, washed with brine, dried over Na$_2$SO$_4$ and concentrated in vacuo. The residue is dissolved in EtOH (85 mL) and is heated to reflux for 16 h. The reaction mixture is allowed to cool to rt, transferred to a Parr bottle and treated with 10% Pd/C catalyst (1.25 g). The bottle is placed under an atmosphere of hydrogen (53 psi) for 16 h. The mixture is filtered through Celite, and fresh catalyst (10% Pd/C, 1.25 g) is added. Hydrogenolysis continues overnight. The process is repeated three more times until the hydrogenolysis is complete. The final mixture is filtered through Celite and concentrated in vacuo. The residue is purified by flash chromatography on silica gel. Elution with CHCl$_3$—MeOH—NH$_4$OH (90:9.5:0.5) affords Int 7 as a white solid (46% yield): $^1$H NMR (300 MHz, CDCl$_3$) δ 5.6–5.5, 3.8–3.7, 3.3–3.2, 2.8–2.7, 2.0–1.8, 1.7–1.5, 1.5.

Step H. Preparation of exo-3-amino-1-azabicyclo[2.2.1]heptane bis(hydro-para-toluenesulfonate).

Para-toluenesulfonic acid monohydrate (1.46 g, 7.68 mmol) is added to a stirred solution of Int 7 (770 mg, 3.63 mmol) in EtOH (50 mL). The reaction mixture is heated to reflux for 10 h, followed by cooling to rt. The precipitate is collected by vacuum filtration and washed with cold EtOH to give exo-[2.2.1]-Amine as a white solid (84% yield): $^1$H NMR (400 MHz, CD$_3$OD) δ 7.7, 7.3, 3.9–3.7, 3.7–3.3, 3.2, 2.4, 2.3–2.2, 1.9–1.8.

Synthesis of endo-3-amino-1-azabicyclo[2.2.1]
heptane as the bis(hydro para-toluenesulfonate) salt
(endo-[2.2.1]-Amine)

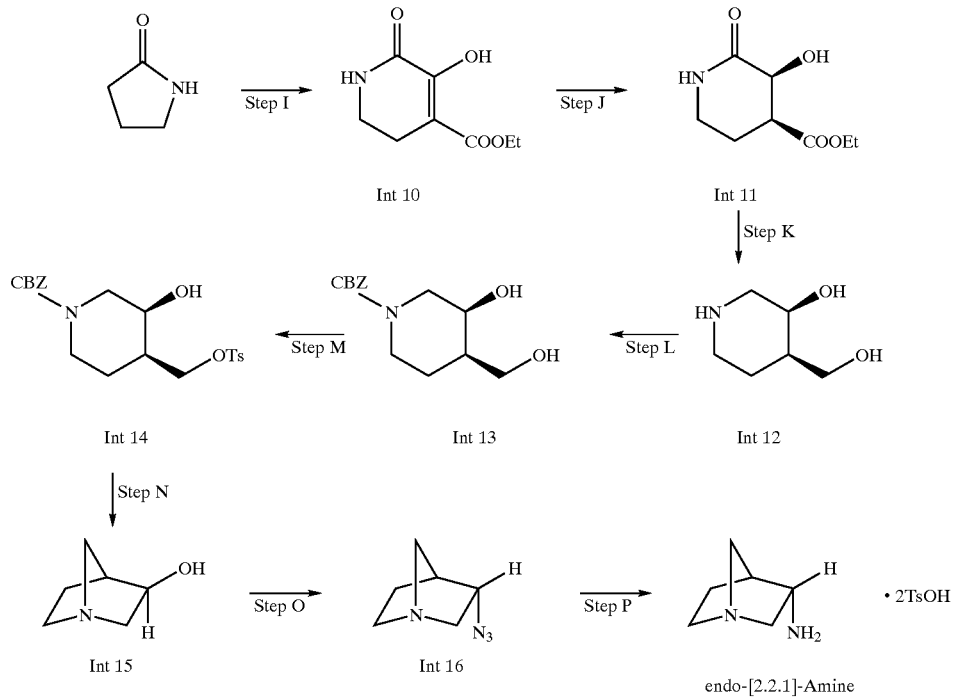

Step I. Preparation of ethyl 5-hydroxy-6-oxo-1,2,3,6-tetrahydropyridine-4-carboxylate (Int 10).

Absolute EtOH (92.0 mL, 1.58 mol) is added to a mechanically stirred suspension of potassium ethoxide (33.2 g, 395 mmol) in dry toluene (0.470 L). When the mixture is homogeneous, 2-pyrrolidinone (33.6 g, 395 mmol) is added, and then a solution of diethyl oxalate (53.1 mL, 390 mmol) in toluene (98 mL) is added via an addition funnel. After complete addition, toluene (118 mL) and EtOH (78 mL) are added sequentially. The mixture is heated to reflux for 18 h. The mixture is cooled to rt and aqueous HCl (150 mL of a 6.0 M solution) is added. The mixture is mechanically stirred for 15 min. The aqueous layer is extracted with $CH_2Cl_2$, and the combined organic layers are dried ($MgSO_4$), filtered and concentrated in vacuo to a yellow residue. The residue is recrystallized from EtOAc to afford Int 10 as a yellow solid (38% yield): $^1$H NMR (300 MHz, $CDCl_3$) δ 11.4, 7.4, 4.3, 3.4, 2.6, 1.3.

Step J. Preparation of ethyl cis-3-hydroxy-2-oxopiperidine-4-carboxylate (Int 11).

A mixture of Int 10 (15 g, 81 mmol) and 5% rhodium on carbon (2.0 g) in glacial acetic acid is placed under an atmosphere of hydrogen (52 psi). The mixture is shaken for 72 h. The mixture is filtered through Celite, and the filtrate is concentrated in vacuo to afford Int 11 as a white solid (98% yield): $^1$H NMR (300 MHz, $CDCl_3$) δ 6.3, 4.2, 4.0–3.8, 3.4, 3.3–3.2, 2.2, 1.3.

Step K. Preparation of cis-4-(hydroxymethyl)piperidin-3-ol (Int 12).

Int 11 (3.7 g, 19.9 mmol) as a solid is added in small portions to a stirred solution of $LiAlH_4$ in THF (80 mL of a 1.0 M solution) in an ice-water bath. The mixture is warmed to rt, and then the reaction is heated to reflux for 48 h. The mixture is cooled in an ice-water bath before water (3.0 mL, 170 mmol) is added dropwise, followed by the sequential addition of NaOH (3.0 mL of a 15% (w/v) solution) and water (9.0 mL, 500 mmol). Excess $K_2CO_3$ is added, and the mixture is stirred vigorously for 15 min. The mixture is filtered, and the filtrate is concentrated in vacuo to afford Int 12 as a yellow powder (70% yield): $^1$H NMR (300 MHz, DMSO-$d_6$) δ 4.3, 4.1, 3.7, 3.5–3.2, 2.9–2.7, 2.5–2.3, 1.5, 1.3.

Step L. Preparation of benzyl cis-3-hydroxy-4-(hydroxymethyl)piperidine-1-carboxylate (Int 13).

N-(benzyloxy carbonyloxy)succinimide (3.04 g, 12.2 mmol) is added to a stirred solution of Int 12 (1.6 g, 12.2 mmol) in saturated aqueous $NaHCO_3$ (15 mL) at rt. The mixture is stirred at rt for 18 h. The organic and aqueous layers are separated. The aqueous layer is extracted with ether (3×). The combined organic layers are dried over anhydrous $K_2CO_3$, filtered and concentrated in vacuo to afford Int 13 as a yellow oil (99% yield): $^1$H NMR (300 MHz, $CDCl_3$) δ 7.4–7.3, 5.2, 4.3, 4.1, 3.8–3.7, 3.0–2.8, 2.1, 1.9–1.7, 1.4.

Step M. Preparation of benzyl cis-3-hydroxy-4-[(4-methylphenyl)sulfonyl oxymethyl]piperidine-1-carboxylate (Int 14).

Para-toluenesulfonyl chloride (1.0 g, 5.3 mmol) is added to a stirred solution of Int 13 (3.6 g, 5.3 mmol) in pyridine (10 mL) in a −15° C. bath. The mixture is stirred for 4 h, followed by addition of HCl (4.5 mL of a 6.0 M solution). $CH_2Cl_2$ (5 mL) is added. The organic and aqueous layers are separated. The aqueous layer is extracted with $CH_2Cl_2$. The combined organic layers are washed with brine, dried ($MgSO_4$), filtered and concentrated in vacuo to afford Int 14 as a colorless oil (78% yield): $^1$H NMR (300 MHz, $CDCl_3$) δ 7.8, 7.4–7.2, 5.1, 4.3–4.2, 4.1, 3.9–3.8, 2.9–2.7, 2.4, 1.9, 1.6–1.3.

Step N. Preparation of exo-1-azabicyclo[2.2.1]heptan-3-ol (Int 15).

A mixture of Int 14 (3.6 g, 8.6 mmol) and 10% Pd/C catalyst (500 mg) in EtOH (50 mL) is placed under an atmosphere of hydrogen. The mixture is shaken for 16 h. The mixture is filtered through Celite. Solid NaHCO$_3$ (1.1 g, 13 mmol) is added to the filtrate, and the mixture is heated in an oil bath at 50° C. for 5 h. The solvent is removed in vacuo. The residue is dissolved in saturated aqueous K$_2$CO$_3$ solution. Continuous extraction of the aqueous layer using a liquid-liquid extraction apparatus (18 h), followed by drying the organic layer over anhydrous K$_2$CO$_3$ and removal of the solvent in vacuo affords Int 15 as a white solid (91% yield): $^1$H NMR (300 MHz, CDCl$_3$) δ 3.8, 3.0–2.8, 2.6–2.5, 2.4–2.3, 1.7, 1.1.

Step O. Preparation of endo-3-azido-1-azabicyclo[2.2.1] heptane (Int 16).

To a mixture of Int 15 (1.0 g, 8.9 mmol) and triphenyl phosphine (3.0 g, 11.5 mmol) in toluene-THF (50 mL, 3:2) in an ice-water bath are added sequentially a solution of hydrazoic acid in toluene (15 mL of ca. 2 M solution) and a solution of diethyl azadicarboxylate (1.8 mL, 11.5 mmol) in toluene (20 mL). The mixture is allowed to warm to rt and stir for 18 h. The mixture is extracted with aqueous 1.0M HCl solution. The aqueous layer is extracted with EtOAc, and the combined organic layers are discarded. The pH of the aqueous layer is adjusted to 9 with 50% aqueous NaOH solution. The aqueous layer is extracted with CH$_2$Cl$_2$ (3×), and the combined organic layers are washed with brine, dried over Na$_2$SO$_4$, filtered and concentrated in vacuo. The crude product is purified by flash chromatography on silica gel. Elution with CHCl$_3$—MeOH—NH$_4$OH (92:7:1) affords Int 16 as a colorless oil (41% yield): $^1$H NMR (300 MHz, CDCl$_3$) δ 4.1, 3.2, 2.8, 2.7–2.5, 2.2, 1.9, 1.5.

Step P. Preparation of endo-3-amino-1-azabicyclo[2.2.1] heptane bis(hydro-para-toluenesulfonate).

A mixture of Int 16 (250 mg, 1.8 mmol) and 10% Pd/C catalyst (12 mg) in EtOH (10 mL) is placed under an atmosphere of hydrogen (15 psi). The mixture is stirred for 1 h at rt. The mixture is filtered through Celite, and the filtrate is concentrated in vacuo. The residue is dissolved in EtOH (10 mL) and para-toluenesulfonic acid monohydrate (690 mg, 3.7 mmol) is added. The mixture is stirred for 30 min, and the precipitate is filtered. The precipitate is washed sequentially with cold EtOH and ether. The precipitate is dried in vacuo to afford endo-[2.2.1]-Amine as a white solid (85% yield): $^1$H NMR (300 MHz, CD$_3$OD) δ 7.7, 7.3, 4.2, 3.9, 3.6–3.4, 3.3–3.2, 2.4, 2.3, 2.1.

Preparation of 1-azabicyclo[3.2.1]octan-3-amine

Preparation of the 3R,5R-[3.2.1]-Amine

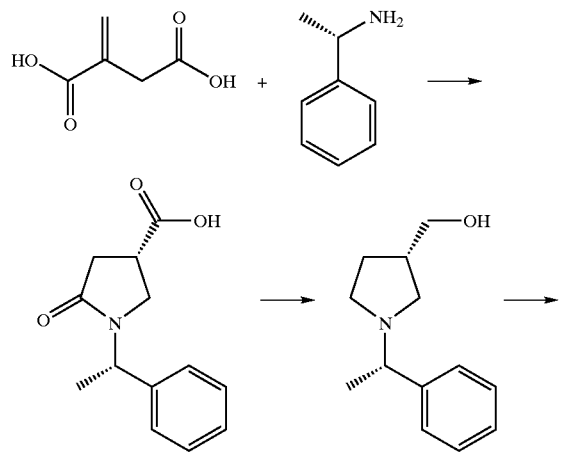

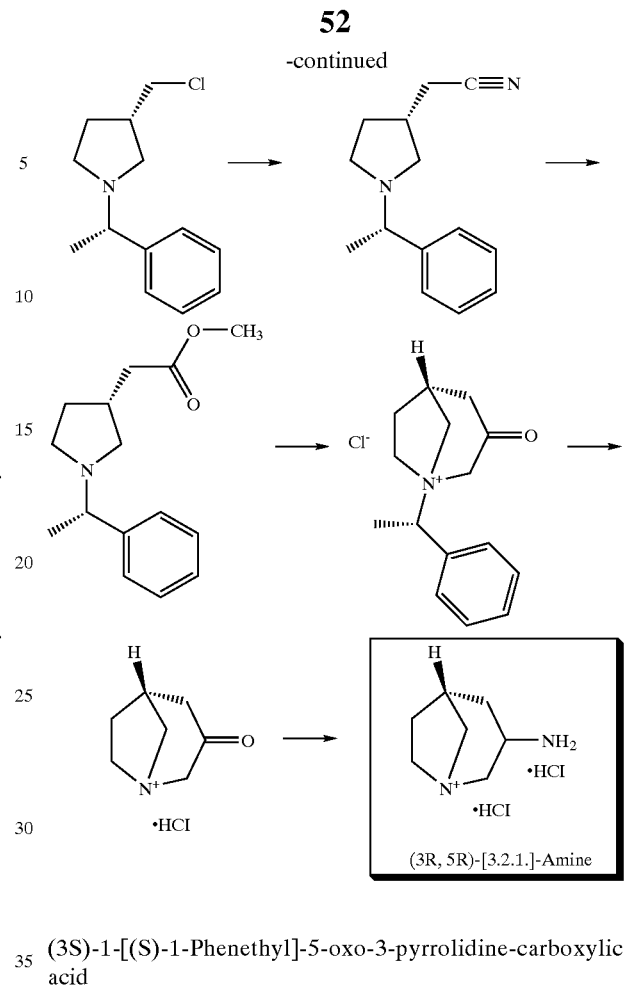

(3S)-1-[(S)-1-Phenethyl]-5-oxo-3-pyrrolidine-carboxylic acid

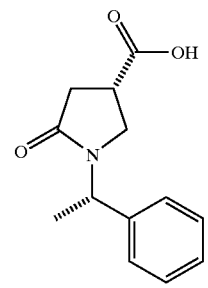

According to the literature procedure (Nielsen et al. J. Med. Chem 1990, 70–77), a mixture of itaconic acid (123.17 g, 946.7 mmol) and (S)-(−)-α-methyl benzylamine (122.0 mL, 946.4 mmol) were heated (neat) in a 160° C. oil bath for 4 h. Upon cooling, MeOH (~200 mL) was added and the resulting solid collected by filtration. The solid was treated with EtOH (~700 mL) and warmed using a steam bath until ~450 mL solvent remained. After cooling to rt, the solid was collected and dried to afford 83.2 g as a white crystalline solid: [α]$^{25}_D$=−80 (c 0.97, DMSO). MS (EI) m/z 233 (M$^+$), 233, 218, 160, 105, 104, 103, 91, 79, 78, 77.

The lack of a resonance 3.59 indicates a single diastereomer. The other diastereomer can be retrieved from the initial MeOH triturant. Attempts to crystallize this material generally led to small quantities of (3RS)-1-[(S)-1-phenethyl]-5-oxo-3-pyrrolidine-carboxylic acid.

(3S)-1-[(S)-1-Phenethyl]-3-(hydroxymethyl)pyrrolidine

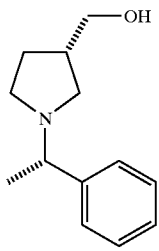

A suspension (3S)-1-[(S)-1-phenethyl]-5-oxo-3-pyrrolidine-carboxylic acid (82.30 g, 352.8 mmol) in Et₂O (200 mL) was added in small portions to a slurry of LiAlH₄ (17.41 g, 458.6 mmol) in Et₂O (700 mL). The mixture began to reflux during the addition. The addition funnel containing the suspension was rinsed with Et₂O (2×50 mL), and the mixture was heated in a 50° C. oil bath for an additional 2 h and first allowed to cool to rt and then further cooled using an ice bath. The mixture was carefully treated with H₂O (62 mL). The resulting precipitate was filtered, rinsed with Et₂O, and discarded. The filtrate was concentrated to a yellow oil. When EtOAc was added to the oil, a solid began to form. Hexane was then added and removed by filtration and dried to afford 43.3 g as a white solid. $[\alpha]^{25}_D = -71$ (c 0.94, CHCl₃). MS (EI) m/z 205 (M⁺), 191, 190, 128, 105, 91, 86, 84, 79, 77, 51.

(3R)-1-[(S)-1-Phenethyl]-3-(cyanomethyl)pyrrolidine

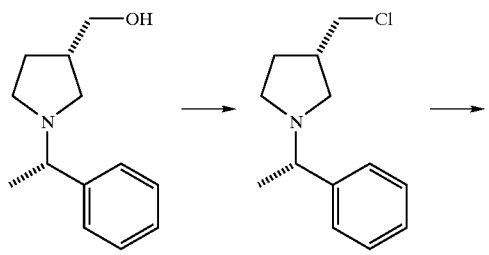

A solution of (3S)-1-[(S)-1-phenethyl]-3-(hydroxymethyl)pyrrolidine (42.75 g, 208.23 mmol) in chloroform (350 mL) was heated to reflux under N₂. The solution was treated with a solution of thionyl chloride (41.8 mL, 573 mmol) in chloroform (40 mL) dropwise over 45 min. The mixture stirred for an additional 30 min, was cooled and concentrated. The residue was diluted with H₂O (~200 mL), 1 N NaOH was added until a pH ~8 (pH paper). A small portion (~50 mL) of sat. NaHCO₃ was added and the basic mixture was extracted with EtOAc (3×400 mL), washed with brine, dried (MgSO₄), filtered and concentrated to give 46.51 g of a red-orange oil for (3S)-1-[(S)-1-phenethyl]-3-(chloromethyl)pyrrolidine: R_f: 0.50 (EtOAc-hexane 1:1); MS (ESI+) m/z 224.2 (MH⁺). The chloride (46.35 g, 208.0 mmol) was transferred to a flask, dimethyl sulfoxide (200 mL) was added, and the solution was treated with NaCN (17.84 g, 363.9 mmol). The mixture was heated under N₂ in a 100° C. oil bath overnight and was cooled. The brown mixture was poured into H₂O (300 mL) and extracted with EtOAc (1000 mL in portions). The combined organic layer was washed with H₂O (6x~50 mL), brine (~100 mL), dried (MgSO₄), filtered and concentrated to give 40.61 g as an orange-red oil: R_f: 0.40 (EtOAc-PhCH₃ 1:1). MS (ESI+) for m/z 215.2 (M+H⁺).

(3R)-Methyl 1-[(S)-1-phenylethyl]pyrrolidine-3-acetate

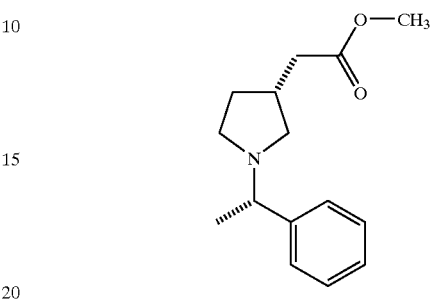

Acetyl chloride (270 mL, 3.8 mol) was carefully added to a flask containing chilled (0° C.) methanol (1100 mL). After the addition was complete, the acidic solution stirred for 45 min (0° C.) and then (3R)-1-[(S)-1-phenethyl]-3-(cyanomethyl)pyrrolidine (40.50 g, 189.0 mmol) in methanol (200 mL) was added. The ice bath was removed and the mixture stirred for 100 h at rt. The resulting suspension was concentrated. Water (~600 mL) was added, the mixture stirred for 45 min and then the pH was adjusted (made basic) through the addition of ~700 mL sat. aq. NaHCO₃. The mixture was extracted with EtOAc (3×300 mL). The combined organics were washed with brine, dried (MgSO₄), filtered through celite and concentrated to give 36.86 g as an orange-red oil. MS (ESI+) m/z 248.2 (M+H⁺).

(5R)-1-Azabicyclo[3.2.1]octan-3-one hydrochloride

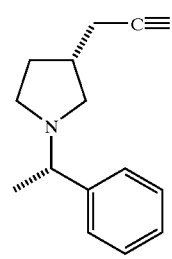

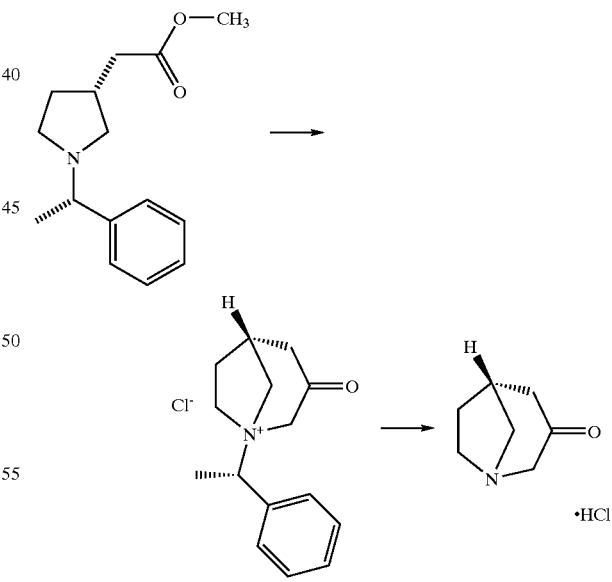

A solution of (3R)-methyl 1-[(S)-1-phenylethyl]pyrrolidine-3-acetate (25.72 g, 104.0 mmol) in THF (265 mL) was cooled under N₂ in a CO₂/acetone bath. Next, ICH₂Cl (22.7 mL, 312.0 mmol) was added, and the mixture stirred for 30 min. A solution of 2.0M lithium diisopropylamide (heptane/THF/ethylbenzene, 156 mL, 312 mmol) was added slowly over 30 min. The internal temperature reached a maximum of −40° C. during this addition. After 1 h, sat. NH₄Cl (100 mL) was added and the mixture was allowed to warm to rt. The organic layer was separated, dried (MgSO₄), filtered and concentrated. The resulting red-brown foam was chromatographed (300 g SiO₂, CHCl₃—MeOH—NH₄OH (89:10:1) followed by CHCl₃—MeOH (3:1). The product fractions were pooled and concentrated to afford (5R)-3-oxo-1-[(1S)-1-phenylethyl]-1-azoniabicyclo[3.2.1]octane chloride (10.12 g) as a tan foam (MS (ESI+) m/z 230.1 (M+H⁺). This foam (10.1 g, 38 mmol) was taken up in MeOH (500 mL), 10% Pd(C) (3.0 g) added and the mixture was hydrogenated (45 psi) overnight. The mixture was filtered and re-subjected to the reduction conditions (9.1 g, 10% Pd/C, 50 psi). After 5 h, TLC indicated the consumption of the (5R)-3-oxo-1-[(1S)-1-phenylethyl]-1-azoniabicyclo[3.2.1]octane chloride. The mixture was filtered, concentrated and triturated (minimal iPrOH) to give 3.73 g of (5R)-1-azabicyclo[3.2.1]octan-3-one hydrochloride, in two crops, as an off-white solid: $[\alpha]^{25}_D$=33 (c 0.97, DMSO). MS (EI) m/z 125 (M⁺).

(3R,5R)-1-azabicyclo[3.2.1]octan-3-amine dihydrochloride

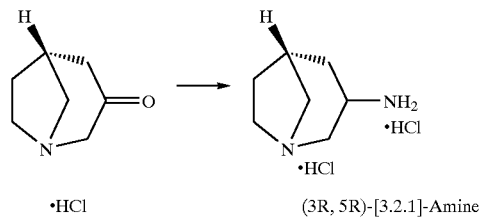

To a flask containing (5R)-1-azabicyclo[3.2.1]octan-3-one hydrochloride (3.64 g, 22.6 mmol), hydroxylamine hydrochloride (2.04 g, 29.4 mmol), and ethanol (130 mL) was added sodium acetate trihydrate (9.23 g, 67.8 mmol). The mixture stirred for 3 h and was filtered and concentrated. The resulting white solid was taken up in n-propanol (100 mL) and sodium (~13.6 g, 618 mmol) was added over 20–25 portions. The reaction spontaneously began to reflux, and the reaction was heated in an oil bath (100° C.). The addition was complete in ~20 min and the mixture had solidified after ~40 min. The oil bath was removed and n-propanol (2×25 mL) was added dissolving the remaining sodium metal. The mixture was carefully quenched through the dropwise addition of H₂O (100 mL). Saturated aq. NaCl (20 mL) was added, and the layers were separated. The organic layer was dried (MgSO₄), filtered, treated with freshly prepared MeOH/HCl, and concentrated. The resulting solid was triturated with 30 mL EtOH, filtered and dried in vaccuo to afford 3.51 g as a white solid: $[\alpha]^{25}_D$=−3 (c 0.94, DMSO). MS (FAB) m/z 127 (MH⁺).

Preparation of endo-1-azabicyclo[3.2.1]octan-3-amine dihydrochloride (endo-[3.2.1]-Amine)

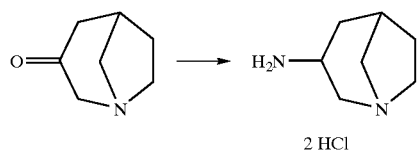

A mixture of 1-azabicyclo[3.2.1]octan-3-one hydrochloride (2.80 g, 17.3 mmol), ethanol (25 mL), and hydroxylamine hydrochloride (1.56 g, 22.4 mmol) is treated with sodium acetate trihydrate (7.07 g, 51.2 mmol). The mixture is stirred for 3 h and evaporated in vacuo. The residue is diluted with CH₂Cl₂, treated with charcoal, filtered and evaporated. The resulting oxime (3.1 mmol) is treated with acetic acid (30 mL) and hydrogenated at 50 psi over PtO₂ (50 mg) for 12 h. The mixture is then filtered and evaporated. The residue is taken up in a minimal amount of water (6 mL) and the pH is adjusted to >12 using solid NaOH. The mixture is then extracted with ethyl acetate (4×25 mL), dried (MgSO₄), filtered, treated with ethereal HCl, and evaporated to give the give endo-[3.2.1]-Amine.

Preparation of the 3.2.2 Amines

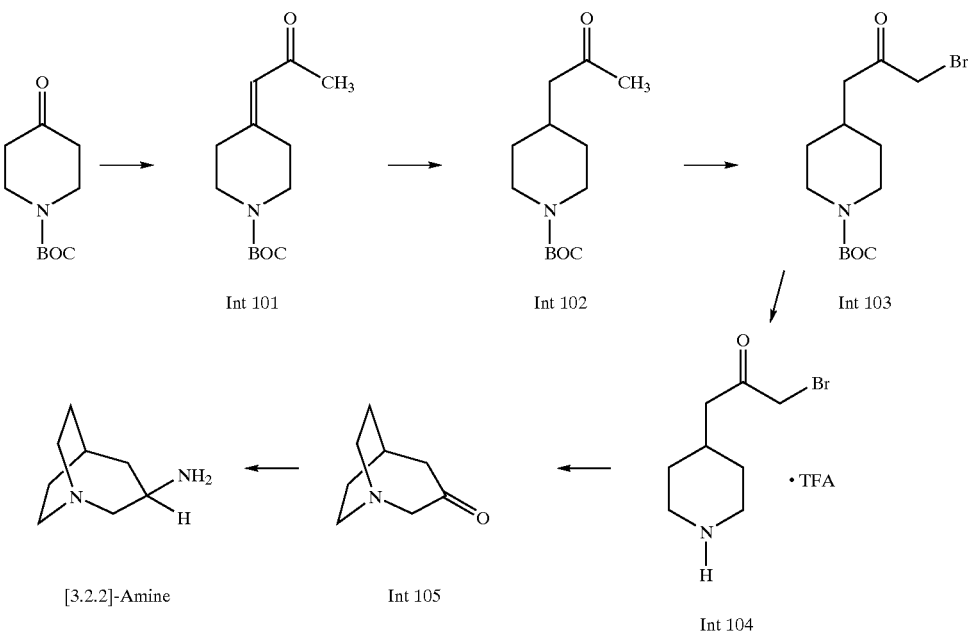

Preparation of tert-butyl 4-(2-oxopropylidene)piperidine-1-carboxylate (Int 101):

Sodium hydride (60% oil dispersion, 2.01 g, 50.2 mmol) is washed with pentane (3×) and suspended in dry THF (40 mL). The solution is cooled to 0° C. before diethyl(2-oxopropyl)phosphonate (9.75 g, 50.2 mmol) is added dropwise. After complete addition, the solution is warmed to rt and stirred for 30 min. tert-Butyl 4-oxo-1-piperidinecarboxylate (5.0 g, 25.1 mmol) is added in portions over 10 min, followed by stirring at rt for 2 h. A saturated aqueous solution of ammonium chloride is added, followed by dilution with ether. The organic layer is extracted with water. The organic layer is dried over anhydrous MgSO$_4$, filtered and concentrated to a yellow oil. The crude product is purified by flash chromatography on silica gel. Elution with hexanes-ether (60:40) gave 4.5 g (75%) of Int 101 as a white solid: $^1$H NMR (400 MHz, CDCl$_3$) δ 6.2, 3.5, 3.4, 2.9, 2.3, 2.2, 1.5.

Preparation of tert-butyl 4-(2-oxopropyl)piperidine-1-carboxylate (Int 102):

A mixture of Int 101 (4.5 g, 19 mmol) and 10% palladium on activated carbon (450 mg) in EtOH (150 mL) is placed in a Parr bottle and hydrogenated for 5 h at 50 psi. The mixture is filtered through Celite, and the filtrate is concentrated in vacuo to afford 4.3 g (94%) of Int 102 as a clear oil: $^1$H NMR (400 MHz, CDCl$_3$) δ 4.1, 2.8, 2.4, 2.2, 2.0, 1.7, 1.5, 1.1.

Preparation of tert-butyl 4-(3-bromo-2-oxopropyl)piperidine-1-carboxylate (Int 103):

To a stirred solution lithium hexamethyldisilylamide in THF (20.0 mL, 1.0 M) in a −78° C. bath is added chlorotrimethylsilane (11.0 mL, 86.4 mmol) dropwise. The mixture is stirred at −78° C. for 20 min, followed by addition of Int 102 (3.21 g, 13.3 mmol) in a solution of THF (50 mL) dropwise. After complete addition, the mixture is stirred at −78° C. for 30 min. The mixture is warmed to 0° C. in an ice-water bath and phenyltrimethylammonium tribromide (5.25 g, 14.0 mmol) is added. The mixture is stirred in an ice-bath for 30 min, followed by the addition of water and ether. The aqueous layer is washed with ether, and the combined organic layers are washed with saturated aqueous sodium thiosulfate solution. The organic layer is dried over anhydrous MgSO$_4$, filtered and concentrated in vacuo to afford a yellow oil. The crude product is purified by flash chromatography on silica gel. Elution with hexanes-ether (60:40) gave 2.2 g (52%) of Int 103 as a lt. yellow oil: $^1$H NMR (400 MHz, CDCl$_3$) δ 4.2–4.1, 3.9, 2.8, 2.7, 2.6, 2.1–2.0, 1.7, 1.5, 1.2–1.1.2.

Preparation of 1-bromo-3-piperidin-4-ylacetone trifluoroacetate (Int 104):

To a stirred solution of Int 103 (2.2 g, 6.9 mmol) in CH$_2$Cl$_2$ (30 mL) in an ice-water bath is added trifluoroacetic acid (10 mL, 130 mmol). The mixture is stirred at 0° C. for 30 min. The volatiles are removed in vacuo to afford 2.0 g (87%) of Int 104 as a yellow residue: MS (ESI) for C$_8$H$_{15}$BrNO [M+H] m/e 220.

Preparation of 1-azabicyclo[3.2.2]nonan-3-one (Int 105):

To a stirred solution of DIEA (13 mL) in acetonitrile (680 mL) at reflux temperature is added a solution of Int 104 (2.0 g, 6.0 mmol) in acetonitrile (125 mL) over a 4 h period via syringe pump. The mixture is kept at reflux temperature overnight. The mixture is concentrated in vacuo and the remaining residue is partitioned between a saturated aqueous K$_2$CO$_3$ solution and CHCl$_3$—MeOH (90:10). The aqueous layer is extracted with CHCl$_3$—MeOH (90:10), and the combined organic layers are dried (MgSO$_4$), filtered and concentrated in vacuo to a brown oil. The crude product is purified by flash chromatography on silica gel. Elution with CHCl$_3$—MeOH—NH$_4$OH 95:4.5:0.5) gives 600 mg (72%) of Int 105 as a clear solid: $^1$H NMR (400 MHz, CDCl$_3$) δ 3.7, 3.3–3.2, 3.1–3.0, 2.7, 2.3, 2.0–1.8.

Preparation of 1-azabicyclo[3.2.2]nonan-3-amine bis(4-methylbenzenesulfonate) ([3.2.2]-Amine)

To a stirred mixture of Int 105 (330 mg, 2.4 mmol) and sodium acetate.trihydrate (670 mg, 4.8 mmol) in EtOH (6.0 mL) is added hydroxylamine.hydrochloride (200 mg, 2.8 mmol). The mixture is stirred at rt for 10 h. The mixture is filtered and the filtrate is concentrated in vacuo to a yellow solid. To a solution of the solid (350 mg, 2.3 mmol) in n-propanol (30 mL) at reflux temperature is added sodium metal (2.0 g, 87 mmol) in small portions over 30 min. Heating at reflux is continued for 2 h. The solution is cooled to rt and brine is added. The mixture is extracted with n-propanol, and the combined organic layers are concentrated in vacuo. The residue is taken up in CHCl$_3$ and the remaining solids are filtered. The filtrate is dried over anhydrous MgSO$_4$, filtered and concentrated in vacuo to a clear solid. To a stirred solution of the solid (320 mg, 2.3 mmol) in EtOH (4 mL) is added p-toluenesulfonic acid monohydrate (875 mg, 4.6 mmol). The solution is warmed in a water bath to 45° C. for 30 min, followed by concentration of the solvent to afford 710 mg (62%) of [3.2.2]-Amine as a white solid: $^1$H NMR (400 MHz, CD$_3$OD) δ 7.7, 7.3, 4.1–3.9, 3.6–3.4, 2.6–2.5, 2.4, 2.2–2.1, 2.1–2.0, 1.9.

Resolution of stereoisomers

The amine can be coupled to form the appropriate amides as a racemic mixture. The racemic mixture can then be resolved by chromatography using chiral columns or chiral HPLC, techniques widely known in the art, to provide the requisite resolved enantiomers 3(R) and 3(S) of said amides.

Coupling

The examples provided are carried out using one amine. However, any of the amine isomers may be used making non-critical changes but starting with the amine not identified. Thus, the stereospecificity of the resulting compound may not drawn. But, the scope of this invention includes the different stereoisomers as described herein as well as racemic mixtures.

EXAMPLE 1 exo-N-[(4S)-1-azabicyclo[2.2.1]hept-3-yl]-4-(4-hydroxyphenoxy)benzamide

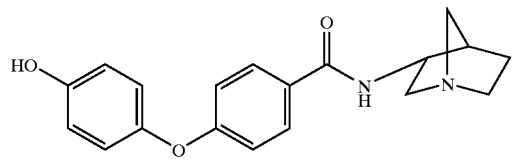

Acetylchloride (1.5 mL, 21 mmol) is added to a solution of 4-(4-hydroxyphenoxy)benzoic acid (2.3 g, 10 mmol) and TEA (2.9 mL, 21 mmol) in CH$_2$Cl$_2$ (50 mL). The reaction is stirred for 16 hours at room temperature. The reaction mixture is diluted with CH$_2$Cl$_2$ and washed three times with saturated NaHCO$_3$. The organic layer is dried (MgSO$_4$), filtered and concentrated in vacuo. The resulting material is dissolved in dioxane (6 mL). Aqueous LiOH (1N, 930 μL) is added, and the reaction is allowed to stir for one hour at room temperature. The reaction mixture is poured into CH$_2$Cl$_2$ and washed twice with KHSO$_4$. The organic layer is dried (MgSO$_4$), filtered and concentrated in vacuo to give 4-(4-acetoxyphenoxy)benzoic acid (1.5 g, 87%). $^1$H NMR (300 MHz, DMSO) δ 12.80, 7.96, 7.23–7.13, 7.04, 2.29.

Coupling: 4-(4-Acetoxyphenoxy)benzoic acid can be coupled with exo-[2.2.1]-Amine using conditions described herein.

EXAMPLE 2 exo-N-[(4S)-1-azabicyclo[2.2.1]hept-3-yl]-4-(4-acetamidophenoxy)benzamide

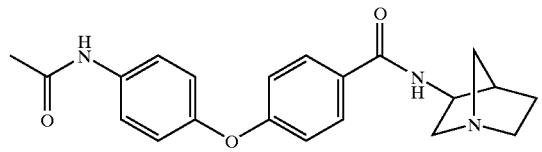

Dry air is bubbled through a solution of 4-acetamidophenol (320 mg, 2.1 mmol), copper(II) acetate (384 mg, 2.1 mmol), TEA (1.5 mL, 10.5 mol), (4-methoxycarbonylphenyl)boronic acid (760 mg, 4.2 mmol), and powdered molecular sieves (2 g) in CH$_2$Cl$_2$ (21 mL) for 16 hours at room temperature. The resulting material is concentrated and purified by flash column chromatography (25–50% EtOAc in heptane) to give methyl 4-(4-acetamidophenoxy)benzoate (450 mg, 75%). $^1$H NMR (300 MHz, DMSO) δ 8.01, 7.54, 7.27, 7.05, 6.98, 3.92, 2.22.

Aqueous LiOH (1M, 3.12 mL) is added to a suspension of methyl 4-(4-acetamidophenoxy)benzoate (445 mg, 1.6 mmol) in dioxane (6 mL). The reaction is stirred for 90 minutes at room temperature. Concentrated HCl (1.5 mL) is added to lower the pH to less than 6 and the resulting precipitate is collected by filtration. The filter cake is washed with water then dried to give 4-(4-acetamidophenoxy) benzoic acid (337 mg, 80%). MS for C$_{15}$H$_{13}$NO$_4$ (ESI) (M–H)$^-$ m/z 270.

Coupling: 4-(4-Acetamidophenoxy)benzoic acid can be coupled with exo-[2.2.1]-Amine using conditions described herein.

EXAMPLE 3 exo-N-[(4S)-1-azabicyclo[2.2.1]hept-3-yl]-4-phenoxybenzamide

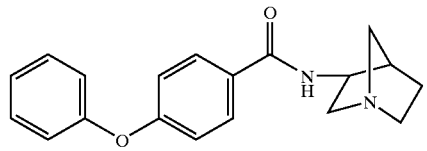

4-Phenoxybenzoic acid can be coupled with exo-[2.2.1]-Amine using conditions described herein.

The following compounds can be made from the coupling carboxylic acids with exo-[2.2.1]-Amine using conditions described herein.

EXAMPLE 4 exo-N-[(4S)-1-azabicyclo[2.2.1]hept-3-yl]-4-benzylbenzamide (from 4-benylbenzoic acid)

EXAMPLE 5 exo-N-[(4S)-1-azabicyclo[2.2.1]hept-3-yl]-4-(phenylsulfanyl)-benzamide, (from 4-(phenylsulfanyl)benzoic acid)

EXAMPLE 6 exo-N-[(4S)-1-azabicyclo[2.2.1]hept-3-yl]-3-phenoxybenzamide (from 3-phenoxybenzoic acid)

EXAMPLE 7 exo-N-[(4S)-1-azabicyclo[2.2.1]hept-3-yl]-4-benzoylbenzamide (from 4-benzoylbenzoic acid)

EXAMPLE 8 exo-N-[(4S)-1-azabicyclo[2.2.1]hept-3-yl]-4-(4-fluorophenoxy)benzamide

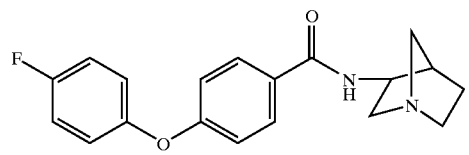

To a flask with 4-fluorophenyl boronic acid (2.1 g, 15 mmol), copper(II) acetate (1.4 g, 7.5 mmol), activated powdered molecular sieves (approximately 2 g), and methyl 4-hydroxybenzoate (1.2 g, 7.5 mmol) is added TEA (5.2 mL, 38 mmol) followed by CH$_2$Cl$_2$ (75 mL). The reaction is stirred for 16 hours at room temperature with air bubbling through it. The reaction mixture is diluted with CH$_2$Cl$_2$ and filtered through silica gel. The silica gel is washed with EtOAc-heptane. The solution is concentrated in vacuo and dissolved in dioxane (15 mL). To this solution is added aqueous LiOH (1N, 15 mL) and stirred for 18 hours at room temperature. To this reaction mixture is added aqueous HCl (1N) until acidic, having a pH less than 6. The resulting precipitate is collected by filtration and rinsed with water, and dried in vacuo to give 4-(4-fluorophenoxy)benzoic acid (1.6 g, 90%). MS for C$_{13}$H$_9$FO$_3$ (ESI) (M–H)$^-$ m/z 231.

Coupling 4-(4-Fluorophenoxy)benzoic acid can be coupled with exo-[2.2.1]-Amine using conditions described herein.

Example 9 can be made from coupling the boronic acid with exo-[2.2.1]-Amine using conditions described herein:

EXAMPLE 9 exo-N-[(4S)-1-azabicyclo[2.2.1]hept-3-yl]-4-(2-fluorophenoxy)-benzamide (from 2-fluorophenylboronic acid)

EXAMPLE 10 exo-N-[(4S)-1-azabicyclo[2.2.1]hept-3-yl]-4-(3-fluorophenoxy)-benzamide 4-methylbenzenesulfonate (from 3-fluorophenylboronic acid)

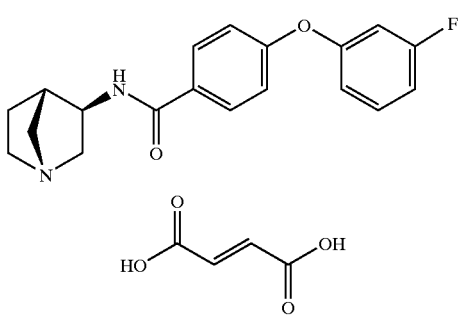

To a stirred solution of 4-(3-fluorophenoxy)benzoic acid (116 mg, 0.5 mmol) in anhydrous DMF (10 mL) are added DIEA (265 μL, 1.52 mmol) and exo-(4S)-[2.2.1]-Amine (228 mg, 0.5 mmol). The mixture is cooled to 0° C., and HATU (190 mg, 0.5 mmol) is added in one portion. The reaction mixture is allowed to warm to room temperature and stir overnight. The solvent is removed in vacuo and the residue is partitioned between saturated aqueous $K_2CO_3$ solution and chloroform. The aqueous layer is extracted with chloroform (2×). The combined organic layers are washed with brine, dried ($Na_2SO_4$), filtered and concentrated in vacuo. The crude product is purified by flash chromatography on silica gel. Elution with chloroform-methanol-ammonium hydroxide (89:9:1) gives the product as a yellow solid (164 mg, 99%).

To a stirred solution of the above amide (164 mg, 0.50 mmol) in methanol (5 mL) is added a warm solution of para-toluenesulfonic acid monohydrate (95 mg, 0.50 mmol) in methanol (5 mL). The mixture is stirred for 10 min at 50° C. The solvent is removed in vacuo and the remaining residue is diluted with acetone (5 mL). The mixture is stirred overnight at room temperature. The solid is collected by filtration, washed with acetone, and drying under high vacuum overnight gives 200 mg (77%) of the title compound as a white solid: $^1$H NMR (400 MHz, $CD_3OD$) δ 7.9, 7.7, 7.4, 7.2, 7.1, 7.0–6.8, 4.2, 3.8, 3.5–3.3, 3.3–3.2, 3.1, 2.4, 2.2, 1.9.

The following examples can be made from coupling the boronic acids with exo-[2.2.1]-Amine using conditions described herein:

EXAMPLE 11 exo-N-[(4S)-1-azabicyclo[2.2.1]hept-3-yl]-4-(2-chlorophenoxy)-benzamide (from 2-chlorophenylboronic acid)

EXAMPLE 12 exo-N-[(4S)-1-azabicyclo[2.2.1]hept-3-yl]-4-(3-chlorophenoxy)-benzamide (from 3-chlorophenylboronic acid)

EXAMPLE 13 exo-N-[(4S)-1-azabicyclo[2.2.1]hept-3-yl]-4-(4-chlorophenoxy)-benzamide (from 4-chlorophenylboronic acid)

EXAMPLE 14 exo-N-[(4S)-1-azabicyclo[2.2.1]hept-3-yl]-4-(2-methoxyphenoxy)-benzamide (from 2-methoxyphenylboronic acid)

EXAMPLE 15 exo-N-[(4S)-1-azabicyclo[2.2.1]hept-3-yl]-4-(3-methoxyphenoxy)-benzamide (from 3-methoxyphenylboronic acid)

EXAMPLE 16 exo-N-[(4S)-1-azabicyclo[2.2.1]hept-3-yl]-4-(4-methoxyphenoxy)-benzamide (from 4-methoxyphenylboronic acid)

EXAMPLE 17 exo-N-[(4S)-1-azabicyclo[2.2.1]hept-3-yl]-4-(3-chlorophenylsulfanyl)-benzamide

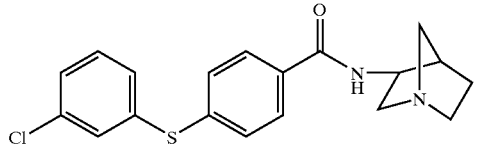

A flask containing 3-chlorothiophenol (0.29 mL, 2.5 mmol), potassium tert-butoxide (0.28 g, 2.5 mmol), tetrakis(triphenylphosphine)palladium (0) (0.23 g, 0.2 mmol), and methyl 4-iodobenzoate (0.66 g, 2.5 mmol) is vacuum purged and $N_2$ filled three times. To this flask is added THF (50 mL) and the mixture is stirred at reflux for 24 hours. The solution is diluted with $CH_2Cl_2$ and extracted three times with 1N NaOH. The organic layer is dried ($MgSO_4$) and concentrated in vacuo. The crude product is purified by flash-column chromatography (gradient of 0–1% EtOAc in heptane) to give methyl 4-(3-chlorosulfanyl)benzoate (0.53 g, 90%). $^1$H NMR (300 MHz, $CDCl_3$) δ 7.96, 7.44–7.43, 7.34–7.29, 3.92.

Methyl 4-(3-chlorosulfanyl)benzoate (0.53 g, 1.89 mmol) is dissolved in dioxane (4 mL) followed by addition of aqueous LiOH (1M, 4 mL). The mixture is stirred at room temperature for 5 hours then acidified with aqueous 1N HCl to a pH of less than 6. The resulting precipitate is collected by filtration, rinsed with water, and dried in vacuo to give 4-(3-chlorosulfanyl)benzoic acid(0.44 g, 89%). MS for $C_{13}H_9ClO_2S$ (ESI) (M–H)$^-$ m/z 263.

Coupling 4-(3-Chlorosulfanyl)benzoic acid can be coupled with exo-[2.2.1]-Amine using conditions described herein.

The following compounds can be made by coupling the thiophenols with exo-[2.2.1]-Amine using conditions described herein.

EXAMPLE 18 exo-N-[(4S)-1-azabicyclo[2.2.1]hept-3-yl]-4-(4-chlorophenyl-sulfanyl)benzamide (from 4-chlorothiophenol)

EXAMPLE 19 exo-N-[(4S)-1-azabicyclo[2.2.1]hept-3-yl]-4-(2-chlorophenyl-sulfanyl)benzamide (from 2-chlorothiophenol)

EXAMPLE 20 exo-N-[(4S)-1-azabicyclo[2.2.1]hept-3-yl]-4-(4-methoxyphenyl-sulfanyl)benzamide (from 4-methoxythiophenol)

EXAMPLE 21 exo-N-[(4S)-1-azabicyclo[2.2.1]hept-3-yl]-4-(3-methoxyphenyl-sulfanyl)benzamide (from 3-methoxythiophenol)

EXAMPLE 22 exo-N-[(4S)-1-azabicyclo[2.2.1]hept-3-yl]-4-(2-methoxyphenyl-sulfanyl)benzamide (from 2-methoxythiophenol)

The present invention also includes, by representation but not limitation, any one or more or combinantion of the following compounds and pharmaceutically acceptable salts thereof, both of which can be made by one of ordinary skill in the art using the procedures provided making non-critical changes:

N-[6-methyl-1-azabicyclo[2.2.2]oct-3-yl]-4-(4-hydroxyphenoxy)benzamide;
N-[6-methyl-1-azabicyclo[2.2.2]oct-3-yl]-4-(4-acetamidophenoxy)benzamide;
N-[6-methyl-1-azabicyclo[2.2.2]oct-3-yl]-4-phenoxybenzamide;
N-[6-methyl-1-azabicyclo[2.2.2]oct-3-yl]-4-benzylbenzamide;
N-[6-methyl-1-azabicyclo[2.2.2]oct-3-yl]-4-(phenylsulfanyl)-benzamide;
N-[6-methyl-1-azabicyclo[2.2.2]oct-3-yl]-3-phenoxybenzamide;
N-[6-methyl-1-azabicyclo[2.2.2]oct-3-yl]-4-(4-fluorophenoxy)benzamide;
N-[6-methyl-1-azabicyclo[2.2.2]oct-3-yl]-4-(2-fluorophenoxy)-benzamide;
N-[6-methyl-1-azabicyclo[2.2.2]oct-3-yl]-4-(3-fluorophenoxy)-benzamide;
N-[6-methyl-1-azabicyclo[2.2.2]oct-3-yl]-4-(2-chlorophenoxy)-benzamide;
N-[6-methyl-1-azabicyclo[2.2.2]oct-3-yl]-4-(3-chlorophenoxy)-benzamide;
N-[6-methyl-1-azabicyclo[2.2.2]oct-3-yl]-4-(4-chlorophenoxy)-benzamide;
N-[6-methyl-1-azabicyclo[2.2.2]oct-3-yl]-4-(2-methoxyphenoxy)-benzamide;
N-[6-methyl-1-azabicyclo[2.2.2]oct-3-yl]-4-(3-methoxyphenoxy)-benzamide;
N-[6-methyl-1-azabicyclo[2.2.2]oct-3-yl]-4-(4-methoxyphenoxy)-benzamide;
N-[6-methyl-1-azabicyclo[2.2.2]oct-3-yl]-4-(3-chlorophenylsulfanyl)benzamide;
N-[6-methyl-1-azabicyclo[2.2.2]oct-3-yl]-4-(4-chlorophenyl-sulfanyl)benzamide;
N-[6-methyl-1-azabicyclo[2.2.2]oct-3-yl]-4-(2-chlorophenyl-sulfanyl)benzamide;
N-[6-methyl-1-azabicyclo[2.2.2]oct-3-yl]-4-(4-methoxyphenyl-sulfanyl)benzamide;
N-[6-methyl-1-azabicyclo[2.2.2]oct-3-yl]-4-(3-methoxyphenyl-sulfanyl)benzamide;
N-[6-methyl-1-azabicyclo[2.2.2]oct-3-yl]-4-(2-methoxyphenyl-sulfanyl)benzamide;
N-[6-methyl-1-azabicyclo[2.2.2]oct-3-yl]-4-(4-aminophenoxy)-benzamide;
N-[6-methyl-1-azabicyclo[2.2.2]oct-3-yl]-4-(3-aminophenoxy)-benzamide;
N-[6-methyl-1-azabicyclo[2.2.2]oct-3-yl]-4-(2-aminophenoxy)-benzamide;
N-[6-methyl-1-azabicyclo[2.2.2]oct-3-yl]-4-(4-acetylphenoxy)-benzamide;
N-[6-methyl-1-azabicyclo[2.2.2]oct-3-yl]-4-(3-acetylphenoxy)-benzamide;
N-[6-methyl-1-azabicyclo[2.2.2]oct-3-yl]-4-(2-acetylphenoxy)-benzamide;
N-[6-methyl-1-azabicyclo[2.2.2]oct-3-yl]-4-(4-carbamoylphenoxy)-benzamide;
N-[6-methyl-1-azabicyclo[2.2.2]oct-3-yl]-4-(3-carbamoylphenoxy)-benzamide;
N-[6-methyl-1-azabicyclo[2.2.2]oct-3-yl]-4-(2-carbamoylphenoxy)-benzamide;
N-[6-methyl-1-azabicyclo[2.2.2]oct-3-yl]-4-(4-cyanophenoxy)-benzamide;
N-[6-methyl-1-azabicyclo[2.2.2]oct-3-yl]-4-(3-cyanophenoxy)-benzamide;
N-[6-methyl-1-azabicyclo[2.2.2]oct-3-yl]-4-(2-cyanophenoxy)-benzamide;
N-[6-methyl-1-azabicyclo[2.2.2]oct-3-yl]-4-(thiophen-2-yloxy)-benzamide;
N-[6-methyl-1-azabicyclo[2.2.2]oct-3-yl]-4-(5-methylthiophen-2-yloxy)-benzamide;
N-[6-methyl-1-azabicyclo[2.2.2]oct-3-yl]-4-(5-chlorothiophen-2-yloxy)-benzamide;
N-[6-methyl-1-azabicyclo[2.2.2]oct-3-yl]-4-(5-methoxythiophen-2-yloxy)-benzamide;
N-[6-methyl-1-azabicyclo[2.2.2]oct-3-yl]-4-(5-trifluoromethylthiophen-2-yloxy)-benzamide;
N-[6-methyl-1-azabicyclo[2.2.2]oct-3-yl]-4-(4-methylthiophen-2-yloxy)-benzamide;
N-[6-methyl-1-azabicyclo[2.2.2]oct-3-yl]-4-(4-chlorothiophen-2-yloxy)-benzamide;
N-[6-methyl-1-azabicyclo[2.2.2]oct-3-yl]-4-(4-methoxythiophen-2-yloxy)-benzamide;
N-[6-methyl-1-azabicyclo[2.2.2]oct-3-yl]-4-(4-trifluoromethylthiophen-2-yloxy)-benzamide;
N-[6-methyl-1-azabicyclo[2.2.2]oct-3-yl]-4-(furan-2-yloxy)-benzamide;
N-[6-methyl-1-azabicyclo[2.2.2]oct-3-yl]-4-(5-methylfuran-2-yloxy)-benzamide;
N-[6-methyl-1-azabicyclo[2.2.2]oct-3-yl]-4-(5-chlorofuran-2-yloxy)-benzamide;
N-[6-methyl-1-azabicyclo[2.2.2]oct-3-yl]-4-(5-methoxyfuran-2-yloxy)-benzamide;
N-[6-methyl-1-azabicyclo[2.2.2]oct-3-yl]-4-(5-trifluoromethylfuran-2-yloxy)-benzamide;

N-[6-methyl-1-azabicyclo[2.2.2]oct-3-yl]-4-(4-methylfuran-2-yloxy)-benzamide;
N-[6-methyl-1-azabicyclo[2.2.2]oct-3-yl]-4-(4-chlorofuran-2-yloxy)-benzamide;
N-[6-methyl-1-azabicyclo[2.2.2]oct-3-yl]-4-(4-methoxyfuran-2-yloxy)-benzamide;
N-[6-methyl-1-azabicyclo[2.2.2]oct-3-yl]-4-(4-trifluoromethylfuran-2-yloxy)-benzamide;
N-[6-methyl-1-azabicyclo[2.2.2]oct-3-yl]-4-(oxazol-2-yloxy)-benzamide;
N-[6-methyl-1-azabicyclo[2.2.2]oct-3-yl]-4-(oxazol-5-yloxy)-benzamide;
N-[6-methyl-1-azabicyclo[2.2.2]oct-3-yl]-4-(thiazol-2-yloxy)-benzamide;
N-[6-methyl-1-azabicyclo[2.2.2]oct-3-yl]-4-(thiazol-5-yloxy)-benzamide;
N-[6-methyl-1-azabicyclo[2.2.2]oct-3-yl]-4-([1,3,4]oxadiazol-2-yloxy)-benzamide;
N-[6-methyl-1-azabicyclo[2.2.2]oct-3-yl]-4-([1,3,4]thiadiazol-2-yloxy)-benzamide;
N-[6-methyl-1-azabicyclo[2.2.2]oct-3-yl]-4-(4-aminophenylsulfanyl)-benzamide;
N-[6-methyl-1-azabicyclo[2.2.2]oct-3-yl]-4-(3-aminophenylsulfanyl)-benzamide;
N-[6-methyl-1-azabicyclo[2.2.2]oct-3-yl]-4-(2-aminophenylsulfanyl)-benzamide;
N-[6-methyl-1-azabicyclo[2.2.2]oct-3-yl]-4-(4-acetylphenylsulfanyl)-benzamide;
N-[6-methyl-1-azabicyclo[2.2.2]oct-3-yl]-4-(3-acetylphenylsulfanyl)-benzamide;
N-[6-methyl-1-azabicyclo[2.2.2]oct-3-yl]-4-(2-acetylphenylsulfanyl)-benzamide;
N-[6-methyl-1-azabicyclo[2.2.2]oct-3-yl]-4-(4-carbamoylphenylsulfanyl)-benzamide;
N-[6-methyl-1-azabicyclo[2.2.2]oct-3-yl]-4-(3-carbamoylphenylsulfanyl)-benzamide;
N-[6-methyl-1-azabicyclo[2.2.2]oct-3-yl]-4-(2-carbamoylphenylsulfanyl)-benzamide;
N-[6-methyl-1-azabicyclo[2.2.2]oct-3-yl]-4-(4-hydroxyphenylsulfanyl)-benzamide;
N-[6-methyl-1-azabicyclo[2.2.2]oct-3-yl]-4-(3-hydroxyphenylsulfanyl)-benzamide;
N-[6-methyl-1-azabicyclo[2.2.2]oct-3-yl]-4-(2-hydroxyphenylsulfanyl)-benzamide;
N-[6-methyl-1-azabicyclo[2.2.2]oct-3-yl]-4-(4-acetamidophenylsulfanyl)-benzamide;
N-[6-methyl-1-azabicyclo[2.2.2]oct-3-yl]-4-(3-acetamidophenylsulfanyl)-benzamide;
N-[6-methyl-1-azabicyclo[2.2.2]oct-3-yl]-4-(2-acetamidophenylsulfanyl)-benzamide;
N-[6-methyl-1-azabicyclo[2.2.2]oct-3-yl]-4-(thiophen-2-ylsulfanyl)-benzamide;
N-[6-methyl-1-azabicyclo[2.2.2]oct-3-yl]-4-(5-methylthiophen-2-ylsulfanyl)-benzamide;
N-[6-methyl-1-azabicyclo[2.2.2]oct-3-yl]-4-(5-chlorothiophen-2-ylsulfanyl)-benzamide;
N-[6-methyl-1-azabicyclo[2.2.2]oct-3-yl]-4-(5-trifluoromethylthiophen-2-ylsulfanyl)-benzamide;
N-[6-methyl-1-azabicyclo[2.2.2]oct-3-yl]-4-(furan-2-ylsulfanyl)-benzamide;
N-[6-methyl-1-azabicyclo[2.2.2]oct-3-yl]-4-(5-methylfuran-2-ylsulfanyl)-benzamide;
N-[6-methyl-1-azabicyclo[2.2.2]oct-3-yl]-4-(5-chlorofuran-2-ylsulfanyl)-benzamide;
N-[6-methyl-1-azabicyclo[2.2.2]oct-3-yl]-4-(oxazol-2-ylsulfanyl)-benzamide;
N-[6-methyl-1-azabicyclo[2.2.2]oct-3-yl]-4-(5-chlorooxazol-2-ylsulfanyl)-benzamide;
N-[6-methyl-1-azabicyclo[2.2.2]oct-3-yl]-4-(5-methoxyoxazol-2-ylsulfanyl)-benzamide;
N-[6-methyl-1-azabicyclo[2.2.2]oct-3-yl]-4-(5-trifluoromethyloxazol-2-ylsulfanyl)-benzamide;
N-[6-methyl-1-azabicyclo[2.2.2]oct-3-yl]-4-(oxazol-2-ylsulfanyl)-benzamide;
N-[6-methyl-1-azabicyclo[2.2.2]oct-3-yl]-4-(oxazol-5-ylsulfanyl)-benzamide;
N-[6-methyl-1-azabicyclo[2.2.2]oct-3-yl]-4-(thiazol-2-ylsulfanyl)-benzamide;
N-[6-methyl-1-azabicyclo[2.2.2]oct-3-yl]-4-(thiazol-5-ylsulfanyl)-benzamide;
N-[6-methyl-1-azabicyclo[2.2.2]oct-3-yl]-4-([1,3,4]oxadiazol-2-ylsulfanyl)-benzamide;
N-[6-methyl-1-azabicyclo[2.2.2]oct-3-yl]-4-([1,3,4]thiadiazol-2-ylsulfanyl)-benzamide;
N-[6-methyl-1-azabicyclo[2.2.2]oct-3-yl]-4-(5-trifluoromethylpyrrol-2-yloxy)-benzamide;
N-[6-methyl-1-azabicyclo[2.2.2]oct-3-yl]-4-(3H-imidazol-4-yloxy)-benzamide;
N-[6-methyl-1-azabicyclo[2.2.2]oct-3-yl]-4-(isoxazol-2-yloxy)-benzamide;
N-[6-methyl-1-azabicyclo[2.2.2]oct-3-yl]-4-(isothiazol-2-yloxy)-benzamide;
N-[6-methyl-1-azabicyclo[2.2.2]oct-3-yl]-4-(pyrrol-2-ylsulfanyl)-benzamide;
N-[6-methyl-1-azabicyclo[2.2.2]oct-3-yl]-4-(3H-imidazol-4-ylsulfanyl)-benzamide;
N-[6-methyl-1-azabicyclo[2.2.2]oct-3-yl]-4-(isoxazol-2-ylsulfanyl)-benzamide;
N-[6-methyl-1-azabicyclo[2.2.2]oct-3-yl]-4-(isothiazol-2-ylsulfanyl)-benzamide;
N-[6-methyl-1-azabicyclo[2.2.2]oct-3-yl]-4-(6-methylpyridin-3-yloxy)-benzamide;
N-[6-methyl-1-azabicyclo[2.2.2]oct-3-yl]-4-(6-chloropyridin-3-yloxy)-benzamide;
N-[6-methyl-1-azabicyclo[2.2.2]oct-3-yl]-4-(6-methoxypyridin-3-yloxy)-benzamide;
N-[6-methyl-1-azabicyclo[2.2.2]oct-3-yl]-4-(6-trifluoromethylpyridin-3-yloxy)-benzamide;
N-[6-methyl-1-azabicyclo[2.2.2]oct-3-yl]-4-(2-chloropyridin-4-yloxy)-benzamide;
N-[6-methyl-1-azabicyclo[2.2.2]oct-3-yl]-4-(5-chloropyridin-2-yloxy)-benzamide;
N-[6-methyl-1-azabicyclo[2.2.2]oct-3-yl]-4-(4-chloropyridin-2-yloxy)-benzamide;
N-[6-methyl-1-azabicyclo[2.2.2]oct-3-yl]-4-(6-chloropyridin-2-yloxy)-benzamide;
N-[6-methyl-1-azabicyclo[2.2.2]oct-3-yl]-4-(5-chloropyridin-3-yloxy)-benzamide;
N-[6-methyl-1-azabicyclo[2.2.2]oct-3-yl]-4-(2-chloropyridin-3-yloxy)-benzamide;
N-[6-methyl-1-azabicyclo[2.2.2]oct-3-yl]-4-(4-chloropyridin-3-yloxy)-benzamide;
N-[6-methyl-1-azabicyclo[2.2.2]oct-3-yl]-4-(3-chloropyridin-4-yloxy)-benzamide;
N-[6-methyl-1-azabicyclo[2.2.2]oct-3-yl]-4-(3-chloropyridin-2-yloxy)-benzamide; or
N-[6-methyl-1-azabicyclo[2.2.2]oct-3-yl]-4-(6-chloropyridin-3-ylsulfanyl)-benzamide.

The present invention also includes, by representation but not limitation, any one or more or combination of the following compounds and pharmaceutically acceptable salts thereof, both of which can be made by one of ordinary skill in the art using the procedures provided making non-critical changes:

exo-N-[(4S)-1-azabicyclo[2.2.1]hept-3-yl]-4-(4-hydroxyphenoxy)benzamide;
exo-N-[(4S)-1-azabicyclo[2.2.1]hept-3-yl]-4-(4-acetamidophenoxy)benzamide;
exo-N-[(4S)-1-azabicyclo[2.2.1]hept-3-yl]-4-phenoxybenzamide;
exo-N-[(4S)-1-azabicyclo[2.2.1]hept-3-yl]-4-benzylbenzamide;
exo-N-[(4S)-1-azabicyclo[2.2.1]hept-3-yl]-4-(phenylsulfanyl)-benzamide;
exo-N-[(4S)-1-azabicyclo[2.2.1]hept-3-yl]-3-phenoxybenzamide;
exo-N-[(4S)-1-azabicyclo[2.2.1]hept-3-yl]-4-(4-fluorophenoxy)benzamide;
exo-N-[(4S)-1-azabicyclo[2.2.1]hept-3-yl]-4-(2-fluorophenoxy)-benzamide;
exo-N-[(4S)-1-azabicyclo[2.2.1]hept-3-yl]-4-(3-fluorophenoxy)-benzamide;
exo-N-[(4S)-1-azabicyclo[2.2.1]hept-3-yl]-4-(2-chlorophenoxy)-benzamide;
exo-N-[(4S)-1-azabicyclo[2.2.1]hept-3-yl]-4-(3-chlorophenoxy)-benzamide;
exo-N-[(4S)-1-azabicyclo[2.2.1]hept-3-yl]-4-(4-chlorophenoxy)-benzamide;
exo-N-[(4S)-1-azabicyclo[2.2.1]hept-3-yl]-4-(2-methoxyphenoxy)-benzamide;
exo-N-[(4S)-1-azabicyclo[2.2.1]hept-3-yl]-4-(3-methoxyphenoxy)-benzamide;
exo-N-[(4S)-1-azabicyclo[2.2.1]hept-3-yl]-4-(4-methoxyphenoxy)-benzamide;
exo-N-[(4S)-1-azabicyclo[2.2.1]hept-3-yl]-4-(3-chlorophenylsulfanyl)benzamide;
exo-N-[(4S)-1-azabicyclo[2.2.1]hept-3-yl]-4-(4-chlorophenyl-sulfanyl)benzamide;
exo-N-[(4S)-1-azabicyclo[2.2.1]hept-3-yl]-4-(2-chlorophenyl-sulfanyl)benzamide;
exo-N-[(4S)-1-azabicyclo[2.2.1]hept-3-yl]-4-(4-methoxyphenyl-sulfanyl)benzamide;
exo-N-[(4S)-1-azabicyclo[2.2.1]hept-3-yl]-4-(3-methoxyphenyl-sulfanyl)benzamide;
exo-N-[(4S)-1-azabicyclo[2.2.1]hept-3-yl]-4-(2-methoxyphenyl-sulfanyl)benzamide;
exo-N-[(4S)-1-azabicyclo[2.2.1]hept-3-yl]-4-(4-aminophenoxy)-benzamide;
exo-N-[(4S)-1-azabicyclo[2.2.1]hept-3-yl]-4-(3-aminophenoxy)-benzamide;
exo-N-[(4S)-1-azabicyclo[2.2.1]hept-3-yl]-4-(2-aminophenoxy)-benzamide;
exo-N-[(4S)-1-azabicyclo[2.2.1]hept-3-yl]-4-(4-acetylphenoxy)-benzamide;
exo-N-[(4S)-1-azabicyclo[2.2.1]hept-3-yl]-4-(3-acetylphenoxy)-benzamide;
exo-N-[(4S)-1-azabicyclo[2.2.1]hept-3-yl]-4-(2-acetylphenoxy)-benzamide;
exo-N-[(4S)-1-azabicyclo[2.2.1]hept-3-yl]-4-(4-carbamoylphenoxy)-benzamide;
exo-N-[(4S)-1-azabicyclo[2.2.1]hept-3-yl]-4-(3-carbamoylphenoxy)-benzamide;
exo-N-[(4S)-1-azabicyclo[2.2.1]hept-3-yl]-4-(2-carbamoylphenoxy)-benzamide;
exo-N-[(4S)-1-azabicyclo[2.2.1]hept-3-yl]-4-(4-cyanophenoxy)-benzamide;
exo-N-[(4S)-1-azabicyclo[2.2.1]hept-3-yl]-4-(3-cyanophenoxy)-benzamide;
exo-N-[(4S)-1-azabicyclo[2.2.1]hept-3-yl]-4-(2-cyanophenoxy)-benzamide;
exo-N-[(4S)-1-azabicyclo[2.2.1]hept-3-yl]-4-(thiophen-2-yloxy)-benzamide;
exo-N-[(4S)-1-azabicyclo[2.2.1]hept-3-yl]-4-(5-methylthiophen-2-yloxy)-benzamide;
exo-N-[(4S)-1-azabicyclo[2.2.1]hept-3-yl]-4-(5-chlorothiophen-2-yloxy)-benzamide;
exo-N-[(4S)-1-azabicyclo[2.2.1]hept-3-yl]-4-(5-methoxythiophen-2-yloxy)-benzamide;
exo-N-[(4S)-1-azabicyclo[2.2.1]hept-3-yl]-4-(5-trifluoromethylthiophen-2-yloxy)-benzamide;
exo-N-[(4S)-1-azabicyclo[2.2.1]hept-3-yl]-4-(4-methylthiophen-2-yloxy)-benzamide;
exo-N-[(4S)-1-azabicyclo[2.2.1]hept-3-yl]-4-(4-chlorothiophen-2-yloxy)-benzamide;
exo-N-[(4S)-1-azabicyclo[2.2.1]hept-3-yl]-4-(4-methoxythiophen-2-yloxy)-benzamide;
exo-N-[(4S)-1-azabicyclo[2.2.1]hept-3-yl]-4-(4-trifluoromethylthiophen-2-yloxy)-benzamide;
exo-N-[(4S)-1-azabicyclo[2.2.1]hept-3-yl]-4-(furan-2-yloxy)-benzamide;
exo-N-[(4S)-1-azabicyclo[2.2.1]hept-3-yl]-4-(5-methylfuran-2-yloxy)-benzamide;
exo-N-[(4S)-1-azabicyclo[2.2.1]hept-3-yl]-4-(5-chlorofuran-2-yloxy)-benzamide;
exo-N-[(4S)-1-azabicyclo[2.2.1]hept-3-yl]-4-(5-methoxyfuran-2-yloxy)-benzamide;
exo-N-[(4S)-1-azabicyclo[2.2.1]hept-3-yl]-4-(5-trifluoromethylfuran-2-yloxy)-benzamide;
exo-N-[(4S)-1-azabicyclo[2.2.1]hept-3-yl]-4-(4-methylfuran-2-yloxy)-benzamide;
exo-N-[(4S)-1-azabicyclo[2.2.1]hept-3-yl]-4-(4-chlorofuran-2-yloxy)-benzamide;
exo-N-[(4S)-1-azabicyclo[2.2.1]hept-3-yl]-4-(4-methoxyfuran-2-yloxy)-benzamide;
exo-N-[(4S)-1-azabicyclo[2.2.1]hept-3-yl]-4-(4-trifluoromethylfuran-2-yloxy)-benzamide;
exo-N-[(4S)-1-azabicyclo[2.2.1]hept-3-yl]-4-(oxazol-2-yloxy)-benzamide;
exo-N-[(4S)-1-azabicyclo[2.2.1]hept-3-yl]-4-(oxazol-5-yloxy)-benzamide;
exo-N-[(4S)-1-azabicyclo[2.2.1]hept-3-yl]-4-(thiazol-2-yloxy)-benzamide;
exo-N-[(4S)-1-azabicyclo[2.2.1]hept-3-yl]-4-(thiazol-5-yloxy)-benzamide;
exo-N-[(4S)-1-azabicyclo[2.2.1]hept-3-yl]-4-([1,3,4]oxadiazol-2-yloxy)-benzamide;
exo-N-[(4S)-1-azabicyclo[2.2.1]hept-3-yl]-4-([1,3,4]thiadiazol-2-yloxy)-benzamide;
exo-N-[(4S)-1-azabicyclo[2.2.1]hept-3-yl]-4-(4-aminophenylsulfanyl)-benzamide;
exo-N-[(4S)-1-azabicyclo[2.2.1]hept-3-yl]-4-(3-aminophenylsulfanyl)-benzamide;
exo-N-[(4S)-1-azabicyclo[2.2.1]hept-3-yl]-4-(2-aminophenylsulfanyl)-benzamide;
exo-N-[(4S)-1-azabicyclo[2.2.1]hept-3-yl]-4-(4-acetylphenylsulfanyl)-benzamide;
exo-N-[(4S)-1-azabicyclo[2.2.1]hept-3-yl]-4-(3-acetylphenylsulfanyl)-benzamide;
exo-N-[(4S)-1-azabicyclo[2.2.1]hept-3-yl]-4-(2-acetylphenylsulfanyl)-benzamide;
exo-N-[(4S)-1-azabicyclo[2.2.1]hept-3-yl]-4-(4-carbamoylphenylsulfanyl)-benzamide;
exo-N-[(4S)-1-azabicyclo[2.2.1]hept-3-yl]-4-(3-carbamoylphenylsulfanyl)-benzamide;
exo-N-[(4S)-1-azabicyclo[2.2.1]hept-3-yl]-4-(2-carbamoylphenylsulfanyl)-benzamide;
exo-N-[(4S)-1-azabicyclo[2.2.1]hept-3-yl]-4-(4-hydroxyphenylsulfanyl)-benzamide;
exo-N-[(4S)-1-azabicyclo[2.2.1]hept-3-yl]-4-(3-hydroxyphenylsulfanyl)-benzamide;

exo-N-[(4S)-1-azabicyclo[2.2.1]hept-3-yl]-4-(2-hydroxyphenylsulfanyl)-benzamide;
exo-N-[(4S)-1-azabicyclo[2.2.1]hept-3-yl]-4-(4-acetamidophenylsulfanyl)-benzamide;
exo-N-[(4S)-1-azabicyclo[2.2.1]hept-3-yl]-4-(3-acetamidophenylsulfanyl)-benzamide;
exo-N-[(4S)-1-azabicyclo[2.2.1]hept-3-yl]-4-(2-acetamidophenylsulfanyl)-benzamide;
exo-N-[(4S)-1-azabicyclo[2.2.1]hept-3-yl]-4-(thiophen-2-ylsulfanyl)-benzamide;
exo-N-[(4S)-1-azabicyclo[2.2.1]hept-3-yl]-4-(5-methylthiophen-2-ylsulfanyl)-benzamide;
exo-N-[(4S)-1-azabicyclo[2.2.1]hept-3-yl]-4-(5-chlorothiophen-2-ylsulfanyl)-benzamide;
exo-N-[(4S)-1-azabicyclo[2.2.1]hept-3-yl]-4-(5-trifluoromethylthiophen-2-ylsulfanyl)-benzamide;
exo-N-[(4S)-1-azabicyclo[2.2.1]hept-3-yl]-4-(furan-2-ylsulfanyl)-benzamide;
exo-N-[(4S)-1-azabicyclo[2.2.1]hept-3-yl]-4-(5-methylfuran-2-ylsulfanyl)-benzamide;
exo-N-[(4S)-1-azabicyclo[2.2.1]hept-3-yl]-4-(5-chlorofuran-2-ylsulfanyl)-benzamide;
exo-N-[(4S)-1-azabicyclo[2.2.1]hept-3-yl]-4-(oxazol-2-ylsulfanyl)-benzamide;
exo-N-[(4S)-1-azabicyclo[2.2.1]hept-3-yl]-4-(5-chlorooxazol-2-ylsulfanyl))-benzamide;
exo-N-[(4S)-1-azabicyclo[2.2.1]hept-3-yl]-4-(5-methoxyoxazol-2-ylsulfanyl)-benzamide;
exo-N-[(4S)-1-azabicyclo[2.2.1]hept-3-yl]-4-(5-trifluoromethyloxazol-2-ylsulfanyl)-benzamide;
exo-N-[(4S)-1-azabicyclo[2.2.1]hept-3-yl]-4-(oxazol-2-ylsulfanyl)-benzamide;
exo-N-[(4S)-1-azabicyclo[2.2.1]hept-3-yl]-4-(oxazol-5-ylsulfanyl)-benzamide;
exo-N-[(4S)-1-azabicyclo[2.2.1]hept-3-yl]-4-(thiazol-2-ylsulfanyl)-benzamide;
exo-N-[(4S)-1-azabicyclo[2.2.1]hept-3-yl]-4-(thiazol-5-ylsulfanyl)-benzamide;
exo-N-[(4S)-1-azabicyclo[2.2.1]hept-3-yl]-4-([1,3,4]oxadiazol-2-ylsulfanyl)-benzamide;
exo-N-[(4S)-1-azabicyclo[2.2.1]hept-3-yl]-4-([1,3,4]thiadiazol-2-ylsulfanyl)-benzamide;
exo-N-[(4S)-1-azabicyclo[2.2.1]hept-3-yl]-4-(5-trifluoromethylpyrrol-2-yloxy)-benzamide;
exo-N-[(4S)-1-azabicyclo[2.2.1]hept-3-yl]-4-(3H-imidazol-4-yloxy)-benzamide;
exo-N-[(4S)-1-azabicyclo[2.2.1]hept-3-yl]-4-(isoxazol-2-yloxy)-benzamide;
exo-N-[(4S)-1-azabicyclo[2.2.1]hept-3-yl]-4-(isothiazol-2-yloxy)-benzamide;
exo-N-[(4S)-1-azabicyclo[2.2.1]hept-3-yl]-4-(pyrrol-2-ylsulfanyl)-benzamide;
exo-N-[(4S)-1-azabicyclo[2.2.1]hept-3-yl]-4-(3H-imidazol-4-ylsulfanyl)-benzamide;
exo-N-[(4S)-1-azabicyclo[2.2.1]hept-3-yl]-4-(isoxazol-2-ylsulfanyl)-benzamide;
exo-N-[(4S)-1-azabicyclo[2.2.1]hept-3-yl]-4-(isothiazol-2-ylsulfanyl)-benzamide;
exo-N-[(4S)-1-azabicyclo[2.2.1]hept-3-yl]-4-(6-methylpyridin-3-yloxy)-benzamide;
exo-N-[(4S)-1-azabicyclo[2.2.1]hept-3-yl]-4-(6-chloropyridin-3-yloxy)-benzamide;
exo-N-[(4S)-1-azabicyclo[2.2.1]hept-3-yl]-4-(6-methoxypyridin-3-yloxy)-benzamide;
exo-N-[(4S)-1-azabicyclo[2.2.1]hept-3-yl]-4-(6-trifluoromethylpyridin-3-yloxy)-benzamide;
exo-N-[(4S)-1-azabicyclo[2.2.1]hept-3-yl]-4-(2-chloropyridin-4-yloxy)-benzamide;
exo-N-[(4S)-1-azabicyclo[2.2.1]hept-3-yl]-4-(5-chloropyridin-2-yloxy)-benzamide;
exo-N-[(4S)-1-azabicyclo[2.2.1]hept-3-yl]-4-(4-chloropyridin-2-yloxy)-benzamide;
exo-N-[(4S)-1-azabicyclo[2.2.1]hept-3-yl]-4-(6-chloropyridin-2-yloxy)-benzamide;
exo-N-[(4S)-1-azabicyclo[2.2.1]hept-3-yl]-4-(5-chloropyridin-3-yloxy)-benzamide;
exo-N-[(4S)-1-azabicyclo[2.2.1]hept-3-yl]-4-(2-chloropyridin-3-yloxy)-benzamide;
exo-N-[(4S)-1-azabicyclo[2.2.1]hept-3-yl]-4-(4-chloropyridin-3-yloxy)-benzamide;
exo-N-[(4S)-1-azabicyclo[2.2.1]hept-3-yl]-4-(3-chloropyridin-4-yloxy)-benzamide;
exo-N-[(4S)-1-azabicyclo[2.2.1]hept-3-yl]-4-(3-chloropyridin-2-yloxy)-benzamide;
exo-N-[(4S)-1-azabicyclo[2.2.1]hept-3-yl]-4-(6-chloropyridin-3-ylsulfanyl)-benzamide;
N-[(3R,5R)-1-azabicyclo[3.2.1]oct-3-yl]-4-(4-hydroxyphenoxy)benzamide;
N-[(3R,5R)-1-azabicyclo[3.2.1]oct-3-yl]-4-(4-acetamidophenoxy)benzamide;
N-[(3R,5R)-1-azabicyclo[3.2.1]oct-3-yl]-4-phenoxybenzamide;
N-[(3R,5R)-1-azabicyclo[3.2.1]oct-3-yl]-4-benzylbenzamide;
N-[(3R,5R)-1-azabicyclo[3.2.1]oct-3-yl]-4-(phenylsulfanyl)-benzamide;
N-[(3R,5R)-1-azabicyclo[3.2.1]oct-3-yl]-3-phenoxybenzamide;
N-[(3R,5R)-1-azabicyclo[3.2.1]oct-3-yl]-4-(4-fluorophenoxy)benzamide;
N-[(3R,5R)-1-azabicyclo[3.2.1]oct-3-yl]-4-(2-fluorophenoxy)-benzamide;
N-[(3R,5R)-1-azabicyclo[3.2.1]oct-3-yl]-4-(3-fluorophenoxy)-benzamide;
N-[(3R,5R)-1-azabicyclo[3.2.1]oct-3-yl]-4-(2-chlorophenoxy)-benzamide;
N-[(3R,5R)-1-azabicyclo[3.2.1]oct-3-yl]-4-(3-chlorophenoxy)-benzamide;
N-[(3R,5R)-1-azabicyclo[3.2.1]oct-3-yl]-4-(4-chlorophenoxy)-benzamide;
N-[(3R,5R)-1-azabicyclo[3.2.1]oct-3-yl]-4-(2-methoxyphenoxy)-benzamide;
N-[(3R,5R)-1-azabicyclo[3.2.1]oct-3-yl]-4-(3-methoxyphenoxy)-benzamide;
N-[(3R,5R)-1-azabicyclo[3.2.1]oct-3-yl]-4-(4-methoxyphenoxy)-benzamide;
N-[(3R,5R)-1-azabicyclo[3.2.1]oct-3-yl]-4-(3-chlorophenylsulfanyl)benzamide;
N-[(3R,5R)-1-azabicyclo[3.2.1]oct-3-yl]-4-(4-chlorophenyl-sulfanyl)benzamide;
N-[(3R,5R)-1-azabicyclo[3.2.1]oct-3-yl]-4-(2-chlorophenyl-sulfanyl)benzamide;
N-[(3R,5R)-1-azabicyclo[3.2.1]oct-3-yl]-4-(4-methoxyphenyl-sulfanyl)benzamide;
N-[(3R,5R)-1-azabicyclo[3.2.1]oct-3-yl]-4-(3-methoxyphenyl-sulfanyl)benzamide;
N-[(3R,5R)-1-azabicyclo[3.2.1]oct-3-yl]-4-(2-methoxyphenyl-sulfanyl)benzamide;
N-[(3R,5R)-1-azabicyclo[3.2.1]oct-3-yl]-4-(4-aminophenoxy)-benzamide;
N-[(3R,5R)-1-azabicyclo[3.2.1]oct-3-yl]-4-(3-aminophenoxy)-benzamide;
N-[(3R,5R)-1-azabicyclo[3.2.1]oct-3-yl]-4-(2-aminophenoxy)-benzamide;
N-[(3R,5R)-1-azabicyclo[3.2.1]oct-3-yl]-4-(4-acetylphenoxy)-benzamide;

N-[(3R,5R)-1-azabicyclo[3.2.1]oct-3-yl]-4-(3-acetylphenoxy)-benzamide;
N-[(3R,5R)-1-azabicyclo[3.2.1]oct-3-yl]-4-(2-acetylphenoxy)-benzamide;
N-[(3R,5R)-1-azabicyclo[3.2.1]oct-3-yl]-4-(4-carbamoylphenoxy)-benzamide;
N-[(3R,5R)-1-azabicyclo[3.2.1]oct-3-yl]-4-(3-carbamoylphenoxy)-benzamide;
N-[(3R,5R)-1-azabicyclo[3.2.1]oct-3-yl]-4-(2-carbamoylphenoxy)-benzamide;
N-[(3R,5R)-1-azabicyclo[3.2.1]oct-3-yl]-4-(4-cyanophenoxy)-benzamide;
N-[(3R,5R)-1-azabicyclo[3.2.1]oct-3-yl]-4-(3-cyanophenoxy)-benzamide;
N-[(3R,5R)-1-azabicyclo[3.2.1]oct-3-yl]-4-(2-cyanophenoxy)-benzamide;
N-[(3R,5R)-1-azabicyclo[3.2.1]oct-3-yl]-4-(thiophen-2-yloxy)-benzamide;
N-[(3R,5R)-1-azabicyclo[3.2.1]oct-3-yl]-4-(5-methylthiophen-2-yloxy)-benzamide;
N-[(3R,5R)-1-azabicyclo[3.2.1]oct-3-yl]-4-(5-chlorothiophen-2-yloxy)-benzamide;
N-[(3R,5R)-1-azabicyclo[3.2.1]oct-3-yl]-4-(5-methoxythiophen-2-yloxy)-benzamide;
N-[(3R,5R)-1-azabicyclo[3.2.1]oct-3-yl]-4-(5-trifluoromethylthiophen-2-yloxy)-benzamide;
N-[(3R,5R)-1-azabicyclo[3.2.1]oct-3-yl]-4-(4-methylthiophen-2-yloxy)-benzamide;
N-[(3R,5R)-1-azabicyclo[3.2.1]oct-3-yl]-4-(4-chlorothiophen-2-yloxy)-benzamide;
N-[(3R,5R)-1-azabicyclo[3.2.1]oct-3-yl]-4-(4-methoxythiophen-2-yloxy)-benzamide;
N-[(3R,5R)-1-azabicyclo[3.2.1]oct-3-yl]-4-(4-trifluoromethylthiophen-2-yloxy)-benzamide;
N-[(3R,5R)-1-azabicyclo[3.2.1]oct-3-yl]-4-(furan-2-yloxy)-benzamide;
N-[(3R,5R)-1-azabicyclo[3.2.1]oct-3-yl]-4-(5-methylfuran-2-yloxy)-benzamide;
N-[(3R,5R)-1-azabicyclo[3.2.1]oct-3-yl]-4-(5-chlorofuran-2-yloxy)-benzamide;
N-[(3R,5R)-1-azabicyclo[3.2.1]oct-3-yl]-4-(5-methoxyfuran-2-yloxy)-benzamide;
N-[(3R,5R)-1-azabicyclo[3.2.1]oct-3-yl]-4-(5-trifluoromethylfuran-2-yloxy)-benzamide;
N-[(3R,5R)-1-azabicyclo[3.2.1]oct-3-yl]-4-(4-methylfuran-2-yloxy)-benzamide;
N-[(3R,5R)-1-azabicyclo[3.2.1]oct-3-yl]-4-(4-chlorofuran-2-yloxy)-benzamide;
N-[(3R,5R)-1-azabicyclo[3.2.1]oct-3-yl]-4-(4-methoxyfuran-2-yloxy)-benzamide;
N-[(3R,5R)-1-azabicyclo[3.2.1]oct-3-yl]-4-(4-trifluoromethylfuran-2-yloxy)-benzamide;
N-[(3R,5R)-1-azabicyclo[3.2.1]oct-3-yl]-4-(oxazol-2-yloxy)-benzamide;
N-[(3R,5R)-1-azabicyclo[3.2.1]oct-3-yl]-4-(oxazol-S-yloxy)-benzamide;
N-[(3R,5R)-1-azabicyclo[3.2.1]oct-3-yl]-4-(thiazol-2-yloxy)-benzamide;
N-[(3R,5R)-1-azabicyclo[3.2.1]oct-3-yl]-4-(thiazol-5-yloxy)-benzamide;
N-[(3R,5R)-1-azabicyclo[3.2.1]oct-3-yl]-4-([1,3,4]oxadiazol-2-yloxy)-benzamide;
N-[(3R,5R)-1-azabicyclo[3.2.1]oct-3-yl]-4-([1,3,4]thiadiazol-2-yloxy)-benzamide;
N-[(3R,5R)-1-azabicyclo[3.2.1]oct-3-yl]-4-(4-aminophenylsulfanyl)-benzamide;
N-[(3R,5R)-1-azabicyclo[3.2.1]oct-3-yl]-4-(3-aminophenylsulfanyl)-benzamide;
N-[(3R,5R)-1-azabicyclo[3.2.1]oct-3-yl]-4-(2-aminophenylsulfanyl)-benzamide;
N-[(3R,5R)-1-azabicyclo[3.2.1]oct-3-yl]-4-(4-acetylphenylsulfanyl)-benzamide;
N-[(3R,5R)-1-azabicyclo[3.2.1]oct-3-yl]-4-(3-acetylphenylsulfanyl)-benzamide;
N-[(3R,5R)-1-azabicyclo[3.2.1]oct-3-yl]-4-(2-acetylphenylsulfanyl)-benzamide;
N-[(3R,5R)-1-azabicyclo[3.2.1]oct-3-yl]-4-(4-carbamoylphenylsulfanyl)-benzamide;
N-[(3R,5R)-1-azabicyclo[3.2.1]oct-3-yl]-4-(3-carbamoylphenylsulfanyl)-benzamide;
N-[(3R,5R)-1-azabicyclo[3.2.1]oct-3-yl]-4-(2-carbamoylphenylsulfanyl)-benzamide;
N-[(3R,5R)-1-azabicyclo[3.2.1]oct-3-yl]-4-(4-hydroxyphenylsulfanyl)-benzamide;
N-[(3R,5R)-1-azabicyclo[3.2.1]oct-3-yl]-4-(3-hydroxyphenylsulfanyl)-benzamide;
N-[(3R,5R)-1-azabicyclo[3.2.1]oct-3-yl]-4-(2-hydroxyphenylsulfanyl)-benzamide;
N-[(3R,5R)-1-azabicyclo[3.2.1]oct-3-yl]-4-(4-acetamidophenylsulfanyl)-benzamide;
N-[(3R,5R)-1-azabicyclo[3.2.1]oct-3-yl]-4-(3-acetamidophenylsulfanyl)-benzamide;
N-[(3R,5R)-1-azabicyclo[3.2.1]oct-3-yl]-4-(2-acetamidophenylsulfanyl)-benzamide;
N-[(3R,5R)-1-azabicyclo[3.2.1]oct-3-yl]-4-(thiophen-2-ylsulfanyl)-benzamide;
N-[(3R,5R)-1-azabicyclo[3.2.1]oct-3-yl]-4-(5-methylthiophen-2-ylsulfanyl)-benzamide;
N-[(3R,5R)-1-azabicyclo[3.2.1]oct-3-yl]-4-(5-chlorothiophen-2-ylsulfanyl)-benzamide;
N-[(3R,5R)-1-azabicyclo[3.2.1]oct-3-yl]-4-(5-trifluoromethylthiophen-2-ylsulfanyl)-benzamide;
N-[(3R,5R)-1-azabicyclo[3.2.1]oct-3-yl]-4-(furan-2-ylsulfanyl)-benzamide;
N-[(3R,5R)-1-azabicyclo[3.2.1]oct-3-yl]-4-(5-methylfuran-2-ylsulfanyl)-benzamide;
N-[(3R,5R)-1-azabicyclo[3.2.1]oct-3-yl]-4-(5-chlorofuran-2-ylsulfanyl)-benzamide;
N-[(3R,5R)-1-azabicyclo[3.2.1]oct-3-yl]-4-(oxazol-2-ylsulfanyl)-benzamide;
N-[(3R,5R)-1-azabicyclo[3.2.1 1]oct-3-yl]-4-(5-chlorooxazol-2-ylsulfanyl)-benzamide;
N-[(3R,5R)-1-azabicyclo[3.2.1]oct-3-yl]-4-(5-methoxyoxazol-2-ylsulfanyl)-benzamide;
N-[(3R,5R)-1-azabicyclo[3.2.1]oct-3-yl]-4-(5-trifluoromethyloxazol-2-ylsulfanyl)-benzamide;
N-[(3R,5R)-1-azabicyclo[3.2.1]oct-3-yl]-4-(oxazol-2-ylsulfanyl)-benzamide;
N-[(3R,5R)-1-azabicyclo[3.2.1]oct-3-yl]-4-(oxazol-5-ylsulfanyl)-benzamide;
N-[(3R,5R)-1-azabicyclo[3.2.1]oct-3-yl]-4-(thiazol-2-ylsulfanyl)-benzamide;
N-[(3R,5R)-1-azabicyclo[3.2.1]oct-3-yl]-4-(thiazol-5-ylsulfanyl)-benzamide;
N-[(3R,5R)-1-azabicyclo[3.2.1]oct-3-yl]-4-([1,3,4]oxadiazol-2-ylsulfanyl)-benzamide; N-[(3R,5R)-1-azabicyclo[3.2.1]oct-3-yl]-4-([1,3,4]thiadiazol-2-ylsulfanyl)-benzamide;
N-[(3R,5R)-1-azabicyclo[3.2.1]oct-3-yl]-4-(5-trifluoromethylpyrrol-2-yloxy)-benzamide;
N-[(3R,5R)-1-azabicyclo[3.2.1]oct-3-yl]-4-(3H-imidazol-4-yloxy)-benzamide;
N-[(3R,5R)-1-azabicyclo[3.2.1]oct-3-yl]-4-(isoxazol-2-yloxy)-benzamide;
N-[(3R,5R)-1-azabicyclo[3.2.1]oct-3-yl]-4-(isothiazol-2-yloxy)-benzamide;

N-[(3R,5R)-1-azabicyclo[3.2.1]oct-3-yl]-4-(pyrrol-2-ylsulfanyl)-benzamide;
N-[(3R,5R)-1-azabicyclo[3.2.1]oct-3-yl]-4-(3H-imidazol-4-ylsulfanyl)-benzamide;
N-[(3R,5R)-1-azabicyclo[3.2.1]oct-3-yl]-4-(isoxazol-2-ylsulfanyl)-benzamide;
N-[(3R,5R)-1-azabicyclo[3.2.1]oct-3-yl]-4-(isothiazol-2-ylsulfanyl)-benzamide;
N-[(3R,5R)-1-azabicyclo[3.2.1]oct-3-yl]-4-(6-methylpyridin-3-yloxy)-benzamide;
N-[(3R,5R)-1-azabicyclo[3.2.1]oct-3-yl]-4-(6-chloropyridin-3-yloxy)-benzamide;
N-[(3R,5R)-1-azabicyclo[3.2.1]oct-3-yl]-4-(6-methoxypyridin-3-yloxy)-benzamide;
N-[(3R,5R)-1-azabicyclo[3.2.1]oct-3-yl]-4-(6-trifluoromethylpyridin-3-yloxy)-benzamide;
N-[(3R,5R)-1-azabicyclo[3.2.1]oct-3-yl]-4-(2-chloropyridin-4-yloxy)-benzamide;
N-[(3R,5R)-1-azabicyclo[3.2.1]oct-3-yl]-4-(5-chloropyridin-2-yloxy)-benzamide;
N-[(3R,5R)-1-azabicyclo[3.2.1]oct-3-yl]-4-(4-chloropyridin-2-yloxy)-benzamide;
N-[(3R,5R)-1-azabicyclo[3.2.1]oct-3-yl]-4-(6-chloropyridin-2-yloxy)-benzamide;
N-[(3R,5R)-1-azabicyclo[3.2.1]oct-3-yl]-4-(5-chloropyridin-3-yloxy)-benzamide;
N-[(3R,5R)-1-azabicyclo[3.2.1]oct-3-yl]-4-(2-chloropyridin-3-yloxy)-benzamide;
N-[(3R,5R)-1-azabicyclo[3.2.1]oct-3-yl]-4-(4-chloropyridin-3-yloxy)-benzamide;
N-[(3R,5R)-1-azabicyclo[3.2.1]oct-3-yl]-4-(3-chloropyridin-4-yloxy)-benzamide;
N-[(3R,5R)-1-azabicyclo[3.2.1]oct-3-yl]-4-(3-chloropyridin-2-yloxy)-benzamide;
N-[(3R,5R)-1-azabicyclo[3.2.1]oct-3-yl]-4-(6-chloropyridin-3-ylsulfanyl)-benzamide;
N-[1-azabicyclo[3.2.2]nonan-3-yl]-4-(4-hydroxyphenoxy)benzamide;
N-[1-azabicyclo[3.2.2]nonan-3-yl]-4-(4-acetamidophenoxy)benzamide;
N-[1-azabicyclo[3.2.2]nonan-3-yl]-4-phenoxybenzamide;
N-[1-azabicyclo[3.2.2]nonan-3-yl]-4-benzylbenzamide;
N-[1-azabicyclo[3.2.2]nonan-3-yl]-4-(phenylsulfanyl)-benzamide;
N-[1-azabicyclo[3.2.2]nonan-3-yl]-3-phenoxybenzamide;
N-[1-azabicyclo[3.2.2]nonan-3-yl]-4-(4-fluorophenoxy)benzamide;
N-[1-azabicyclo[3.2.2]nonan-3-yl]-4-(2-fluorophenoxy)benzamide;
N-[1-azabicyclo[3.2.2]nonan-3-yl]-4-(3-fluorophenoxy)-benzamide;
N-[1-azabicyclo[3.2.2]nonan-3-yl]-4-(2-chlorophenoxy)-benzamide;
N-[1-azabicyclo[3.2.2]nonan-3-yl]-4-(3-chlorophenoxy)-benzamide;
N-[1-azabicyclo[3.2.2]nonan-3-yl]-4-(4-chlorophenoxy)-benzamide;
N-[1-azabicyclo[3.2.2]nonan-3-yl]-4-(2-methoxyphenoxy)-benzamide;
N-[1-azabicyclo[3.2.2]nonan-3-yl]-4-(3-methoxyphenoxy)-benzamide;
N-[1-azabicyclo[3.2.2]nonan-3-yl]-4-(4-methoxyphenoxy)-benzamide;
N-[1-azabicyclo[3.2.2]nonan-3-yl]-4-(3-chlorophenylsulfanyl)benzamide;
N-[1-azabicyclo[3.2.2]nonan-3-yl]-4-(4-chlorophenylsulfanyl)benzamide;
N-[1-azabicyclo[3.2.2]nonan-3-yl]-4-(2-chlorophenylsulfanyl)benzamide;
N-[1-azabicyclo[3.2.2]nonan-3-yl]-4-(4-methoxyphenylsulfanyl)benzamide;
N-[1-azabicyclo[3.2.2]nonan-3-yl]-4-(3-methoxyphenylsulfanyl)benzamide;
N-[1-azabicyclo[3.2.2]nonan-3-yl]-4-(2-methoxyphenylsulfanyl)benzamide;
N-[1-azabicyclo[3.2.2]nonan-3-yl]-4-(4-aminophenoxy)-benzamide;
N-[1-azabicyclo[3.2.2]nonan-3-yl]-4-(3-aminophenoxy)-benzamide;
N-[1-azabicyclo[3.2.2]nonan-3-yl]-4-(2-aminophenoxy)-benzamide;
N-[1-azabicyclo[3.2.2]nonan-3-yl]-4-(4-acetylphenoxy)-benzamide;
N-[1-azabicyclo[3.2.2]nonan-3-yl]-4-(3-acetylphenoxy)-benzamide;
N-[1-azabicyclo[3.2.2]nonan-3-yl]-4-(2-acetylphenoxy)-benzamide;
N-[1-azabicyclo[3.2.2]nonan-3-yl]-4-(4-carbamoylphenoxy)-benzamide;
N-[1-azabicyclo[3.2.2]nonan-3-yl]-4-(3-carbamoylphenoxy)-benzamide;
N-[1-azabicyclo[3.2.2]nonan-3-yl]-4-(2-carbamoylphenoxy)-benzamide;
N-[1-azabicyclo[3.2.2]nonan-3-yl]-4-(4-cyanophenoxy)-benzamide;
N-[1-azabicyclo[3.2.2]nonan-3-yl]-4-(3-cyanophenoxy)-benzamide;
N-[1-azabicyclo[3.2.2]nonan-3-yl]-4-(2-cyanophenoxy)-benzamide;
N-[1-azabicyclo[3.2.2]nonan-3-yl]-4-(thiophen-2-yloxy)-benzamide;
N-[1-azabicyclo[3.2.2]nonan-3-yl]-4-(5-methylthiophen-2-yloxy)-benzamide;
N-[1-azabicyclo[3.2.2]nonan-3-yl]-4-(5-chlorothiophen-2-yloxy)-benzamide;
N-[1-azabicyclo[3.2.2]nonan-3-yl]-4-(5-methoxythiophen-2-yloxy)-benzamide;
N-[-azabicyclo[3.2.2]nonan-3-yl]-4-(5-trifluoromethyl-thiophen-2-yloxy)-benzamide;
N-[1-azabicyclo[3.2.2]nonan-3-yl]-4-(4-methylthiophen-2-yloxy)-benzamide;
-[1-azabicyclo[3.2.2]nonan-3-yl]-4-(4-chlorothiophen-2-yloxy)-benzamide;
N-[1-azabicyclo[3.2.2]nonan-3-yl]-4-(4-methoxythiophen-2-yloxy)-benzamide;
N-[1-azabicyclo[3.2.2]nonan-3-yl]-4-(4-trifluoromethylthiophen-2-yloxy)-benzamide;
N-[1-azabicyclo[3.2.2]nonan-3-yl]-4-(furan-2-yloxy)-benzamide;
N-[1-azabicyclo[3.2.2]nonan-3-yl]-4-(5-methylfuran-2-yloxy)-benzamide;
N-[1-azabicyclo[3.2.2]nonan-3-yl]-4-(5-chlorofuran-2-yloxy)-benzamide;
N-[1-azabicyclo[3.2.2]nonan-3-yl]-4-(5-methoxyfuran-2-yloxy)-benzamide;
N-[1-azabicyclo[3.2.2]nonan-3-yl]-4-(5-trifluoromethylfuran-2-yloxy)-benzamide;
N-[1-azabicyclo[3.2.2]nonan-3-yl]-4-(4-methylfuran-2-yloxy)-benzamide;
N-[1-azabicyclo[3.2.2]nonan-3-yl]-4-(4-chlorofuran-2-yloxy)-benzamide;
N-[1-azabicyclo[3.2.2]nonan-3-yl]-4-(4-methoxyfuran-2-yloxy)-benzamide;
N-[1-azabicyclo[3.2.2]nonan-3-yl]-4-(4-trifluoromethylfuran-2-yloxy)-benzamide;

N-[1-azabicyclo[3.2.2]nonan-3-yl]-4-(oxazol-2-yloxy)-benzamide;
N-[1-azabicyclo[3.2.2]nonan-3-yl]-4-(oxazol-5-yloxy)-benzamide;
N-[1-azabicyclo[3.2.2]nonan-3-yl]-4-(thiazol-2-yloxy)-benzamide;
N-[1-azabicyclo[3.2.2]nonan-3-yl]-4-(thiazol-5-yloxy)-benzamide;
N-[1-azabicyclo[3.2.2]nonan-3-yl]-4-([1,3,4]oxadiazol-2-yloxy)-benzamide;
N-[1-azabicyclo[3.2.2]nonan-3-yl]-4-([1,3,4]thiadiazol-2-yloxy)-benzamide;
N-[1-azabicyclo[3.2.2]nonan-3-yl]-4-(4-aminophenyl-sulfanyl)-benzamide;
N-[1-azabicyclo[3.2.2]nonan-3-yl]-4-(3-aminophenyl-sulfanyl)-benzamide;
N-[1-azabicyclo[3.2.2]nonan-3-yl]-4-(2-aminophenyl-sulfanyl)-benzamide;
N-[1-azabicyclo[3.2.2]nonan-3-yl]-4-(4-acetylphenyl-sulfanyl)-benzamide;
N-[1-azabicyclo[3.2.2]nonan-3-yl]-4-(3-acetylphenyl-sulfanyl)-benzamide;
N-[1-azabicyclo[3.2.2]nonan-3-yl]-4-(2-acetylphenyl-sulfanyl)-benzamide;
N-[1-azabicyclo[3.2.2]nonan-3-yl]-4-(4-carbamoylphenyl-sulfanyl)-benzamide;
N-[1-azabicyclo[3.2.2]nonan-3-yl]-4-(3-carbamoylphenyl-sulfanyl)-benzamide;
N-[1-azabicyclo[3.2.2]nonan-3-yl]-4-(2-carbamoylphenyl-sulfanyl)-benzamide;
N-[1-azabicyclo[3.2.2]nonan-3-yl]-4-(4-hydroxyphenyl-sulfanyl)-benzamide;
N-[1-azabicyclo[3.2.2]nonan-3-yl]-4-(3-hydroxyphenyl-sulfanyl)-benzamide;
N-[1-azabicyclo[3.2.2]nonan-3-yl]-4-(2-hydroxyphenyl-sulfanyl)-benzamide;
N-[1-azabicyclo[3.2.2]nonan-3-yl]-4-(4-acetamidophenyl-sulfanyl)-benzamide;
N-[1-azabicyclo[3.2.2]nonan-3-yl]-4-(3-acetamidophenyl-sulfanyl)-benzamide;
N-[1-azabicyclo[3.2.2]nonan-3-yl]-4-(2-acetamidophenyl-sulfanyl)-benzamide;
N-[1-azabicyclo[3.2.2]nonan-3-yl]-4-(thiophen-2-ylsulfanyl)-benzamide;
N-[1-azabicyclo[3.2.2]nonan-3-yl]-4-(5-methylthiophen-2-ylsulfanyl)-benzamide;
N-[1-azabicyclo[3.2.2]nonan-3-yl]-4-(5-chlorothiophen-2-ylsulfanyl)-benzamide;
N-[1-azabicyclo[3.2.2]nonan-3-yl]-4-(5-trifluoromethyl-thiophen-2-ylsulfanyl)-benzamide;
N-[1-azabicyclo[3.2.2]nonan-3-yl]-4-(furan-2-ylsulfanyl)-benzamide;
N-[1-azabicyclo[3.2.2]nonan-3-yl]-4-(5-methylfuran-2-ylsulfanyl)-benzamide;
N-[1-azabicyclo[3.2.2]nonan-3-yl]-4-(5-chlorofuran-2-ylsulfanyl)-benzamide;
N-[1-azabicyclo[3.2.2]nonan-3-yl]-4-(oxazol-2-ylsulfanyl)-benzamide;
N-[1-azabicyclo[3.2.2]nonan-3-yl]-4-(5-chlorooxazol-2-ylsulfanyl)-benzamide;
N-[1-azabicyclo[3.2.2]nonan-3-yl]-4-(5-methoxyoxazol-2-ylsulfanyl)-benzamide;
N-[1-azabicyclo[3.2.2]nonan-3-yl]-4-(5-trifluoromethyl-oxazol-2-ylsulfanyl)-benzamide;
N-[1-azabicyclo[3.2.2]nonan-3-yl]-4-(oxazol-2-ylsulfanyl)-benzamide;
N-[1-azabicyclo[3.2.2]nonan-3-yl]-4-(oxazol-5-ylsulfanyl)-benzamide;
N-[1-azabicyclo[3.2.2]nonan-3-yl]-4-(thiazol-2-ylsulfanyl)-benzamide;
N-[1-azabicyclo[3.2.2]nonan-3-yl]-4-(thiazol-5-ylsulfanyl)-benzamide;
N-[1-azabicyclo[3.2.2]nonan-3-yl]-4-([1,3,4]oxadiazol-2-ylsulfanyl)-benzamide;
N-[1-azabicyclo[3.2.2]nonan-3-yl]-4-([1,3,4]thiadiazol-2-ylsulfanyl)-benzamide;
N-[1-azabicyclo[3.2.2]nonan-3-yl]-4-(5-trifluoro-methylpyrrol-2-yloxy)-benzamide;
N-[1-azabicyclo[3.2.2]nonan-3-yl]-4-(3H-imidazol-4-yloxy)-benzamide;
N-[1-azabicyclo[3.2.2]nonan-3-yl]-4-(isoxazol-2-yloxy)-benzamide;
N-[1-azabicyclo[3.2.2]nonan-3-yl]-4-(isothiazol-2-yloxy)-benzamide;
N-[1-azabicyclo[3.2.2]nonan-3-yl]-4-(pyrrol-2-ylsulfanyl)-benzamide;
N-[1-azabicyclo[3.2.2]nonan-3-yl]-4-(3H-imidazol-4-ylsulfanyl)-benzamide;
N-[1-azabicyclo[3.2.2]nonan-3-yl]-4-(isoxazol-2-ylsulfanyl)-benzamide;
N-[1-azabicyclo[3.2.2]nonan-3-yl]-4-(isothiazol-2-ylsulfanyl)-benzamide;
N-[1-azabicyclo[3.2.2]nonan-3-yl]-4-(6-methylpyridin-3-yloxy)-benzamide;
N-[1-azabicyclo[3.2.2]nonan-3-yl]-4-(6-chloropyridin-3-yloxy)-benzamide;
N-[1-azabicyclo[3.2.2]nonan-3-yl]-4-(6-methoxypyridin-3-yloxy)-benzamide;
N-[1-azabicyclo[3.2.2]nonan-3-yl]-4-(6-trifluoro-methylpyridin-3-yloxy)-benzamide;
N-[1-azabicyclo[3.2.2]nonan-3-yl]-4-(2-chloropyridin-4-yloxy)-benzamide;
N-[1-azabicyclo[3.2.2]nonan-3-yl]-4-(5-chloropyridin-2-yloxy)-benzamide;
N-[1-azabicyclo[3.2.2]nonan-3-yl]-4-(4-chloropyridin-2-yloxy)-benzamide;
N-[1-azabicyclo[3.2.2]nonan-3-yl]-4-(6-chloropyridin-2-yloxy)-benzamide;
N-[1-azabicyclo[3.2.2]nonan-3-yl]-4-(5-chloropyridin-3-yloxy)-benzamide;
N-[1-azabicyclo[3.2.2]nonan-3-yl]-4-(2-chloropyridin-3-yloxy)-benzamide;
N-[1-azabicyclo[3.2.2]nonan-3-yl]-4-(4-chloropyridin-3-yloxy)-benzamide;
N-[1-azabicyclo[3.2.2]nonan-3-yl]-4-(3-chloropyridin-4-yloxy)-benzamide;
N-[1-azabicyclo[3.2.2]nonan-3-yl]-4-(3-chloropyridin-2-yloxy)-benzamide; or
N-[1-azabicyclo[3.2.2]nonan-3-yl]-4-(6-chloropyridin-3-ylsulfanyl)-benzamide.

The present invention also includes, by representation but not limitation, any one or more or combination of the following compounds and pharmaceutically acceptable salts thereof, both of which can be made by one of ordinary skill in the art using the procedures provided making non-critical changes:
N-[2-azabicyclo[2.2.1]hept-5-yl]-4-(4-hydroxyphenoxy) benzamide;
N-[2-azabicyclo[2.2.1]hept-5-yl]-4-(4-acetamidophenoxy) benzamide;
N-[2-azabicyclo[2.2.1]hept-5-yl]-4-phenoxybenzamide;
N-[2-azabicyclo[2.2.1]hept-5-yl]-4-benzylbenzamide;
N-[2-azabicyclo[2.2.1]hept-5-yl]-4-(phenylsulfanyl)-benzamide;
N-[2-azabicyclo[2.2.1]hept-5-yl]-3-phenoxybenzamide;

N-[2-azabicyclo[2.2.1]hept-5-yl]-4-(4-fluorophenoxy)benzamide;
N-[2-azabicyclo[2.2.1]hept-5-yl]-4-(2-fluorophenoxy)-benzamide;
N-[2-azabicyclo[2.2.1]hept-5-yl]-4-(3-fluorophenoxy)-benzamide;
N-[2-azabicyclo[2.2.1]hept-5-yl]-4-(2-chlorophenoxy)-benzamide;
N-[2-azabicyclo[2.2.1]hept-5-yl]-4-(3-chlorophenoxy)-benzamide;
N-[2-azabicyclo[2.2.1]hept-5-yl]-4-(4-chlorophenoxy)-benzamide;
N-[2-azabicyclo[2.2.1]hept-5-yl]-4-(2-methoxyphenoxy)-benzamide;
N-[2-azabicyclo[2.2.1]hept-5-yl]-4-(3-methoxyphenoxy)-benzamide;
N-[2-azabicyclo[2.2.1]hept-5-yl]-4-(4-methoxyphenoxy)-benzamide;
N-[2-azabicyclo[2.2.1]hept-5-yl]-4-(3-chlorophenylsulfanyl)benzamide;
N-[2-azabicyclo[2.2.1]hept-5-yl]-4-(4-chlorophenylsulfanyl)benzamide;
N-[2-azabicyclo[2.2.1]hept-5-yl]-4-(2-chlorophenylsulfanyl)benzamide;
N-[2-azabicyclo[2.2.1]hept-5-yl]-4-(4-methoxyphenylsulfanyl)benzamide;
N-[2-azabicyclo[2.2.1]hept-5-yl]-4-(3-methoxyphenylsulfanyl)benzamide;
N-[2-azabicyclo[2.2.1]hept-5-yl]-4-(2-methoxyphenylsulfanyl)benzamide;
N-[2-azabicyclo[2.2.1]hept-5-yl]-4-(4-aminophenoxy)-benzamide;
N-[2-azabicyclo[2.2.1]hept-5-yl]-4-(3-aminophenoxy)-benzamide;
N-[2-azabicyclo[2.2.1]hept-5-yl]-4-(2-aminophenoxy)-benzamide;
N-[2-azabicyclo[2.2.1]hept-5-yl]-4-(4-acetylphenoxy)-benzamide;
N-[2-azabicyclo[2.2.1]hept-5-yl]-4-(3-acetylphenoxy)-benzamide;
N-[2-azabicyclo[2.2.1]hept-5-yl]-4-(2-acetylphenoxy)-benzamide;
N-[2-azabicyclo[2.2.1]hept-5-yl]-4-(4-carbamoylphenoxy)-benzamide;
N-[2-azabicyclo[2.2.1]hept-5-yl]-4-(3-carbamoylphenoxy)-benzamide;
N-[2-azabicyclo[2.2.1]hept-5-yl]-4-(2-carbamoylphenoxy)-benzamide;
N-[2-azabicyclo[2.2.1]hept-5-yl]-4-(4-cyanophenoxy)-benzamide;
N-[2-azabicyclo[2.2.1]hept-5-yl]-4-(3-cyanophenoxy)-benzamide;
N-[2-azabicyclo[2.2.1]hept-5-yl]-4-(2-cyanophenoxy)-benzamide;
N-[2-azabicyclo[2.2.1]hept-5-yl]-4-(thiophen-2-yloxy)-benzamide;
N-[2-azabicyclo[2.2.1]hept-5-yl]-4-(5-methylthiophen-2-yloxy)-benzamide;
N-[2-azabicyclo[2.2.1]hept-5-yl]-4-(5-chlorothiophen-2-yloxy)-benzamide;
N-[2-azabicyclo[2.2.1]hept-5-yl]-4-(5-methoxythiophen-2-yloxy)-benzamide;
N-[2-azabicyclo[2.2.1]hept-5-yl]-4-(5-trifluoromethylthiophen-2-yloxy)-benzamide;
N-[2-azabicyclo[2.2.1]hept-5-yl]-4-(4-methylthiophen-2-yloxy)-benzamide;
N-[2-azabicyclo[2.2.1]hept-5-yl]-4-(4-chlorothiophen-2-yloxy)-benzamide;
N-[2-azabicyclo[2.2.1]hept-5-yl]-4-(4-methoxythiophen-2-yloxy)-benzamide;
N-[2-azabicyclo[2.2.1]hept-5-yl]-4-(4-trifluoromethylthiophen-2-yloxy)-benzamide;
N-[2-azabicyclo[2.2.1]hept-5-yl]-4-(furan-2-yloxy)-benzamide;
N-[2-azabicyclo[2.2.1]hept-5-yl]-4-(5-methylfuran-2-yloxy)-benzamide;
N-[2-azabicyclo[2.2.1]hept-5-yl]-4-(5-chlorofuran-2-yloxy)-benzamide;
N-[2-azabicyclo[2.2.1]hept-5-yl]-4-(5-methoxyfuran-2-yloxy)-benzamide;
N-[2-azabicyclo[2.2.1]hept-5-yl]-4-(5-trifluoromethylfuran-2-yloxy)-benzamide;
N-[2-azabicyclo[2.2.1]hept-5-yl]-4-(4-methylfuran-2-yloxy)-benzamide;
N-[2-azabicyclo[2.2.1]hept-5-yl]-4-(4-chlorofuran-2-yloxy)-benzamide;
N-[2-azabicyclo[2.2.1]hept-5-yl]-4-(4-methoxyfuran-2-yloxy)-benzamide;
N-[2-azabicyclo[2.2.1]hept-5-yl]-4-(4-trifluoromethylfuran-2-yloxy)-benzamide;
N-[2-azabicyclo[2.2.1]hept-5-yl]-4-(oxazol-2-yloxy)-benzamide;
N-[2-azabicyclo[2.2.1]hept-5-yl]-4-(oxazol-5-yloxy)-benzamide;
N-[2-azabicyclo[2.2.1]hept-5-yl]-4-(thiazol-2-yloxy)-benzamide;
N-[2-azabicyclo[2.2.1]hept-5-yl]-4-(thiazol-5-yloxy)-benzamide;
N-[2-azabicyclo[2.2.1]hept-5-yl]-4-([1,3,4]oxadiazol-2-yloxy)-benzamide;
N-[2-azabicyclo[2.2.1]hept-5-yl]-4-([1,3,4]thiadiazol-2-yloxy)-benzamide;
N-[2-azabicyclo[2.2.1]hept-5-yl]-4-(4-aminophenylsulfanyl)-benzamide;
N-[2-azabicyclo[2.2.1]hept-5-yl]-4-(3-aminophenylsulfanyl)-benzamide;
N-[2-azabicyclo[2.2.1]hept-5-yl]-4-(2-aminophenylsulfanyl)-benzamide;
N-[2-azabicyclo[2.2.1]hept-5-yl]-4-(4-acetylphenylsulfanyl)-benzamide;
N-[2-azabicyclo[2.2.1]hept-5-yl]-4-(3-acetylphenylsulfanyl)-benzamide;
N-[2-azabicyclo[2.2.1]hept-5-yl]-4-(2-acetylphenylsulfanyl)-benzamide;
N-[2-azabicyclo[2.2.1]hept-5-yl]-4-(4-carbamoylphenylsulfanyl)-benzamide;
N-[2-azabicyclo[2.2.1]hept-5-yl]-4-(3-carbamoylphenylsulfanyl)-benzamide;
N-[2-azabicyclo[2.2.1]hept-5-yl]-4-(2-carbamoylphenylsulfanyl)-benzamide;
N-[2-azabicyclo[2.2.1]hept-5-yl]-4-(4-hydroxyphenylsulfanyl)-benzamide;
N-[2-azabicyclo[2.2.1]hept-5-yl]-4-(3-hydroxyphenylsulfanyl)-benzamide;
N-[2-azabicyclo[2.2.1]hept-5-yl]-4-(2-hydroxyphenylsulfanyl)-benzamide;
N-[2-azabicyclo[2.2.1]hept-5-yl]-4-(4-acetamidophenylsulfanyl)-benzamide;
N-[2-azabicyclo[2.2.1]hept-5-yl]-4-(3-acetamidophenylsulfanyl)-benzamide;
N-[2-azabicyclo[2.2.1]hept-5-yl]-4-(2-acetamidophenylsulfanyl)-benzamide;
N-[2-azabicyclo[2.2.1]hept-5-yl]-4-(thiophen-2-ylsulfanyl)-benzamide;
N-[2-azabicyclo[2.2.1]hept-5-yl]-4-(5-methylthiophen-2-ylsulfanyl)-benzamide;

N-[2-azabicyclo[2.2.1]hept-5-yl]-4-(5-chlorothiophen-2-ylsulfanyl)-benzamide;
N-[2-azabicyclo[2.2.1]hept-5-yl]-4-(5-trifluoromethylthiophen-2-ylsulfanyl)-benzamide;
N-[2-azabicyclo[2.2.1]hept-5-yl]-4-(furan-2-ylsulfanyl)-benzamide;
N-[2-azabicyclo[2.2.1]hept-5-yl]-4-(5-methylfuran-2-ylsulfanyl)-benzamide;
N-[2-azabicyclo[2.2.1]hept-5-yl]-4-(5-chlorofuran-2-ylsulfanyl)-benzamide;
N-[2-azabicyclo[2.2.1]hept-5-yl]-4-(oxazol-2-ylsulfanyl)-benzamide;
N-[2-azabicyclo[2.2.1]hept-5-yl]-4-(5-chlorooxazol-2-ylsulfanyl)-benzamide;
N-[2-azabicyclo[2.2.1]hept-5-yl]-4-(5-methoxyoxazol-2-ylsulfanyl)-benzamide;
N-[2-azabicyclo[2.2.1]hept-5-yl]-4-(5-trifluoromethyl-oxazol-2-ylsulfanyl)-benzamide;
N-[2-azabicyclo[2.2.1]hept-5-yl]-4-(oxazol-2-ylsulfanyl)-benzamide;
N-[2-azabicyclo[2.2.1]hept-5-yl]-4-(oxazol-5-ylsulfanyl)-benzamide;
N-[2-azabicyclo[2.2.1]hept-5-yl]-4-(thiazol-2-ylsulfanyl)-benzamide;
N-[2-azabicyclo[2.2.1]hept-5-yl]-4-(thiazol-5-ylsulfanyl)-benzamide;
N-[2-azabicyclo[2.2.1]hept-5-yl]-4-([1,3,4]oxadiazol-2-ylsulfanyl)-benzamide;
N-[2-azabicyclo[2.2.1]hept-5-yl]-4-([1,3,4]thiadiazol-2-ylsulfanyl)-benzamide;
N-[2-azabicyclo[2.2.1]hept-5-yl]-4-(5-trifluoromethyl-pyrrol-2-yloxy)-benzamide;
N-[2-azabicyclo[2.2.1]hept-5-yl]-4-(3H-imidazol-4-yloxy)-benzamide;
N-[2-azabicyclo[2.2.1]hept-5-yl]-4-(isoxazol-2-yloxy)-benzamide;
N-[2-azabicyclo[2.2.1]hept-5-yl]-4-(isothiazol-2-yloxy)-benzamide;
N-[2-azabicyclo[2.2.1]hept-5-yl]-4-(pyrrol-2-ylsulfanyl)-benzamide;
N-[2-azabicyclo[2.2.1]hept-5-yl]-4-(3H-imidazol-4-ylsulfanyl)-benzamide;
N-[2-azabicyclo[2.2.1]hept-5-yl]-4-(isoxazol-2-ylsulfanyl)-benzamide;
N-[2-azabicyclo[2.2.1]hept-5-yl]-4-(isothiazol-2-ylsulfanyl)-benzamide;
N-[2-azabicyclo[2.2.1]hept-5-yl]-4-(6-methylpyridin-3-yloxy)-benzamide;
N-[2-azabicyclo[2.2.1]hept-5-yl]-4-(6-chloropyridin-3-yloxy)-benzamide;
N-[2-azabicyclo[2.2.1]hept-5-yl]-4-(6-methoxypyridin-3-yloxy)-benzamide;
N-[2-azabicyclo[2.2.1]hept-5-yl]-4-(6-trifluoromethyl-pyridin-3-yloxy)-benzamide;
N-[2-azabicyclo[2.2.1]hept-5-yl]-4-(2-chloropyridin-4-yloxy)-benzamide;
N-[2-azabicyclo[2.2.1]hept-5-yl]-4-(5-chloropyridin-2-yloxy)-benzamide;
N-[2-azabicyclo[2.2.1]hept-5-yl]-4-(4-chloropyridin-2-yloxy)-benzamide;
N-[2-azabicyclo[2.2.1]hept-5-yl]-4-(6-chloropyridin-2-yloxy)-benzamide;
N-[2-azabicyclo[2.2.1]hept-5-yl]-4-(5-chloropyridin-3-yloxy)-benzamide;
N-[2-azabicyclo[2.2.1]hept-5-yl]-4-(2-chloropyridin-3-yloxy)-benzamide;
N-[2-azabicyclo[2.2.1]hept-5-yl]-4-(4-chloropyridin-3-yloxy)-benzamide;
N-[2-azabicyclo[2.2.1]hept-5-yl]-4-(3-chloropyridin-4-yloxy)-benzamide;
N-[2-azabicyclo[2.2.1]hept-5-yl]-4-(3-chloropyridin-2-yloxy)-benzamide;
N-[2-azabicyclo[2.2.1]hept-5-yl]-4-(6-chloropyridin-3-ylsulfanyl)-benzamide;
N-[2-azabicyclo[2.2.1]hept-6-yl]-4-(4-hydroxyphenoxy)benzamide;
N-[2-azabicyclo[2.2.1]hept-6-yl]-4-(4-acetamidophenoxy)benzamide;
N-[2-azabicyclo[2.2.1]hept-6-yl]-4-phenoxybenzamide;
N-[2-azabicyclo[2.2.1]hept-6-yl]-4-benzylbenzamide;
N-[2-azabicyclo[2.2.1]hept-6-yl]-4-(phenylsulfanyl)-benzamide;
N-[2-azabicyclo[2.2.1]hept-6-yl]-3-phenoxybenzamide;
N-[2-azabicyclo[2.2.1]hept-6-yl]-4-(4-fluorophenoxy)benzamide;
N-[2-azabicyclo[2.2.1]hept-6-yl]-4-(2-fluorophenoxy)-benzamide;
N-[2-azabicyclo[2.2.1]hept-6-yl]-4-(3-fluorophenoxy)-benzamide;
N-[2-azabicyclo[2.2.1]hept-6-yl]-4-(2-chlorophenoxy)-benzamide;
N-[2-azabicyclo[2.2.1]hept-6-yl]-4-(3-chlorophenoxy)-benzamide;
N-[2-azabicyclo[2.2.1]hept-6-yl]-4-(4-chlorophenoxy)-benzamide;
N-[2-azabicyclo[2.2.1]hept-6-yl]-4-(2-methoxyphenoxy)-benzamide;
N-[2-azabicyclo[2.2.1]hept-6-yl]-4-(3-methoxyphenoxy)-benzamide;
N-[2-azabicyclo[2.2.1]hept-6-yl]-4-(4-methoxyphenoxy)-benzamide;
N-[2-azabicyclo[2.2.1]hept-6-yl]-4-(3-chlorophenyl-sulfanyl)benzamide;
N-[2-azabicyclo[2.2.1]hept-6-yl]-4-(4-chlorophenyl-sulfanyl)benzamide;
N-[2-azabicyclo[2.2.1]hept-6-yl]-4-(2-chlorophenyl-sulfanyl)benzamide;
N-[2-azabicyclo[2.2.1]hept-6-yl]-4-(4-methoxyphenyl-sulfanyl)benzamide;
N-[2-azabicyclo[2.2.1]hept-6-yl]-4-(3-methoxyphenyl-sulfanyl)benzamide;
N-[2-azabicyclo[2.2.1]hept-6-yl]-4-(2-methoxyphenyl-sulfanyl)benzamide;
N-[2-azabicyclo[2.2.1]hept-6-yl]-4-(4-aminophenoxy)-benzamide;
N-[2-azabicyclo[2.2.1]hept-6-yl]-4-(3-aminophenoxy)-benzamide;
N-[2-azabicyclo[2.2.1]hept-6-yl]-4-(2-aminophenoxy)-benzamide;
N-[2-azabicyclo[2.2.1]hept-6-yl]-4-(4-acetylphenoxy)-benzamide;
N-[2-azabicyclo[2.2.1]hept-6-yl]-4-(3-acetylphenoxy)-benzamide;
N-[2-azabicyclo[2.2.1]hept-6-yl]-4-(2-acetylphenoxy)-benzamide;
N-[2-azabicyclo[2.2.1]hept-6-yl]-4-(4-carbamoylphenoxy)-benzamide;
N-[2-azabicyclo[2.2.1]hept-6-yl]-4-(3-carbamoylphenoxy)-benzamide;
N-[2-azabicyclo[2.2.1]hept-6-yl]-4-(2-carbamoylphenoxy)-benzamide;
N-[2-azabicyclo[2.2.1]hept-6-yl]-4-(4-cyanophenoxy)-benzamide;
N-[2-azabicyclo[2.2.1]hept-6-yl]-4-(3-cyanophenoxy)-benzamide;

N-[2-azabicyclo[2.2.1]hept-6-yl]-4-(2-cyanophenoxy)-benzamide;
N-[2-azabicyclo[2.2.1]hept-6-yl]-4-(thiophen-2-yloxy)-benzamide;
N-[2-azabicyclo[2.2.1]hept-6-yl]-4-(5-methylthiophen-2-yloxy)-benzamide;
N-[2-azabicyclo[2.2.1]hept-6-yl]-4-(5-chlorothiophen-2-yloxy)-benzamide;
N-[2-azabicyclo[2.2.1]hept-6-yl]-4-(5-methoxythiophen-2-yloxy)-benzamide;
N-[2-azabicyclo[2.2.1]hept-6-yl]-4-(5-trifluoromethyl-thiophen-2-yloxy)-benzamide;
N-[2-azabicyclo[2.2.1]hept-6-yl]-4-(4-methylthiophen-2-yloxy)-benzamide;
N-[2-azabicyclo[2.2.1]hept-6-yl]-4-(4-chlorothiophen-2-yloxy)-benzamide;
N-[2-azabicyclo[2.2.1]hept-6-yl]-4-(4-methoxythiophen-2-yloxy)-benzamide;
N-[2-azabicyclo[2.2.1]hept-6-yl]-4-(4-trifluoromethyl-thiophen-2-yloxy)-benzamide;
N-[2-azabicyclo[2.2.1]hept-6-yl]-4-(furan-2-yloxy)-benzamide;
N-[2-azabicyclo[2.2.1]hept-6-yl]-4-(5-methylfuran-2-yloxy)-benzamide;
N-[2-azabicyclo[2.2.1]hept-6-yl]-4-(5-chlorofuran-2-yloxy)-benzamide;
N-[2-azabicyclo[2.2.1]hept-6-yl]-4-(5-methoxyfuran-2-yloxy)-benzamide;
N-[2-azabicyclo[2.2.1]hept-6-yl]-4-(5-trifluoromethyl-furan-2-yloxy)-benzamide;
N-[2-azabicyclo[2.2.1]hept-6-yl]-4-(4-methylfuran-2-yloxy)-benzamide;
N-[2-azabicyclo[2.2.1]hept-6-yl]-4-(4-chlorofuran-2-yloxy)-benzamide;
N-[2-azabicyclo[2.2.1]hept-6-yl]-4-(4-methoxyfuran-2-yloxy)-benzamide;
N-[2-azabicyclo[2.2.1]hept-6-yl]-4-(4-trifluoromethyl-furan-2-yloxy)-benzamide;
N-[2-azabicyclo[2.2.1]hept-6-yl]-4-(oxazol-2-yloxy)-benzamide;
N-[2-azabicyclo[2.2.1]hept-6-yl]-4-(oxazol-5-yloxy)-benzamide;
N-[2-azabicyclo[2.2.1]hept-6-yl]-4-(thiazol-2-yloxy)-benzamide;
N-[2-azabicyclo[2.2.1]hept-6-yl]-4-(thiazol-5-yloxy)-benzamide;
N-[2-azabicyclo[2.2.1]hept-6-yl]-4-([1,3,4]oxadiazol-2-yloxy)-benzamide;
N-[2-azabicyclo[2.2.1]hept-6-yl]-4-([1,3,4]thiadiazol-2-yloxy)-benzamide;
N-[2-azabicyclo[2.2.1]hept-6-yl]-4-(4-aminophenyl-sulfanyl)-benzamide;
N-[2-azabicyclo[2.2.1]hept-6-yl]-4-(3-aminophenyl-sulfanyl)-benzamide;
N-[2-azabicyclo[2.2.1]hept-6-yl]-4-(2-aminophenyl-sulfanyl)-benzamide;
N-[2-azabicyclo[2.2.1]hept-6-yl]-4-(4-acetylphenyl-sulfanyl)-benzamide;
N-[2-azabicyclo[2.2.1]hept-6-yl]-4-(3-acetylphenyl-sulfanyl)-benzamide;
N-[2-azabicyclo[2.2.1]hept-6-yl]-4-(2-acetylphenyl-sulfanyl)-benzamide;
N-[2-azabicyclo[2.2.1]hept-6-yl]-4-(4-carbamoylphenyl-sulfanyl)-benzamide;
N-[2-azabicyclo[2.2.1]hept-6-yl]-4-(3-carbamoylphenyl-sulfanyl)-benzamide;
N-[2-azabicyclo[2.2.1]hept-6-yl]-4-(2-carbamoylphenyl-sulfanyl)-benzamide;
N-[2-azabicyclo[2.2.1]hept-6-yl]-4-(4-hydroxyphenyl-sulfanyl)-benzamide;
N-[2-azabicyclo[2.2.1]hept-6-yl]-4-(3-hydroxyphenyl-sulfanyl)-benzamide;
N-[2-azabicyclo[2.2.1]hept-6-yl]-4-(2-hydroxyphenyl-sulfanyl)-benzamide;
N-[2-azabicyclo[2.2.1]hept-6-yl]-4-(4-acetamidophenyl-sulfanyl)-benzamide;
N-[2-azabicyclo[2.2.1]hept-6-yl]-4-(3-acetamidophenyl-sulfanyl)-benzamide;
N-[2-azabicyclo[2.2.1]hept-6-yl]-4-(2-acetamidophenyl-sulfanyl)-benzamide;
N-[2-azabicyclo[2.2.1]hept-6-yl]-4-(thiophen-2-ylsulfanyl)-benzamide;
N-[2-azabicyclo[2.2.1]hept-6-yl]-4-(5-methylthiophen-2-ylsulfanyl)-benzamide;
N-[2-azabicyclo[2.2.1]hept-6-yl]-4-(5-chlorothiophen-2-ylsulfanyl)-benzamide;
N-[2-azabicyclo[2.2.1]hept-6-yl]-4-(5-trifluoromethyl-thiophen-2-ylsulfanyl)-benzamide;
N-[2-azabicyclo[2.2.1]hept-6-yl]-4-(furan-2-ylsulfanyl)-benzamide;
N-[2-azabicyclo[2.2.1]hept-6-yl]-4-(5-methylfuran-2-ylsulfanyl)-benzamide;
N-[2-azabicyclo[2.2.1]hept-6-yl]-4-(5-chlorofuran-2-ylsulfanyl)-benzamide;
N-[2-azabicyclo[2.2.1]hept-6-yl]-4-(oxazol-2-ylsulfanyl)-benzamide;
N-[2-azabicyclo[2.2.1]hept-6-yl]-4-(5-chlorooxazol-2-ylsulfanyl)-benzamide;
N-[2-azabicyclo[2.2.1]hept-6-yl]-4-(5-methoxyoxazol-2-ylsulfanyl)-benzamide;
N-[2-azabicyclo[2.2.1]hept-6-yl]-4-(5-trifluoromethyl-oxazol-2-ylsulfanyl)-benzamide;
N-[2-azabicyclo[2.2.1]hept-6-yl]-4-(oxazol-2-ylsulfanyl)-benzamide;
N-[2-azabicyclo[2.2.1]hept-6-yl]-4-(oxazol-5-ylsulfanyl)-benzamide;
N-[2-azabicyclo[2.2.1]hept-6-yl]-4-(thiazol-2-ylsulfanyl)-benzamide;
N-[2-azabicyclo[2.2.1]hept-6-yl]-4-(thiazol-5-ylsulfanyl)-benzamide;
N-[2-azabicyclo[2.2.1]hept-6-yl]-4-([1,3,4]oxadiazol-2-ylsulfanyl)-benzamide;
N-[2-azabicyclo[2.2.1]hept-6-yl]-4-([1,3,4]thiadiazol-2-ylsulfanyl)-benzamide;
N-[2-azabicyclo[2.2.1]hept-6-yl]-4-(5-trifluoromethyl-pyrrol-2-yloxy)-benzamide;
N-[2-azabicyclo[2.2.1]hept-6-yl]-4-(3H-imidazol-4-yloxy)-benzamide;
N-[2-azabicyclo[2.2.1]hept-6-yl]-4-(isoxazol-2-yloxy)-benzamide;
N-[2-azabicyclo[2.2.1]hept-6-yl]-4-(isothiazol-2-yloxy)-benzamide;
N-[2-azabicyclo[2.2.1]hept-6-yl]-4-(pyrrol-2-ylsulfanyl)-benzamide;
N-[2-azabicyclo[2.2.1]hept-6-yl]-4-(3H-imidazol-4-ylsulfanyl)-benzamide;
N-[2-azabicyclo[2.2.1]hept-6-yl]-4-(isoxazol-2-ylsulfanyl)-benzamide;
N-[2-azabicyclo[2.2.1]hept-6-yl]-4-(isothiazol-2-ylsulfanyl)-benzamide;
N-[2-azabicyclo[2.2.1]hept-6-yl]-4-(6-methylpyridin-3-yloxy)-benzamide;
N-[2-azabicyclo[2.2.1]hept-6-yl]-4-(6-chloropyridin-3-yloxy)-benzamide;
N-[2-azabicyclo[2.2.1]hept-6-yl]-4-(6-methoxypyridin-3-yloxy)-benzamide;

N-[2-azabicyclo[2.2.1]hept-6-yl]-4-(6-trifluoromethyl-pyridin-3-yloxy)-benzamide;
N-[2-azabicyclo[2.2.1]hept-6-yl]-4-(2-chloropyridin-4-yloxy)-benzamide;
N-[2-azabicyclo[2.2.1]hept-6-yl]-4-(5-chloropyridin-2-yloxy)-benzamide;
N-[2-azabicyclo[2.2.1]hept-6-yl]-4-(4-chloropyridin-2-yloxy)-benzamide;
N-[2-azabicyclo[2.2.1]hept-6-yl]-4-(6-chloropyridin-2-yloxy)-benzamide;
N-[2-azabicyclo[2.2.1]hept-6-yl]-4-(5-chloropyridin-3-yloxy)-benzamide;
N-[2-azabicyclo[2.2.1]hept-6-yl]-4-(2-chloropyridin-3-yloxy)-benzamide;
N-[2-azabicyclo[2.2.1]hept-6-yl]-4-(4-chloropyridin-3-yloxy)-benzamide;
N-[2-azabicyclo[2.2.1]hept-6-yl]-4-(3-chloropyridin-4-yloxy)-benzamide;
N-[2-azabicyclo[2.2.1]hept-6-yl]-4-(3-chloropyridin-2-yloxy)-benzamide; or
N-[2-azabicyclo[2.2.1]hept-6-yl]-4-(6-chloropyridin-3-ylsulfanyl)-benzamide, any of which is optionally substituted on the Azabicyclo moiety with lower alkyl for $R_2$, including methyl, as discussed herein, provided that the Azabicyclo moiety has only one substituent for $R_2$.

Materials and Methods for Determining α7 nAChR Agonist Activity

Cell-based Assay for Measuring the $EC_{50}$ of α7 nAChR Agonists

Construction and Expression of the α7-5HT$_3$ Receptor

The cDNA encoding the N-terminal 201 amino acids from the human α7 nAChR that contain the ligand binding domain of the ion channel was fused to the cDNA encoding the pore forming region of the mouse 5HT$_3$ receptor as described by Eisele J L, et al., Chimaeric nicotinic-serotonergic receptor combines distinct ligand binding and channel specificities, Nature (1993), Dec. 2;366(6454):479–83, and modified by Groppi, et al., WO 00/73431. The chimeric α7-5HT$_3$ ion channel was inserted into pGS175 and pGS179 which contain the resistance genes for G-418 and hyrgromycin B, respectively. Both plasmids were simultaneously transfected into SH-EP1 cells and cell lines were selected that were resistant to both G-418 and hyrgromycin B. Cell lines expressing the chimeric ion channel were identified by their ability to bind fluorescent α-bungarotoxin on their cell surface. The cells with the highest amount of fluorescent α-bungarotoxin binding were isolated using a Fluorescent Activated Cell Sorter (FACS). Cell lines that stably expressed the chimeric α7-5HT$_3$ were identified by measuring fluorescent α-bungarotoxin binding after growing the cells in minimal essential medium containing nonessential amino acids supplemented with 10% fetal bovine serum, L-glutamine, 100 units/ml penicillin/streptomycin, 250 ng/mg fungizone, 400 μg/ml hygromycin B, and 400 μg/ml G-418 at 370° C. with 6% $CO_2$ in a standard mammalian cell incubator for at least 4 weeks in continuous culture.

Assay of the Activity of the Chimeric α7-5HT$_3$ Receptor

To assay the activity of the α7-5HT$_3$ ion channel, cells expressing the channel were plated into each well of either a 96 or 384 well dish (Corning #3614) and grown to confluence prior to assay. On the day of the assay, the cells were loaded with a 1:1 mixture of 2 mM Calcium Green 1, AM (Molecular Probes) dissolved in anhydrous DMSO and 20% pluronic F-127 (Molecular Probes). This solution was added directly to the growth media of each well to achieve a final concentration 2 μM. The cells were incubated with the dye for 60 min at 370° C. and then washed with a modified version of Earle's balanced salt solution (MMEBSS) as described in WO 00/73431. The ion conditions of the MMEBSS was adjusted to maximize the flux of calcium ion through the chimeric α7-5HT$_3$ ion channel as described in WO 00/73431. The activity of compounds on the chimeric α7-5HT$_3$ ion channel was analyzed on FLIPR. The instrument was set up with an excitation wavelength of 488 nanometers using 500 milliwatts of power. Fluorescent emission was measured above 525 nanometers with an appropriate F-stop to maintain a maximal signal to noise ratio. Agonist activity of each compound was measured by directly adding the compound to cells expressing the chimeric α7-5HT$_3$ ion channel and measuring the resulting increase in intracellular calcium that is caused by the agonist-induced activation of the chimeric ion channel. The assay is quantitative such that concentration-dependent increase in intracelluar calcium is measured as concentration-dependent change in Calcium Green fluorescence. The effective concentration needed for a compound to cause a 50% maximal increase in intracellular calcium is termed the $EC_{50}$. The most active compounds would have $EC_{50}$ values from about 0.01 μM to about 50 μM.

Binding Constants

Another way for measuring α7 nAChR agonist activity is to determine binding constants of a potential agonist in a competition binding assay. For α7 nAChR agonists, there is good correlation between functional $EC_{50}$ values using the chimeric α7-5HT$_3$ ion channel as a drug target and binding affinity of compounds to the endogenous α7 nAChR.

Membrane Preparation

Male Sprague-Dawley rats (300–350 g) are sacrificed by decapitation and the brains (whole brain minus cerebellum) are dissected quickly, weighed and homogenized in 9 volumes/g wet weight of ice-cold 0.32 M sucrose using a rotating pestle on setting 50 (10 up and down strokes). The homogenate is centrifuged at 1,000×g for 10 minutes at 4° C. The supernatant is collected and centrifuged at 20,000×g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at rt and diluted with Kreb's −20 mM Hepes buffer pH 7.0 (at rt) containing 4.16 mM $NaHCO_3$, 0.44 mM $KH_2PO_4$, 127 mM NaCl, 5.36 mM KCl, 1.26 mM $CaCl_2$, and 0.98 mM $MgCl_2$, so that 25–150 μg protein are added per test tube. Proteins are determined by the Bradford method (Bradford, M. M., *Anal. Biochem.*, 72, 248–254, 1976) using bovine serum albumin as the standard.

Binding Assay

For saturation studies, 0.4 mL homogenate are added to test tubes containing buffer and various concentrations of radioligand, and are incubated in a final volume of 0.5 mL for 1 hour at 25° C. Nonspecific binding was determined in tissues incubated in parallel in the presence of 0.05 mls MLA for a final concentration of 1 μM, added before the radioligand. In competition studies, drugs are added in increasing concentrations to the test tubes before addition of 0.05 mls [$^3$H]-MLA for a final concentration 3.0 to 4.0 nM. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis

In competition binding studies, the inhibition constant (Ki) was calculated from the concentration dependent inhibition of [$^3$H]-MLA binding obtained from non-linear regression fitting program according to the Cheng-Prusoff equation (Cheng, Y. C. and Prussoff, W. H., *Biochem. Pharmacol.*, 22, p. 3099–3108, 1973). Hill coefficients were obtained using non-linear regression (GraphPad Prism sigmoidal dose-response with variable slope).

What is claimed:

1. A compound of the Formula I:

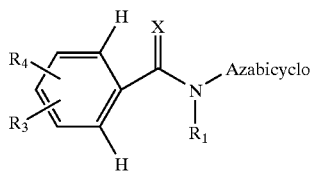

Formula I wherein X is O or S; Azabicyclo is:

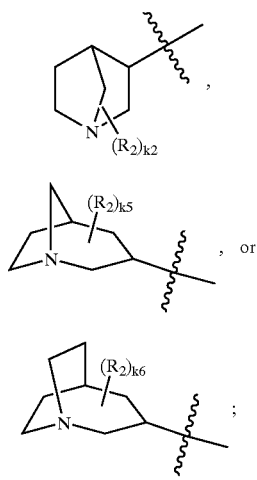

$R_1$ is independently H, alkyl, cycloalkyl, halogenated alkyl, and aryl;

$R_2$ is F, Cl, Br, I, alkyl, halogenated alkyl, substituted alkyl, cycloalkyl, or aryl, provided that when Azabicyclo is I, $R_2$ is alkyl, halogenated alkyl, substituted alkyl, cycloalkyl, or aryl, and further provided that $R_2$ is absent when any of $k_2$, $k_5$, or $k_6$ is 0;

$k_2$ is 0 or 1;

$k_5$ is 0, 1, or 2;

$k_6$ is 0, 1, or 2;

$R_3$ is H, F, Cl, Br, I, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, aryl, $R_7$, $R_9$, —$OR_8$, —$SR_8$, —$S(O)_2R_8$, —$S(O)R_8$, —$OS(O)_2R_8$, —$N(R_8)_2$, —$C(O)R_8$, —$C(S)R_8$, —$C(O)OR_8$, —CN, —$C(O)N(R_8)_2$, —$NR_8C(O)R_8$, —$S(O)_2N(R_8)_2$, —$NR_8S(O)_2R_8$, —$NO_2$, —$N(R_8)C(O)N(R_8)_2$, substituted alkyl, substituted alkenyl, substituted alkynyl, substituted cycloalkyl, substituted heterocycloalkyl, phenyl, phenyl having 1–4 substituents independently selected from F, Cl, Br, I and $R_{21}$, naphthyl, or naphthyl having 1–4 substituents independently selected from F, Cl, Br, I, $R_{21}$;

$R_4$ is —O—$R_5$, —S—$R_5$, —S(O)—$R_5$, —C(O)—$R_5$, or alkyl substituted on the ω carbon with $R_5$ where said ω carbon is determined by counting the longest carbon chain of the alkyl moiety with the C-1 carbon being the carbon attached to the phenyl ring of the core molecule and the ω carbon being the carbon furthest from said C-1 carbon;

$R_5$ is aryl, $R_7$, or $R_9$;

$R_7$ is 5-membered heteroaromatic mono-cyclic moieties containing within the ring 1–3 heteroatoms independently selected from —O—, —N—, —N($R_{14}$)—, and —S—, and having 0–1 substituent selected from $R_{12}$ and 0–3 substituents independently selected from F, Cl, Br, or I, or $R_7$ is a 9-membered fused-ring moiety having a 6-membered ring fused to a 5-membered ring and having the formula:

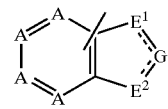

wherein each A is independently $CR_{18}$ or N, provided that only up to one A is N, E<1> and E<2> are independently selected from $CR_{18}$, O, S, or $NR_{14}$, and G is $CR_{18}$, provided that $R_{18}$ or $R_{14}$ of E<1>, E<2>, and G can be a bond when - - - forms a double bond and further provided that $R_{18}$ or $R_{14}$ can be a bond for bonding $R_7$ to a moiety to which it is attached;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from —N— and having 0–1 substituent selected from $R_{12}$ and 0–3 substituent(s) independently selected from F, Cl, Br, or I, or $R_9$ is 10-membered heteroaromatic bi-cyclic moieties containing within one or both rings 1–3 heteroatoms selected from =N—, each 10-membered fused-ring moiety having 0–1 substituent selected from $R_{12}$ and 0–3 substituent(s) independently selected from F, Cl, Br, or I and having a bond for bonding $R_9$ to a moiety to which it is attached where valency allows;

Each $R_{11}$ is independently H, alkyl, cycloalkyl, heterocycloalkyl, halogenated alkyl, halogenated cycloalkyl, or halogenated heterocycloalkyl;

$R_{12}$ is —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_1$, —$NO_2$, —$C(O)NR_{11}R_{11}$, —CN, —$NR_{11}C(O)R_1$, —$S(O)_2NR_{11}R_{11}$, or —$NR_{11}S(O)_2R_{,1}$;

$R_{13}$ is —$OR_1$, —$SR_{11}$, —$NR_{11}R_{11}$, —$C(O)R_{11}$, —$C(O)NR_{11}R_{11}$, —CN, —$CF_3$, to —$NR_{11}C(O)R_1$, —$S(O)_2NR_{11}R_{11}$, —$NR_{11}S(O)_2R_{11}$, or —$NO_2$;

$R_{14}$ is a bond, H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, phenyl having 1 substituent selected from $R_{20}$ and further having 0–3 substituents independently selected from F, Cl, Br, or I;

Each $R_{18}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$N(R,_1)_2$, —$C(O)R_1$, —$NO_2$, —$C(O)N(R_{11})_2$, —CN, —$NR_{11}C(O)R_1$, —$S(O)_2N(R_{11})_2$, or —$NR_{11}S(O)_2R_1$, F, Cl, Br, or I, or a bond;

$R_{20}$ is alkyl, cycloalkyl, heterocycloalkyl, halogenated alkyl, halogenated cycloalkyl, halogenated heterocycloalkyl, —$OR_{11}$, —$SR_{11}$, —$N(R_{11})_2$, —$C(O)R_1$, —$C(O)N(R_{11})_2$, —CN, —$NR_{11}C(O)R_{11}$, —$S(O)_2N(R_{11})_2$, —$NR_{11}S(O)_2R_{11}$, —$NO_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or $R_{13}$;

Each $R_{21}$ is independently alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or phenyl having 1 substituent selected from $R_{20}$ and further having 0–3 substituents independently selected from F, Cl, Br, or I;

or pharmaceutically acceptable salt thereof.

2. The compound of claim 1, wherein X is O.

3. The compound of claim 2, wherein $R_1$ is H, lower alkyl, or lower cycloalkyl, wherein $R_2$ is lower alkyl, lower halogenated alkyl, or lower substituted alkyl, provided that $R_2$ is present, or $R_2$ is absent, and wherein $k_2$, $k_5$, or $k_6$ is 0, or 1.

4. The compound of claim 3, wherein $R_3$ is H, F, Cl, Br, I, lower alkyl, lower halogenated alkyl, —$OR_8$, —$N(R_8)_2$, —$C(O)NH(R_8)$, —$NR_8C(O)R_8$.

5. The compound of claim 4, wherein $R_1$ is H.

6. The compound of claim 5, wherein Azabicyclo is II, V, or VI.

7. The compound of claim 6, wherein each $k_2$, $k_5$, or $k_6$ is 0.

8. The compound of claim 7, wherein the compound is exo-N-[(4S)-1-azabicyclo[2.2.11]hept-3-yl]-4-(4-acetamidophenoxy)benzamide;

exo-N-[(4S)-1-azabicyclo[2.2.1]hept-3-yl]-4-(4-acetamidophenoxy)benzamide;

exo-N-[(4S)-1-azabicyclo[2.2.1]hept-3-yl]-4-phenoxybenzamide;

exo-N-[(4S)-1-azabicyclo[2.2.1]hept-3-yl]-4-benzylbenzamide;

exo-N-[(4S)-1-azabicyclo[2.2.1]hept-3-yl]-4-(phenylsulfanyl)-benzamide;

exo-N-[(4S)-1-azabicyclo[2.2.1]hept-3-yl]-3-phenoxybenzamide;

exo-N-[(4S)-1-azabicyclo[2.2.1]hept-3-yl]-4-(4-fluorophenoxy)benzamide;

exo-N-[(4S)-1-azabicyclo[2.2.1]hept-3-yl]-4-(2-fluorophenoxy)-benzamide;

exo-N-[(4S)-1-azabicyclo[2.2.1]hept-3-yl]-4-(3-fluorophenoxy)-benzamide;

exo-N-[(4S)-1-azabicyclo[2.2.1]hept-3-yl]-4-(2-chlorophenoxy)-benzamide;

exo-N-[(4S)-1-azabicyclo[2.2.1]hept-3-yl]-4-(3-chlorophenoxy)-benzamide;

exo-N-[(4S)-1-azabicyclo[2.2.1]hept-3-yl]-4-(4-chlorophenoxy)-benzamide;

exo-N-[(4S)-1-azabicyclo[2.2.1]hept-3-yl]-4-(2-methoxyphenoxy)-benzamide;

exo-N-[(4S)-1-azabicyclo[2.2.1]hept-3-yl]-4-(3-methoxyphenoxy)-benzamide;

exo-N-[(4S)-1-azabicyclo[2.2.1]hept-3-yl]-4-(4-methoxyphenoxy)-benzamide;

exo-N-[(4S)-1-azabicyclo[2.2.1]hept-3-yl]-4-(3-chlorophenylsulfanyl)benza-mide;

exo-N-[(4S)-1-azabicyclo[2.2.1]hept-3-yl]-4-(4-chlorophenyl-sulfanyl)benzamide; exo-N-[(4S)-1-azabicyclo[2.2.1]hept-3-yl]-4-(2-chlorophenyl-sulfanyl)benzamide; exo-N-[(4S)-1-azabicyclo[2.2.1]hept-3-yl]-4-(4-methoxyphenyl-sulfanyl)benzamide; exo-N-[(4S)-1-azabicyclo[2.2.1]hept-3-yl]-4-(3-methoxyphenyl-sulfanyl)benzamide; exo-N-[(4S)-1-azabicyclo[2.2.1]hept-3-yl]-4-(2-methoxyphenyl-sulfanyl)benzamide; exo-N-[(4S)-1-azabicyclo[2.2.1]hept-3-yl]-4-(4-aminophenoxy)-benzamide; exo-N-[(4S)-1-azabicyclo[2.2.1]hept-3-yl]-4-(3-aminophenoxy)-benzamide; exo-N-[(4S)-1-azabicyclo[2.2.1]hept-3-yl]-4-(2-aminophenoxy)-benzamide; exo-N-[(4S)-1-azabicyclo[2.2.1]hept-3-yl]-4-(4-acetylphenoxy)-benzamide; exo-N-[(4S)-1-azabicyclo[2.2.1]hept-3-yl]-4-(3-acetylphenoxy)-benzamide; exo-N-[(4S)-1-azabicyclo[2.2.1]hept-3-yl]-4-(2-acetylphenoxy)-benzamide; exo-N-[(4S)-1-azabicyclo[2.2.1]hept-3-yl]-4-(4-carbamoylphenoxy)-benzamide; exo-N-[(4S)-1-azabicyclo[2.2.1]hept-3-yl]-4-(3-carbamoylphenoxy)-benzamide; exo-N-[(4S)-1-azabicyclo[2.2.1]hept-3-yl]-4-(2-carbamoylphenoxy)-benzamide; exo-N-[(4S)-1-azabicyclo[2.2.1]hept-3-yl]-4-(4-cyanophenoxy)-benzamide; exo-N-[(4S)-1-azabicyclo[2.2.1]hept-3-yl]-4-(3-cyanophenoxy)-benzamide; exo-N-[(4S)-1-azabicyclo[2.2.1]hept-3-yl]-4-(2-cyanophenoxy)-benzamide; exo-N-[(4S)-1-azabicyclo[2.2.1]hept-3-yl]-4-(thiophen-2-yloxy)-benzamide; exo-N-[(4S)-1-azabicyclo[2.2.1]hept-3-yl]-4-(5-methylthiophen-2-yloxy)-benzamide; exo-N-[(4S)-1-azabicyclo[2.2.1]hept-3-yl]-4-(5-chlorothiophen-2-yloxy)-benzamide; exo-N-[(4S)-1-azabicyclo[2.2.1]hept-3-yl]-4-(5-methoxythiophen-2-yloxy)-benzamide;

exo-N-[(4S)-1-azabicyclo[2.2.1]hept-3-yl]-4-(5-trifluoromethylthiophen-2-yloxy)-benzamide; exo-N-[(4S)-1-azabicyclo[2.2.1]hept-3-yl]-4-(4-methylthiophen-2-yloxy)-benzamide; exo-N-[(4S)-1-azabicyclo[2.2.1]hept-3-yl]-4-(4-chlorothiophen-2-yloxy)-benzamide; exo-N-[(4S)-1-azabicyclo[2.2.1]hept-3-yl-]-4-(4-methoxythiophen-2-yloxy)-benzamide; exo-N-[(4S)-1-azabicyclo[2.2.1]hept-3-yl]-4-(4-trifluoromethylthiophen-2-yloxy)-benzamide;

exo-N-[(4S)-1-azabicyclo[2.2.1]hept-3-yl]-4-(furan-2-yloxy)-benzamide;

exo-N-[(4S)-1-azabicyclo[2.2.1]hept-3-yl]-4-(5-methylfuran-2-yloxy)-benza-mide;

exo-N-[(4S)-1-azabicyclo[2.2.1]hept-3-yl]-4-(5-chlorofuran-2-yloxy)-benzamide;

exo-N-[(4S)-1-azabicyclo[2.2.1]hept-3-yl]-4-(5-methoxyfuran-2-yloxy)-benzamide; exo-N-[(4S)-1-azabicyclo[2.2.1]hept-3-yl]-4-(5-trifluoromethylfuran-2-yloxy)-benzamide; exo-N-[(4S)-1-azabicyclo[2.2.1]hept-3-yl]-4-(4-methylfuran-2-yloxy)-benzamide; exo-N-[(4S)-1-azabicyclo[2.2.1]hept-3-yl]-4-(4-chlorofuran-2-yloxy)-benzamide; exo-N-[(4S)-1-azabicyclo[2.2.1]hept-3-yl]-4-(4-methoxyfuran-2-yloxy)-benzamide; exo-N-[(4S)-1-azabicyclo[2.2.1]hept-3-yl]-4-(4-trifluoromethylfuran-2-yloxy)-benzamide;

exo-N-[(4S)-1-azabicyclo[2.2.1]hept-3-yl]-4-(oxazol-2-yloxy)-benzamide;

exo-N-[(4S)-1-azabicyclo[2.2.1]hept-3-yl]-4-(oxazol-5-yloxy)-benzamide;

exo-N-[(4S)-1-azabicyclo[2.2.1]hept-3-yl]-4-(thiazol-2-yloxy)-benzamide;
exo-N-[(4S)-1-azabicyclo[2.2.1]hept-3-yl]-4-(thiazol-5-yloxy)-benzamide;
exo-N-[(4S)-1-azabicyclo[2.2.1]hept-3-yl]-4-([1,3,4]oxadiazol-2-yloxy)-benzamide; exo-N-[(4S)-1-azabicyclo[2.2.1]hept-3-yl]-4-([1,3,4]thiadiazol-2-yloxy)-benzamide; exo-N-[(4S)-1-azabicyclo[2.2.1]hept-3-yl-4-(4-aminophenylsulfanyl)-benzamide; exo-N-[(4S)-1-azabicyclo[2.2.1]hept-3-yl]-4-(3-aminophenylsulfanyl)-benzamide; exo-N-[(4S)-1-azabicyclo[2.2.1]hept-3-yl]-4-(2-aminophenylsulfanyl)-benzamide; exo-N-[(4S)-1-azabicyclo[2.2.1]hept-3-yl]-4-(4-acetylphenylsulfanyl)-benzamide; exo-N-[(4S)-1-azabicyclo[2.2.1]hept-3-yl]-4-(3-acetylphenylsulfanyl)-benzamide; exo-N-[(4S)-1-azabicyclo[2.2.1]hept-3-yl]-4-(2-acetylphenylsulfanyl)-benzamide; exo-N-[(4S)-1-azabicyclo[2.2.1]hept-3-yl]-4-(4-carbamoylphenylsulfanyl)-benzamide;
exo-N-[(4S)-1-azabicyclo[2.2.1]hept-3-yl]-4-(3-carbamoylphenylsulfanyl)-benzamide; exo-N-[(4S)-1-azabicyclo[2.2.1]hept-3-yl]-4-(2-carbamoylphenylsulfanyl)-benzamide; exo-N-[(4S)-1-azabicyclo[2.2.1]hept-3-yl]-4-(4-hydroxyphenylsulfanyl)-benzamide; exo-N-[(4S)-1-azabicyclo[2.2.1]hept-3-yl]-4-(3-hydroxyphenylsulfanyl)-benzamide; exo-N-[(4S)-1-azabicyclo[2.2.1]hept-3-yl]-4-(2-hydroxyphenylsulfanyl)-benzamide; exo-N-[(4S)-1-azabicyclo[2.2.1]hept-3-yl]-4-(4-acetamidophenylsulfanyl)-benzamide; exo-N-[(4S)-1-azabicyclo[2.2.1]hept-3-yl]-4-(3-acetamidophenylsulfanyl)-benzamide;
exo-N-[(4S)-1-azabicyclo[2.2.1]hept-3-yl]-4-(2-acetamidophenylsulfanyl)-benzamide; exo-N-[(4S)-1-azabicyclo[2.2.1]hept-3-yl]-4-(thiophen-2-ylsulfanyl)-benzamide; exo-N-[(4S)-1-azabicyclo[2.2.1]hept-3-yl]-4-(5-methylthiophen-2-ylsulfanyl)-benzamide; exo-N-[(4S)-1-azabicyclo[2.2.1]hept-3-yl]-4-(5-chlorothiophen-2-ylsulfanyl)-benzamide; exo-N-[(4S)-1-azabicyclo[2.2.1]hept-3-yl]-4-(5-trifluoromethylthiophen-2-ylsulfanyl)benzamide;
exo-N-[(4S)-1-azabicyclo[2.2.1]hept-3-yl]-4-(furan-2-ylsulfanyl)-benzamid-e;
exo-N-[(4S)-1-azabicyclo[2.2.1]hept-3-yl]-4-(5-methylfuran-2-ylsulfanyl)-benzamide; exo-N-[(4S)-1-azabicyclo[2.2.1]hept-3-yl]-4-(5-chlorofuran-2-ylsulfanyl)-benzamide; exo-N-[(4S)-1-azabicyclo[2.2.1]hept-3-yl]-4-(oxazol-2-ylsulfanyl)-benzamide; exo-N-[(4S)-1-azabicyclo[2.2.1]hept-3-yl]-4-(5-chlorooxazol-2-ylsulfanyl)-benzamide; exo-N4(4S)-1-azabicyclo[2.2.1]hept-3-yl]-4-(5-methoxyoxazol-2-ylsulfanyl)-benzamide; exo-N-[(4S)-1-azabicyclo[2.2.1]hept-3-yl]-4-(5-trifluoromethyloxazol-2-ylsulfanyl)-benzamide;
exo-N-[(4S)-1-azabicyclo[2.2.1]hept-3-yl]-4-(oxazol-2-ylsulfanyl)-benzami-de;
exo-N-[(4S)-1-azabicyclo[2.2.1]hept-3-yl]-4-(oxazol-5-ylsulfanyl)-benz-amide;
exo-N-[(4S)-1-azabicyclo[2.2.1]hept-3-yl]-4-(thiazol-2-ylsulfanyl)-benzamide;
exo-N-[(4S)-1-azabicyclo[2.2.1]hept-3-yl]-4-(thiazol-5-ylsulfan-yl)-benzamide;
exo-N-[(4S)-1-azabicyclo[2.2.1]hept-3-yl]-4-([1,3,4]oxadiazol-2-ylsulfanyl)-benzamide; exo-N-[(4S)-1-azabicyclo[2.2.1]hept-3-yl]-4-([1,3,4]thiadiazol-2-ylsulfanyl)-benzamide; exo-N-[(4S)-1-azabicyclo[2.2.1]hept-3-yl]-4-(5-trifluoromethylpyrrol-2-yloxy)-benzamide;

exo-N-[(4S)-1-azabicyclo[2.2.1]hept-3-yl]-4-(3H-imidazol-4-yloxy)-benzami-de;
exo-N-[(4S)-1-azabicyclo[2.2.1]hept-3-yl]-4-(isoxazol-2-yloxy)-benzami-de;
exo-N-[(4S)-1-azabicyclo[2.2.1]hept-3-yl]-4-(isothiazol-2-yloxy)-benza-mide;
exo-N-[(4S)-1-azabicyclo[2.2.1]hept-3-yl]-4-(pyrrol-2-ylsulfanyl)-be-nzamide;
exo-N-[(4S)-1-azabicyclo[2.2.1]hept-3-yl]-4-(3H-imidazol-4-ylsulfanyl)-benzamide; exo-N-[(4S)-1-azabicyclo[2.2.1]hept-3-yl-4-(isoxazol-2-ylsulfanyl)-benzamide; exo-N-[(4S)-1-azabicyclo[2.2.1]hept-3-yl]-4-(isothiazol-2-ylsulfanyl)-benzamide; exo-N-[(4S)-1-azabicyclo[2.2.1]hept-3-yl]-4-(6-methylpyridin-3-yloxy)-benzamide; exo-N-[(4S)-1-azabicyclo[2.2.1]hept-3-yl]-4-(6-chloropyridin-3-yloxy)-benzamide; exo-N-[(4S)-1-azabicyclo[2.2.1]hept-3-yl]-4-(6-methoxypyridin-3-yloxy)-benzamide; exo-N-[(4S)-1-azabicyclo[2.2.1]hept-3-yl]-4-(6-trifluoromethylpyridin-3-yloxy)-benzamide;
exo-N-[(4S)-1-azabicyclo[2.2.1]hept-3-yl]-4-(2-chloropyridin-4-yloxy)-benzamide; exo-N-[(4S)-1-azabicyclo[2.2.1]hept-3-yl]-4-(5-chloropyridin-2-yloxy)-benzamide; exo-N-[(4S)-1-azabicyclo[2.2.1]hept-3-yl]-4-(4-chloropyridin-2-yloxy)-benzamide; exo-N-[(4S)-1-azabicyclo[2.2.1]hept-3-yl]-4-(6-chloropyridin-2-yloxy)-benzamide; exo-N-[(4S)-1-azabicyclo[2.2.1]hept-3-yl]-4-(5-chloropyridin-3-yloxy)-benzamide; exo-N-[(4S)-1-azabicyclo[2.2.1]hept-3-yl]-4-(2-chloropyridin-3-yloxy)-benzamide; exo-N-(4S)-1-azabicyclo[2.2.1]hept-3-yl]-4-(4-chloropyridin-3-yloxy)-benzamide; exo-N-[(4S)-1-azabicyclo[2.2.1]hept-3-yl]-4-(3-chloropyridin-4-yloxy)-benzamide;
exo-N-[(4S)-1-azabicyclo[2.2.1]hept-3-yl]-4-(3-chloropyridin-2-yloxy)-benzamide; exo-N-[(4S)-1-azabicyclo[2.2.1]hept-3-yl]-4-(6-chloropyridin-3-ylsulfanyl)-benzamide; N-[(3R,5R)-1-azabicyclo[3.2.1]oct-3-yl]-4-(4-hydroxyphenoxy)benzamide; N-[(3R,5R)-1-azabicyclo[3.2.1]oct-3-yl]-4-(4-acetamidophenoxy)benzamide; N-[(3R,5R)-1-azabicyclo[3.2.1]oct-3-yl]-4-phenoxybenzamide;
N-[(3R,5R)-1-azabicyclo[3.2.1]oct-3-yl]-4-benzylbenzamide;
N-[(3R,5R)-1-azabicyclo[3.2.1]oct-3-yl]-4-(phenylsulfanyl)-benzamide;
N-[(3R,5R)-1-azabicyclo[3.2.1]oct-3-yl]-3-phenoxybenzamide;
N-[(3R,5R)-1-azabicyclo[3.2.1]oct-3-yl]-4-(4-fluorophenoxy)benzamide;
N-[(3R,5R)-1-azabicyclo[3.2.1]oct-3-yl]-4-(2-fluorophenoxy)-benzamide;
N-[(3R,5R)-1-azabicyclo[3.2.1]oct-3-yl]-4-(3-fluorophenoxy)-benzamide;
N-[(3R,5R)-1-azabicyclo[3.2.1]oct-3-yl]-4-(2-chlorophenoxy)-benzamide;
N-[(3R,5R)-1-azabicyclo[3.2.1]oct-3-yl]-4-(3-chlorophenoxy)-benzamide;
N-[(3R,5R)-1-azabicyclo[3.2.1]oct-3-yl]-4-(4-chlorophenoxy)-benzamide;
N-[(3R,5R)-1-azabicyclo[3.2.1]oct-3-yl]-4-(2-methoxyphenoxy)-benzamide;
N-[(3R,5R)-1-azabicyclo[3.2.1]oct-3-yl]-4-(3-methoxyphenoxy)-benzamide;
N-[(3R,5R)-1-azabicyclo[3.2.1]oct-3-yl]-4-(4-methoxyphenoxy)-benzamide;
N-[(3R,5R)-1-azabicyclo[3.2.1]oct-3-yl]-4-(3-chlorophenylsulfanyl)benzami-de;
N-[(3R,5R)-1-azabicyclo[3.2.1]oct-3-yl]-4-(4-chlorophenyl-sulfanyl)ben-zamide;

N-[(3R,5R)-1-azabicyclo[3.2.1]oct-3-yl]-4-(2-chlorophenyl-sulfanyl-)benzamide;
N-[(3R,5R)-1-azabicyclo[3.2.1]oct-3-yl]-4-(4-methoxyphenyl-sul-fanyl)benzamide;
N-[(3R,5R)-1-azabicyclo[3.2.1]oct-3-yl]-4-(3-methoxypheny-l-sulfanyl)benzamide;
N-[(3R,5R)-1-azabicyclo[3.2.1]oct-3-yl]-4-(2-methoxyphenyl-sulfanyl)benzamide;
N-[(3R,5R)-1-azabicyclo[3.2.1]oct-3-yl]-4-(4-aminophenoxy)-benzamide;
N-[(3R,5R)-1-azabicyclo[3.2.1]oct-3-yl]-4-(3-aminophenoxy)-benzamide;
N-[(3R,5R)-1-azabicyclo[3.2.1]oct-3-yl]-4-(2-aminophenoxy)-benzamide;
N-[(3R,5R)-1-azabicyclo[3.2.1]oct-3-yl]-4-(4-acetylphenoxy)-benzamide;
N-[(3R,5R)-1-azabicyclo[3.2.1]oct-3-yl]-4-(3-acetylphenoxy)-be-nzamide;
N-[(3R,5R)-1-azabicyclo[3.2.1]oct-3-yl]-4-(2-acetylphenoxy)-benza-mide;
N-[(3R,5R)-1-azabicyclo[3.2.1]oct-3-yl]-4-(4-carbamoylphenoxy)-benza-mide;
N-[(3R,5R)-1-azabicyclo[3.2.1]oct-3-yl]-4-(3-carbamoylphenoxy)-benza-mide;
N-[(3R,5R)-1-azabicyclo[3.2.1]oct-3-yl]-4-(2-carbamoylphenoxy)-benza-mide;
N-[(3R,5R)-1-azabicyclo[3.2.1]oct-3-yl]-4-(4-cyanophenoxy)-benzamide;
N-[(3R,5R)-1-azabicyclo[3.2.1]oct-3-yl]-4-(3-cyanophenoxy)-benzamide;
N-[(3R,5R)-1-azabicyclo[3.2.1]oct-3-yl]-4-(2-cyanophenoxy)-benzamide;
N-[(3R,5R)-1-azabicyclo[3.2.1]oct-3-yl]-4-(thiophen-2-yloxy)-benzamide;
N-[(3R,5R)-1-azabicyclo[3.2.1]oct-3-yl]-4-(5-methylthiophen-2-yloxy)-benzamide; N-[(3R,5R)-1-azabicyclo[3.2.1]oct-3-yl]-4-(5-chlorothiophen-2-yloxy)-benzamide; N-[(3R,5R)-1-azabicyclo[3.2.1]oct-3-yl]-4-(5-methoxythiophen-2-yloxy)-benzamide; N-[(3R,5R)-1-azabicyclo[3.2.1]oct-3-yl]-4-(5-trifluoromethylthiophen-2-yloxy)-benzamide; N-[(3R,5R)-1-azabicyclo[3.2.1]oct-3-yl]-4-(4-methylthiophen-2-yloxy)-benzamide; N-[(3R,5R)-1-azabicyclo[3.2.1]oct-3-yl]-4-(4-chlorothiophen-2-yloxy)-benzamide; N-[(3R,5R)-1-azabicyclo[3.2.1]oct-3-yl]-4-(4-methoxythiophen-2-yloxy)-benzamide;
N-[(3R,5R)-1-azabicyclo[3.2.1]oct-3-yl]-4-(4-trifluoromethylthiophen-2-yloxy)-benzamide; N-[(3R,5R)-1-azabicyclo[3.2.1]oct-3-yl]-4-(furan-2-yloxy)-benzamide; N-[(3R,5R)-1-azabicyclo[3.2.1]oct-3-yl]-4-(5-methylfuran-2-yloxy)-benzamide; N-[(3R,5R)-1-azabicyclo[3.2.1]oct-3-yl]-4-(5-chlorofuran-2-yloxy)-benzamide; N-[(3R,5R)-1-azabicyclo[3.2.1]oct-3-yl]-4-(5-methoxyfuran-2-yloxy)-benzamide; N-[(3R,5R)-1-azabicyclo[3.2.1]oct-3-yl]-4-(5-trifluoromethylfuran-2-yloxy)-benzamide; N-[(3R,5R)-1-azabicyclo[3.2.1]oct-3-yl]-4-(4-methylfuran-2-yloxy)-benzamide; N-[(3R,5R)-1-azabicyclo[3.2.1]oct-3-yl]-4-(4-chlorofuran-2-yloxy)-benzamide; N-[(3R,5R)-1-azabicyclo[3.2.1]oct-3-yl]-4-(4-methoxyfuran-2-yloxy)-benzamide; N-[(3R,5R)-1-azabicyclo[3.2.1]oct-3-yl]-4-(4-trifluoromethylfuran-2-yloxy)-benzamide;
N-[(3R,5R)-1-azabicyclo[3.2.1]oct-3-yl]-4-(oxazol-2-yloxy)-benzamide;
N-[(3R,5R)-1-azabicyclo[3.2.1]oct-3-yl]-4-(oxazol-5-yloxy)-benzamide;
N-[(3R,5R)-1-azabicyclo[3.2.1]oct-3-yl]-4-(thiazol-2-yloxy)-benzamide;
N-[(3R,5R)-1-azabicyclo[3.2.1]oct-3-yl]-4-(thiazol-5-yloxy)-benzamide;
N-[(3R,5R)-1-azabicyclo[3.2.1]oct-3-yl]-4-([1,3,4]oxadiazol-2-yloxy)-benzamide; N-[(3R,5R)-1-azabicyclo[3.2.1]oct-3-yl]-4-([1,3,4]thiadiazol-2-yloxy)-benzamide; N-[(3R,5R)-1-azabicyclo[3.2.1]oct-3-yl]-4-(4-aminophenylsulfanyl)-benzamide; N-[(3R,5R)-1-azabicyclo[3.2.1]oct-3-yl]-4-(3-aminophenylsulfanyl)-benzamide; N-[(3R,5R)-1-azabicyclo[3.2.1]oct-3-yl]-4-(2-aminophenylsulfanyl)-benzamide; N-[(3R,5R)-1-azabicyclo[3.2.1]oct-3-yl]-4-(4-acetylphenylsulfanyl)-benzamide; N-[(3R,5R)-1-azabicyclo[3.2.1]oct-3-yl]-4-(3-acetylphenylsulfanyl)-benzamide; N-[(3R,5R)-1-azabicyclo[3.2.1]oct-3-yl]-4-(2-acetylphenylsulfanyl)-benzamide; N-[(3R,5R)-1-azabicyclo[3.2.1]oct-3-yl]-4-(4-carbamoylphenylsulfanyl)-benzamide; N-[(3R,5R)-1-azabicyclo[3.2.1]oct-3-yl]-4-(3-carbamoylphenylsulfanyl)-benzamide; N-[(3R,5R)-1-azabicyclo[3.2.1]oct-3-yl]-4-(2-carbamoylphenylsulfanyl)-benzamide;
N-[(3R,5R)-1-azabicyclo[3.2.1]oct-3-yl]-4-(4-hydroxyphenylsulfanyl)-benza-mide;
N-[(3R,5R)-1-azabicyclo[3.2.1]oct-3-yl]-4-(3-hydroxyphenylsulfanyl)-benzamide;
N-[(3R,5R)-1-azabicyclo[3.2.1]oct-3-yl]-4-(2-hydroxyphonylsulfa-nyl)-benzamide;
N-[(3R,5R)-1-azabicyclo[3.2.1]oct-3-yl]-4-(4-acetamidophenylsulfanyl)-benzamide; N-[(3R,5R)-1-azabicyclo[3.2.1]oct-3-yl]-4-(3-acetamidophenylsulfanyl)-benzamide; N-[(3R,5R)-1-azabicyclo[3.2.1]oct-3-yl]-4-(2-acetamidophenylsulfanyl)-benzamide; N-[(3R,5R)-1-azabicyclo[3.2.1]oct-3-yl]-4-(thiophen-2-ylsulfanyl)-benzamide; N-[(3R,5R)-1-azabicyclo[3.2.1]oct-3-yl]-4-(5-methylthiophen-2-ylsulfanyl)-benzamide; N-[(3R,5R)-1-azabicyclo[3.2.1]oct-3-yl]-4-(5-chlorothiophen-2-ylsulfanyl)-benzamide;
N-[(3R,5R)-1-azabicyclo[3.2.1]oct-3-yl]-4-(5-trifluoromethylthiophen-2-ylsulfanyl)-benzamide; N-[(3R,5R)-1-azabicyclo[3.2.1]oct-3-yl]-4-(furan-2-ylsulfanyl)-benzamide; N-[(3R,5R)-1-azabicyclo[3.2.1]oct-3-yl]-4-(5-methylfuran-2-ylsulfanyl)-benzamide; N-[(3R,5R)-1-azabicyclo[3.2.1]oct-3-yl]-4-(5-chlorofuran-2-ylsulfanyl)-benzamide; N-[(3R,5R)-1-azabicyclo[3.2.1]oct-3-yl]-4-(oxazol-2-ylsulfanyl)-benzamide; N-[(3R,5R)-1-azabicyclo[3.2.1]oct-3-yl]-4-(5-chlorooxazol-2-ylsulfanyl)-benzamide; N-[(3R,5R)-1-azabicyclo[3.2.1]oct-3-yl]-4-(5-methoxyoxazol-2-ylsulfanyl)-benzamide;
N-[(3R,5R)-1-azabicyclo[3.2.1]oct-3-yl]-4-(5-trifluoromethyloxazol-2-ylsulfanyl)-benzamide; N-[(3R,5R)-1-azabicyclo[3.2.1]oct-3-yl]-4-(oxazol-2-ylsulfanyl)-benzamide; N-[(3R,5R)-1-azabicyclo[3.2.1]oct-3-yl]-4-(oxazol-5-ylsulfanyl)-benzamide; N-[(3R,5R)-1-azabicyclo[3.2.1]oct-3-yl]-4-(thiazol-2-ylsulfanyl)-benzamide; N-[(3R,5R)-1-azabicyclo[3.2.1]oct-3-yl]-4-(thiazol-5-ylsulfanyl)-benzamide; N-[(3R,5R)-1-azabicyclo[3.2.1]oct-3-yl]-4-([1,3,4]oxadiazol-2-ylsulfanyl)-benzamide; N-[(3R,5R)-1-azabicyclo[3.2.1]oct-3-yl]-4-([1,3,4]thiadiazol-2-ylsulfanyl)-benzamide;
N-[(3R,5R)-1-azabicyclo[3.2.1]oct-3-yl]-4-(5-trifluoromethylpyrrol-2-yloxy)-benzamide;
N-[(3R,5R)-1-azabicyclo[3.2.1]oct-3-yl]-4-(3H-imidazol-4-yloxy)-benzamide;
N-[(3R,5R)-1-azabicyclo[3.2.1]oct-3-yl]-4-(isoxazol-2-yloxy)-benzamide;
N-[(3R,5R)-1-azabicyclo[3.2.1]oct-3-yl]-4-(isothiazol-2-yloxy)-benzamide;

N-[(3R,5R)-1-azabicyclo[3.2.1]oct-3-yl]-4-(pyrrol-2-ylsulfanyl)-benzamide;
N-[(3R,5R)-1-azabicyclo[3.2.1]oct-3-yl]-4-(3H-imidazol-4-ylsulfanyl)-benzamide; N-[(3R,5R)-1-azabicyclo[3.2.1]oct-3-yl]-4-(isoxazol-2-ylsulfanyl)-benzamide; N-[(3R,5R)-1-azabicyclo[3.2.1]oct-3-yl]-4-(isothiazol-2-ylsulfanyl)-benzamide; N-[(3R,5R)-1-azabicyclo[3.2.1]oct-3-yl]-4-(6-methylpyridin-3-yloxy)-benzamide; N-[(3R,5R)-1-azabicyclo[3.2.1]oct-3-yl]-4-(6-chloropyridin-3-yloxy)-benzamide; N-[(3R,5R)-1-azabicyclo[3.2.1]oct-3-yl]-4-(6-methoxypyridin-3-yloxy)-benzamide; N-[(3R,5R)-1-azabicyclo[3.2.1]oct-3-yl]-4-(6-trifluoromethylpyridin-3-yloxy)-benzamide; N-[(3R,5R)-1-azabicyclo[3.2.1]oct-3-yl]-4-(2-chloropyridin-4-yloxy)-benzamide; N-[(3R,5R)-1-azabicyclo[3.2.1]oct-3-yl]-4-(5-chloropyridin-2-yloxy)-benzamide;
N-[(3R,5R)-1-azabicyclo[3.2.1]oct-3-yl]-4-(4-chloropyridin-2-yloxy)-benza-mide;
N-[(3R,5R)-1-azabicyclo[3.2.1]oct-3-yl]-4-(6-chloropyridin-2-yloxy)-benzamide;
N-[(3R,5R)-1-azabicyclo[3.2.1]oct-3-yl]-4-(5-chloropyridin-3-yl-oxy)-benzamide;
N-[(3R,5R)-1-azabicyclo[3.2.1]oct-3-yl]-4-(2-chloropyridin-3-yloxy)-benzamide;
N-[(3R,5R)-1-azabicyclo[3.2.1]oct-3-yl]-4-(4-chloropyridin-3-yloxy)-benzamide;
N-[(3R,5R)-1-azabicyclo[3.2.1]oct-3-yl]-4-(3-chloropyridin-4-yloxy)-benzamide;
N-[(3R,5R)-1-azabicyclo[3.2.1]oct-3-yl]-4-(-3-chloropyridin-2-yloxy)-benzamide;
N-[(3R,5R)-1-azabicyclo[3.2.1]oct-3-yl]-4-(6-chloropyridin-3-ylsulfanyl)-benzamide; N-[1-azabicyclo[3.2.2]nonan-3-yl]-4-(4-hydroxyphenoxy)benzamide; N-[1-azabicyclo[3.2.2]nonan-3-yl]-4-(4-acetamidophenoxy)benzamide; N-[1-azabicyclo[3.2.2]nonan-3-yl]-4-phenoxybenzamide; N-[1-azabicyclo[3.2.2]nonan-3-yl]-4-benzylbenzamide;
N-[1-azabicyclo[3.2.2]nonan-3-yl]-4-(phenylsulfanyl)-benzamide;
N-[1-azabicyclo[3.2.2]nonan-3-yl]-3-phenoxybenzamide;
N-[1-azabicyclo[3.2.2]nonan-3-yl]-4-(4-fluorophenoxy)benzamide;
N-[1-azabicyclo[3.2.2]nonan-3-yl]-4-(2-fluorophenoxy)-benzamide;
N-[1-azabicyclo[3.2.2]nonan-3-yl]-4-(3-fluorophenoxy)-benzamide;
N-[1-azabicyclo[3.2.2]nonan-3-yl]-4-(2-chlorophenoxy)-benzamide;
N-[1-azabicyclo[3.2.2]nonan-3-yl]-4-(3-chlorophenoxy)-benzamide;
N-[1-azabicyclo[3.2.2]nonan-3-yl]-4-(4-chlorophenoxy)-benzamide;
N-[1-azabicyclo[3.2.2]nonan-3-yl]-4-(2-methoxyphenoxy)-benzamide;
N-[1-azabicyclo[3.2.2]nonan-3-yl]-4-(3-methoxyphenoxy)-benzamide;
N-[1-azabicyclo[3.2.2]nonan-3-yl]-4-(4-methoxyphenoxy)-benzamide;
N-[1-azabicyclo[3.2.2]nonan-3-yl]-4-(3-chlorophenylsulfanyl)benzamide;
N-[1-azabicyclo[3.2.2]nonan-3-yl]-4-(4-chlorophenylsulfanyl)benzamide;
N-[1-azabicyclo[3.2.2]nonan-3-yl]-4-(2-chlorophenylsulfanyl)benzamide;
N-[1-azabicyclo[3.2.2]nonan-3-yl]-4-(4-methoxyphenylsulfanyl)benzamide;
N-[1-azabicyclo[3.2.2]nonan-3-yl]-4-(3-methoxyphenylsulfanyl)benzamide;
N-[1-azabicyclo[3.2.2]nonan-3-yl]-4-(2-methoxyphenylsulfanyl)benzamide;
N-[1-azabicyclo[3.2.2]nonan-3-yl]-4-(4-aminophenoxy)-benzamide;
N-[1-azabicyclo[3.2.2]nonan-3-yl]-4-(3-aminophenoxy)-benzamide;
N-[1-azabicyclo[3.2.2]nonan-3-yl]-4-(2-aminophenoxy)-benzamide;
N-[1-azabicyclo[3.2.2]nonan-3-yl]-4-(4-acetylphenoxy)-benzamide;
N-[1-azabicyclo[3.2.2]nonan-3-yl]-4-(3-acetylphenoxy)-benzamide;
N-[1-azabicyclo[3.2.2]nonan-3-yl]-4-(2-acetylphenoxy)-benzamide;
N-[1-azabicyclo[3.2.2]nonan-3-yl]-4-(4-carbamoylphenoxy)-benzamide;
N-[1-azabicyclo[3.2.2]nonan-3-yl]-4-(3-carbamoylphenoxy)-benzamide;
N-[1-azabicyclo[3.2.2]nonan-3-yl]-4-(2-carbamoylphenoxy)-benzamide;
N-[1-azabicyclo[3.2.2]nonan-3-yl]-4-(4-cyanophenoxy)-benzamide;
N-[1-azabicyclo[3.2.2]nonan-3-yl]-4-(3-cyanophenoxy)-benzamide;
N-[1-azabicyclo[3.2.2]nonan-3-yl]-4-(2-cyanophenoxy)-benzamide;
N-[1-azabicyclo[3.2.2]nonan-3-yl]-4-(thiophen-2-yloxy)-benzamide;
N-[1-azabicyclo[3.2.2]nonan-3-yl]-4-(5-methylthiophen-2-yloxy)-benzamide;
N-[1-azabicyclo[3.2.2]nonan-3-yl]-4-(5-chlorothiophen-2-yloxy)-benzamide;
N-[1-azabicyclo[3.2.2]nonan-3-yl]-4-(5-methoxythiophen-2-yloxy)-benzamide;
N-[1-azabicyclo[3.2.2]nonan-3-yl]-4-(5-trifluoromethylthiophen-2-yloxy)-benzamide; N-[1-azabicyclo[3.2.2]nonan-3-yl]-4-(4-methylthiophen-2-yloxy)-benzamide; N-[1-azabicyclo[3.2.2]nonan-3-yl]-4-(4-chlorothiophen-2-yloxy)-benzamide; N-[1-azabicyclo[3.2.2]nonan-3-yl]-4-(4-methoxythiophen-2-yloxy)-benzamide; N-[1-azabicyclo[3.2.2]nonan-3-yl]-4-(4-trifluoromethylthiophen-2-yloxy)-benzamide; N-[1-azabicyclo[3.2.2]nonan-3-yl]-4-(furan-2-yloxy)-benzamide; N-[1-azabicyclo[3.2.2]nonan-3-yl]-4-(5-methylfuran-2-yloxy)-benzamide; N-[1-azabicyclo[3.2.2]nonan-3-yl]-4-(5-chlorofuran-2-yloxy)-benzami-de;
N-[1-azabicyclo[3.2.2]nonan-3-yl]-4-(5-methoxyfuran-2-yloxy)-benzamide;
N-[1-azabicyclo[3.2.2]nonan-3-yl]-4-(5-trifluoromethylfuran-2-yloxy)-benzamide; N-[1-azabicyclo[3.2.2]nonan-3-yl]-4-(4-methylfuran-2-yloxy)-benzam-ide;
N-[1-azabicyclo[3.2.2]nonan-3-yl]-4-(4-chlorofuran-2-yloxy)-benzamide;
N-[1-azabicyclo[3.2.2]nonan-3-yl]-4-(4-methoxyfuran-2-yloxy)-benzamide;
N-[1-azabicyclo[3.2.2]nonan-3-yl]-4-(4-trifluoromethylfuran-2-yloxy)-benzamide; N-[1-azabicyclo[3.2.2]nonan-3-yl]-4-(oxazol-2-yloxy)-benzamide;
N-[1-azabicyclo[3.2.2]nonan-3-yl]-4-(oxazol-5-yloxy)-benzamide;
N-[1-azabicyclo[3.2.2]nonan-3-yl]-4-(thiazol-2-yloxy)-benzamide;
N-[1-azabicyclo[3.2.2]nonan-3-yl]-4-(thiazol-5-yloxy)-benzamide;

N-[1-azabicyclo[3.2.2]nonan-3-yl]-4-([1,3,4]oxadiazol-2-yloxy)-benzamide;
N-[1-azabicyclo[3.2.2]nonan-3-yl]-4-([1,3,4]thiadiazol-2-yloxy)-benzamide;
N-[1-azabicyclo[3.2.2]nonan-3-yl]-4-(4-aminophenylsulfanyl)-benzamide;
N-[11-azabicyclo[3.2.2]nonan-3-yl]-4-(3-aminophenylsulfanyl)-benzamide;
N-[1-azabicyclo[3.2.2]nonan-3-yl]-4-(2-aminophenylsulfanyl)-benzamide;
N-[1-azabicyclo[3.2.2]nonan-3-yl]-4-(4-acetylphenylsulfanyl)-benzamide;
N-[1-azabicyclo[3.2.2]nonan-3-yl]-4-(3-acetylphenylsulfanyl)-benzamide;
N-[1-azabicyclo[3.2.2]nonan-3-yl]-4-(2-acetylphenylsulfanyl)-benzamide;
N-[1-azabicyclo[3.2.2]nonan-3-yl]-4-(4-carbamoylphenylsulfanyl)-benzamide;
N-[1-azabicyclo[3.2.2]nonan-3-yl]-4-(3-carbamoylphenylsulfanyl)-benzamid-e;
N-[1-azabicyclo[3.2.2]nonan-3-yl]-4-(2-carbamoylphenylsulfanyl)-benzami-de;
N-[1-azabicyclo[3.2.2]nonan-3-yl]-4-(4-hydroxyphenylsulfanyl)-benzamid-e;
N-[1-azabicyclo[3.2.2]nonan-3-yl]-4-(3-hydroxyphenylsulfanyl)-benzamide;
N-[1-azabicyclo[3.2.2]nonan-3-yl]-4-(2-hydroxyphenylsulfanyl)-benzamide;
N-[1-azabicyclo[3.2.2]nonan-3-yl]-4-(4-acetamidophenylsulfanyl)-benzamide;
N-[1-azabicyclo[3.2.2]nonan-3-yl]-4-(3-acetamidophenylsulfanyl)-benzamid-e;
N-[1-azabicyclo[3.2.2]nonan-3-yl]-4-(2-acetamidophenylsulfanyl)-benzami-de;
N-[1-azabicyclo[3.2.2]nonan-3-yl]-4-(thiophen-2-ylsulfanyl)-benzamide;
N-[1-azabicyclo[3.2.2]nonan-3-yl]-4-(5-methylthiophen-2-ylsulfanyl)-benza-mide;
N-[1-azabicyclo[3.2.2]nonan-3-yl]-4-(5-chloro thiophen-2-ylsulfanyl)-benzamide;
N-[1-azabicyclo[3.2.2]nonan-3-yl]-4-(5-trifluoromethylthiophen-2-ylsulfanyl)-benzamide; N-[1-azabicyclo[3.2.2]nonan-3-yl]-4-(furan-2-ylsulfanyl)-benzamide; N-[1-azabicyclo[3.2.2]nonan-3-yl]-4-(5-methylfuran-2-ylsulfanyl)-benzamide; N-[1-azabicyclo[3.2.2]nonan-3-yl]-4-(5-chlorofuran-2-ylsulfanyl)-benzamide; N-[1-azabicyclo[3.2.2]nonan-3-yl]-4-(oxazol-2-ylsulfanyl)-benzamide; N-[1-azabicyclo[3.2.2]nonan-3-yl]-4-(5-chlorooxazol-2-ylsulfanyl)-benzamide; N-[1-azabicyclo[3.2.2]nonan-3-yl]-4-(5-methoxyoxazol-2-ylsulfanyl)-benzamide; N-[1-azabicyclo[3.2.2]nonan-3-yl]-4-(5-trifluoromethyloxazol-2-ylsulfanyl)-benzamide;
N-[1-azabicyclo[3.2.2]nonan-3-yl]-4-(oxazol-2-ylsulfanyl)-benzamide;
N-[1-azabicyclo[3.2.2]nonan-3-yl]-4-(oxazol-5-ylsulfanyl)-benzamide;
N-[1-azabicyclo[3.2.2]nonan-3-yl]-4-(thiazol-2-ylsulfanyl)-benzamide;
N-[1-azabicyclo[3.2.2]nonan-3-yl]-4-(thiazol-5-ylsulfanyl)-benzamide;
N-[1-azabicyclo[3.2.2]nonan-3-yl]-4-([1,3,4]oxadiazol-2-ylsulfanyl)-benza-mide;
N-[1-azabicyclo[3.2.2]nonan-3-yl]-4-([1,3,4]thiadiazol-2-ylsulfanyl)-benzamide; N-[1-azabicyclo[3.2.2]nonan-3-yl]-4-(5-trifluoromethylpyrrol-2-yloxy)-benzamide; N-[1-azabicyclo[3.2.2]nonan-3-yl]-4-(3H-imidazol-4-yloxy)-benzamide; N-[1-azabicyclo[3.2.2]nonan-3-yl]-4-(isoxazol-2-yloxy)-benzamide; N-[1-azabicyclo[3.2.2]nonan-3-yl]-4-(isothiazol-2-yloxy)-benzamide;
N-[1-azabicyclo[3.2.2]nonan-3-yl]-4-(pyrrol-2-ylsulfanyl)-benzamide;
N-[1-azabicyclo[3.2.2]nonan-3-y]-4-(3H-imidazol-4-ylsulfanyl)-benzamide;
N-[1-azabicyclo[3.2.2]nonan-3-yl]-4-(isoxazol-2-ylsulfanyl)-benzamide;
N-[1-azabicyclo[3.2.2]nonan-3-yl]-4-(isothiazol-2-ylsulfanyl)-benzamide;
N-[1-azabicyclo[3.2.2]nonan-3-yl]-4-(6-methylpyridin-3-yloxy)-benzamide;
N-[1-azabicyclo[3.2.2]nonan-3-yl]-4-(6-chloropyridin-3-yloxy)-benzamide;
N-[1-azabicyclo[3.2.2]nonan-3-yl]-4-(6-methoxypyridin-3-yloxy)-benzamide;
N-[1-azabicyclo[3.2.2]nonan-3-yl]-4-(6-trifluoromethylpyridin-3-yloxy)-benzamide; N-[1-azabicyclo[3.2.2]nonan-3-yl]-4-(2-chloropyridin-4-yloxy)-benzamide; N-[1-azabicyclo[3.2.2]nonan-3-yl]-4-(5-chloropyridin-2-yloxy)-benzamide; N-[1-azabicyclo[3.2.2]nonan-3-yl]-4-(4-chloropyridin-2-yloxy)-benzamide; N-[1-azabicyclo[3.2.2]nonan-3-yl]-4-(6-chloropyridin-2-yloxy)-benzam-ide;
N-[1-azabicyclo[3.2.2]nonan-3-yl]-4-(5-chloropyridin-3-yloxy)-benzami-de;
N-[1-azabicyclo[3.2.2]nonan-3-yl]-4-(2-chloropyridin-3-yloxy)-benzamid-e;
N-[1-azabicyclo[3.2.2]nonan-3-yl]-4-(4-chloropyridin-3-yloxy)-benzamide;
N-[1-azabicyclo[3.2.2]nonan-3-yl]-4-(3-chloropyridin-4-yloxy)-benzamide;
N-[1-azabicyclo[3.2.2]nonan-3-yl]-4-(3-chloropyridin-2-yloxy)-benzamide;
N-[1-azabicyclo[3.2.2]nonan-3-yl]-4-(6-chloropyridin-3-ylsulfanyl)-benzamide;
or pharmaceutically acceptable salt thereof.

9. A pharmaceutical composition comprising a compound according to claim 1 and a pharmaceutically acceptable excipient.

10. The pharmaceutical composition according to claim 9, wherein said compound is administered rectally, topically, orally, sublingually, or parenterally for a therapeutically effective interval.

11. The pharmaceutical composition according to claim 10, wherein said compound is administered in an amount of from about 0.001 to about 100 mg/kg of body weight of said mammal per day.

12. The pharmaceutical composition according to claim 10, wherein said compound is administered in an amount of from about 0.1 to about 50 mg/kg of body weight of said mammal per day.

* * * * *